United States Patent
Chen et al.

(10) Patent No.: US 9,969,973 B2
(45) Date of Patent: May 15, 2018

(54) METHODS AND COMPOSITIONS FOR CELL ATTACHMENT AND CULTIVATION ON PLANAR SUBSTRATES

(75) Inventors: Ya Xiong Chen, Skillman, NJ (US); Benjamin Fryer, Skillman, NJ (US)

(73) Assignee: Janssen Biotech, Inc., Horsham, PA (US)

( * ) Notice: Subject to any disclaimer, the term of this patent is extended or adjusted under 35 U.S.C. 154(b) by 443 days.

(21) Appl. No.: 12/621,702

(22) Filed: Nov. 19, 2009

(65) Prior Publication Data

US 2010/0124783 A1 May 20, 2010

Related U.S. Application Data

(60) Provisional application No. 61/116,452, filed on Nov. 20, 2008.

(51) Int. Cl.
*C12N 5/0735* (2010.01)

(52) U.S. Cl.
CPC ...... *C12N 5/0606* (2013.01); *C12N 2501/727* (2013.01); *C12N 2501/999* (2013.01); *C12N 2533/30* (2013.01); *C12N 2533/50* (2013.01); *C12N 2533/78* (2013.01); *C12N 2533/90* (2013.01)

(58) Field of Classification Search
CPC .................................................... C12N 5/0606
See application file for complete search history.

(56) References Cited

U.S. PATENT DOCUMENTS

| | | |
|---|---|---|
| 3,209,652 A | 10/1965 | Burgsmueller |
| 3,845,641 A | 11/1974 | Waller |
| 3,935,067 A | 1/1976 | Thayer |
| 4,499,802 A | 2/1985 | Simpson |
| 4,537,773 A | 8/1985 | Shenvi |
| 4,557,264 A | 12/1985 | Hinsch |
| 4,737,578 A | 4/1988 | Evans et al. |
| 5,215,893 A | 6/1993 | Mason et al. |
| 5,449,383 A | 9/1995 | Chatelier et al. |
| 5,525,488 A | 6/1996 | Mason et al. |
| 5,567,612 A | 10/1996 | Vacanti et al. |
| 5,665,568 A | 9/1997 | Mason et al. |
| 5,686,090 A | 11/1997 | Schilder et al. |
| 5,713,957 A | 2/1998 | Steele et al. |
| 5,716,810 A | 2/1998 | Mason et al. |
| 5,718,922 A | 2/1998 | Herrero-Vanrell |
| 5,759,830 A | 6/1998 | Vacanti et al. |
| 5,770,417 A | 6/1998 | Vacanti et al. |
| 5,780,454 A | 7/1998 | Adams et al. |
| 5,834,308 A | 11/1998 | Peck et al. |
| 5,843,780 A | 12/1998 | Thomson |
| 5,888,816 A | 3/1999 | Coon et al. |
| 5,908,782 A | 6/1999 | Marshank et al. |
| 5,914,262 A | 6/1999 | MacMichael et al. |
| 5,942,435 A | 8/1999 | Wheeler |
| 6,001,647 A | 12/1999 | Peck et al. |
| 6,022,743 A | 2/2000 | Naughton et al. |
| 6,087,113 A | 6/2000 | Caplan et al. |
| 6,083,903 A | 7/2000 | Adams et al. |
| 6,200,806 B1 | 3/2001 | Thomson |
| 6,261,549 B1 | 6/2001 | Fernandez et al. |
| 6,281,012 B1 | 8/2001 | McIntosh et al. |
| 6,297,217 B1 | 10/2001 | Adams et al. |
| 6,306,424 B1 | 10/2001 | Vyakarnan et al. |
| 6,328,960 B1 | 12/2001 | McIntosh et al. |
| 6,331,298 B1 | 12/2001 | Ferguson et al. |
| 6,333,029 B1 | 12/2001 | Vyakarnam et al. |
| 6,365,149 B2 | 2/2002 | Vyakarnam et al. |
| 6,413,773 B1 | 7/2002 | Ptasznik et al. |
| 6,436,704 B1 | 8/2002 | Roberts et al. |
| 6,458,589 B1 | 10/2002 | Rambhatla et al. |
| 6,458,593 B1 | 10/2002 | Musick et al. |
| 6,509,369 B2 | 1/2003 | Scott et al. |
| 6,521,427 B1 | 2/2003 | Evans |
| 6,534,084 B1 | 3/2003 | Vyakarnam et al. |
| 6,599,323 B2 | 7/2003 | Melican et al. |
| 6,617,152 B2 * | 9/2003 | Bryhan ............... B05D 3/144 118/723 ME |
| 6,617,317 B1 | 9/2003 | Adams et al. |
| 6,626,950 B2 | 9/2003 | Brown et al. |
| 6,642,048 B2 | 11/2003 | Xu et al. |
| 6,656,488 B2 | 12/2003 | Yi et al. |
| 6,670,127 B2 | 12/2003 | Evans |
| 6,703,017 B1 | 3/2004 | Peck et al. |
| 6,713,446 B2 | 3/2004 | Gupta |
| 6,793,945 B2 | 9/2004 | Bathurst et al. |
| 6,800,480 B1 | 10/2004 | Bodnar et al. |
| 6,815,203 B1 | 11/2004 | Bonner-Weir et al. |

(Continued)

FOREIGN PATENT DOCUMENTS

| | | |
|---|---|---|
| CN | 1389565 A | 7/2002 |
| CN | 1602351 A | 3/2005 |

(Continued)

OTHER PUBLICATIONS

Watanabe et al., 2007. Nat. Biot., vol. 25(6), pp. 681-686.*
Xu et al., 2001, Nature Biotechnology, vol. 19, pp. 971-974.*
Kohen et al., 2009, Biointerphases, vol. 4(4), pp. 69-79.*
Moore et al., 2002, DNA and Cell Biol., vol. 21(5/6), pp. 443-451.*
Thomson et al., 2005, PNAS, vol. 92, pp. 7844-7848.*
NIH-Stem Cells: Scientific Progress and Future Research Directions, Department of Health and Human Services, Chapters 1 and 3, p. 14, Jun. 2001.*
Lanza et al., 2010, Stem Cell Anthology, Academic Press, 1st Ed., pp. 141, 142, 44 and 46.*
Yu et al., 2006, American J. Pathology, vol. 168(6), pp. 1879-1888.*
Blin et al., 2010, JCI, vol. 120(4), pp. 1125-1139.*
Lim et al., Proteomics, 2:1187-1203, 2002.*
Prowse et al., Proteomics, 5:978-989, 2005.*
Thomson, PNAS, 92: 7844-7848, Aug. 1995.*
Oh et al., Clin. and Exp. Pharmacology and Physiology, 33:489-495, 2006.*
Ludwig et al., Nat. Biotech., 24(2): 185-187, 2006.*
Xu et al., Nature Biotech., 19: 971-974, 2001.*

(Continued)

*Primary Examiner* — Thaian N Ton
*Assistant Examiner* — David A. Montanari
(74) *Attorney, Agent, or Firm* — Lois A. Gianneschi

(57) ABSTRACT

The present invention is directed to methods for the growth, expansion and differentiation of pluripotent stem cells on planar substrates lacking an adlayer and a feeder cell layer.

20 Claims, 13 Drawing Sheets

(56) References Cited

U.S. PATENT DOCUMENTS

| | | | |
|---|---|---|---|
| 6,958,319 B2 | 10/2005 | Gupta | |
| 6,987,110 B2 | 1/2006 | Zhang et al. | |
| 7,005,252 B1 | 2/2006 | Thomson et al. | |
| 7,033,831 B2 | 4/2006 | Fisk et al. | |
| 7,157,275 B2 | 1/2007 | Guarino et al. | |
| 7,297,539 B2 | 11/2007 | Mandalam et al. | |
| 7,326,572 B2 | 2/2008 | Fisk et al. | |
| 7,371,576 B2 | 5/2008 | Tsang et al. | |
| 7,410,798 B2 | 8/2008 | Mandalam et al. | |
| 7,413,734 B2 | 8/2008 | Mistry et al. | |
| 7,442,548 B2 | 10/2008 | Thomson et al. | |
| 7,449,334 B2 | 11/2008 | Thomsom et al. | |
| 7,510,873 B2 | 3/2009 | Mistry et al. | |
| 7,510,876 B2 | 3/2009 | D;Amour et al. | |
| 7,534,608 B2 | 5/2009 | Martinson et al. | |
| 7,569,385 B2 | 8/2009 | Haas | |
| 7,585,672 B2 | 9/2009 | Odorico et al. | |
| 7,704,738 B2 | 4/2010 | D'Amour et al. | |
| 7,993,920 B2 | 8/2011 | Martinson et al. | |
| 8,187,878 B2 | 5/2012 | Dalton et al. | |
| 8,859,286 B2 | 10/2014 | Agulnick | |
| 2002/0072117 A1 | 6/2002 | Xu et al. | |
| 2002/0151053 A1* | 10/2002 | Carpenter | C12N 15/1034 435/366 |
| 2003/0082155 A1 | 5/2003 | Habener | |
| 2003/0138948 A1 | 7/2003 | Fisk et al. | |
| 2003/0180268 A1 | 9/2003 | Atala | |
| 2003/0180903 A1 | 9/2003 | Bryhan et al. | |
| 2004/0015805 A1 | 1/2004 | Kidd | |
| 2004/0058412 A1 | 3/2004 | Ho et al. | |
| 2004/0062753 A1 | 4/2004 | Rezania | |
| 2004/0078090 A1* | 4/2004 | Binette | A61L 27/36 623/23.76 |
| 2004/0106196 A1 | 6/2004 | Fraser et al. | |
| 2004/0121460 A1 | 6/2004 | Lumelsky et al. | |
| 2004/0121461 A1 | 6/2004 | Honmou et al. | |
| 2004/0132729 A1 | 7/2004 | Salituro et al. | |
| 2004/0161419 A1 | 8/2004 | Strom et al. | |
| 2004/0171623 A1 | 9/2004 | Reynolds et al. | |
| 2004/0209901 A1 | 10/2004 | Adams et al. | |
| 2004/0220393 A1 | 11/2004 | Ward et al. | |
| 2004/0241761 A1 | 12/2004 | Sarvetnick | |
| 2005/0037491 A1 | 2/2005 | Mistry et al. | |
| 2005/0053588 A1 | 3/2005 | Yin et al. | |
| 2005/0054093 A1 | 3/2005 | Haas | |
| 2005/0054098 A1 | 3/2005 | Mistry et al. | |
| 2005/0054102 A1 | 3/2005 | Wobus et al. | |
| 2005/0058631 A1 | 3/2005 | Kihm et al. | |
| 2005/0063961 A1 | 3/2005 | Friedlander et al. | |
| 2005/0148070 A1 | 7/2005 | Thomson | |
| 2005/0158852 A1 | 7/2005 | D'Amour et al. | |
| 2005/0187298 A1 | 8/2005 | Vasudevan et al. | |
| 2005/0037488 A1 | 9/2005 | Mitalipova | |
| 2005/0208029 A1 | 9/2005 | Umezawa et al. | |
| 2005/0233446 A1 | 10/2005 | Parsons et al. | |
| 2005/0244962 A1 | 11/2005 | Thomson | |
| 2005/0260749 A1 | 11/2005 | Odorico et al. | |
| 2005/0266554 A1 | 12/2005 | D'Amour | |
| 2006/0003446 A1 | 1/2006 | Keller | |
| 2006/0030042 A1 | 2/2006 | Brivaniou et al. | |
| 2006/0040387 A1 | 2/2006 | Fisk | |
| 2006/0073588 A1* | 4/2006 | Adkisson | C12N 5/0655 435/366 |
| 2006/0148081 A1 | 7/2006 | Kelly et al. | |
| 2006/0194315 A1 | 8/2006 | Condie et al. | |
| 2006/0194321 A1 | 8/2006 | Colman et al. | |
| 2006/0281174 A1 | 12/2006 | Xu et al. | |
| 2007/0010011 A1 | 1/2007 | Parsons et al. | |
| 2007/0082397 A1 | 4/2007 | Hasson et al. | |
| 2007/0122903 A1 | 5/2007 | Rezania et al. | |
| 2007/0122905 A1 | 5/2007 | D'Amour et al. | |
| 2007/0154981 A1 | 7/2007 | Hori et al. | |
| 2007/0155013 A1 | 7/2007 | Akaike et al. | |
| 2007/0155661 A1 | 7/2007 | Kim | |
| 2007/0254359 A1 | 11/2007 | Rezania | |
| 2007/0259421 A1 | 11/2007 | D'Amour et al. | |
| 2007/0259423 A1 | 11/2007 | Odorico | |
| 2007/0264713 A1 | 11/2007 | Terstegge et al. | |
| 2008/0091234 A1 | 4/2008 | Kladakis et al. | |
| 2008/0159994 A1 | 7/2008 | Mantalaris et al. | |
| 2008/0241107 A1 | 10/2008 | Copland, III et al. | |
| 2008/0260700 A1 | 10/2008 | Accili et al. | |
| 2008/0267926 A1 | 10/2008 | Martinson et al. | |
| 2008/0268533 A1 | 10/2008 | Dalton et al. | |
| 2008/0268534 A1 | 10/2008 | Robins et al. | |
| 2009/0004152 A1 | 1/2009 | Martinson et al. | |
| 2009/0029462 A1 | 1/2009 | Beardsley et al. | |
| 2009/0053182 A1 | 2/2009 | Ichim et al. | |
| 2009/0093055 A1 | 4/2009 | Fisk et al. | |
| 2009/0170198 A1 | 7/2009 | Rezania | |
| 2009/0203141 A1 | 8/2009 | Lin et al. | |
| 2009/0263896 A1 | 10/2009 | Kelly et al. | |
| 2009/0269845 A1 | 10/2009 | Rezania et al. | |
| 2009/0298178 A1 | 12/2009 | D'Amour | |
| 2009/0325293 A1 | 12/2009 | Davis et al. | |
| 2010/0003749 A1 | 1/2010 | Uchida et al. | |
| 2010/0015100 A1 | 1/2010 | Xu | |
| 2010/0015711 A1 | 1/2010 | Davis et al. | |
| 2010/0028307 A1 | 2/2010 | O'Neil | |
| 2010/0093053 A1 | 4/2010 | Oh et al. | |
| 2010/0112691 A1 | 5/2010 | Green et al. | |
| 2010/0112693 A1 | 5/2010 | Rezania et al. | |
| 2010/0255580 A1 | 10/2010 | Rezania | |
| 2011/0014703 A1 | 1/2011 | Xu et al. | |
| 2011/0104805 A1 | 5/2011 | Fung et al. | |
| 2011/0151560 A1 | 6/2011 | Xu | |
| 2011/0151561 A1 | 6/2011 | Davis et al. | |
| 2011/0229441 A1 | 9/2011 | Benchoua et al. | |
| 2011/0280842 A1 | 11/2011 | Melton et al. | |
| 2011/0281355 A1 | 11/2011 | Xu | |
| 2012/0045830 A1 | 2/2012 | Green et al. | |
| 2012/0052576 A1 | 3/2012 | Rezania | |
| 2012/0190111 A1 | 7/2012 | Davis et al. | |
| 2012/0264209 A1 | 10/2012 | Odorico et al. | |
| 2013/0189777 A1 | 7/2013 | Rezania | |
| 2013/0224156 A1 | 8/2013 | Takahashi et al. | |
| 2014/0186953 A1 | 7/2014 | Rezania | |

FOREIGN PATENT DOCUMENTS

| | | |
|---|---|---|
| CN | 1671835 A | 9/2005 |
| CN | 1946838 A | 4/2007 |
| CN | 101092606 A | 12/2007 |
| CN | 101310012 A | 11/2008 |
| CN | 101410509 A | 4/2009 |
| CN | 101541953 A | 9/2009 |
| CN | 101611016 A | 12/2009 |
| EP | 0363125 A2 | 4/1990 |
| EP | 0348969 B1 | 5/1993 |
| EP | 0617126 B1 | 9/1994 |
| EP | 0800829 B1 | 10/1997 |
| EP | 0092302 B1 | 11/2006 |
| EP | 1873237 A1 | 1/2008 |
| EP | 1391505 B1 | 1/2009 |
| EP | 2088190 A1 | 8/2009 |
| EP | 2479260 B1 | 6/2016 |
| GB | 2484873 B2 | 4/2014 |
| JP | 2005506074 A2 | 3/2003 |
| JP | 2006-500003 A2 | 1/2006 |
| JP | 2008500809 A2 | 1/2008 |
| JP | 2009513143 A2 | 4/2009 |
| KR | 10-2008-0020098 A | 3/2008 |
| RU | 2359030 C1 | 6/2009 |
| RU | 2359671 C2 | 6/2009 |
| WO | WO199219759 A2 | 2/1992 |
| WO | 1996040172 A1 | 12/1996 |
| WO | 199847892 A1 | 10/1998 |
| WO | WO199920741 A1 | 4/1999 |
| WO | 200029549 A1 | 5/2000 |
| WO | 200123528 A1 | 4/2001 |
| WO | WO200151616 A2 | 7/2001 |
| WO | WO200181549 A3 | 11/2001 |
| WO | 200246183 A2 | 6/2002 |
| WO | 200246197 A1 | 6/2002 |

(56) References Cited

FOREIGN PATENT DOCUMENTS

| | | |
|---|---|---|
| WO | 2002086107 A2 | 10/2002 |
| WO | 02092756 A2 | 11/2002 |
| WO | 03033697 A1 | 4/2003 |
| WO | 2003026584 A2 | 4/2003 |
| WO | 2003029445 A1 | 4/2003 |
| WO | 2003042405 A2 | 5/2003 |
| WO | WO200305049 A1 | 6/2003 |
| WO | 2003054169 A1 | 7/2003 |
| WO | 2003062405 A2 | 7/2003 |
| WO | 2003095452 A1 | 11/2003 |
| WO | 03103972 A1 | 12/2003 |
| WO | WO2003102134 A2 | 12/2003 |
| WO | 2004016747 A2 | 2/2004 |
| WO | WO2004011621 A2 | 2/2004 |
| WO | 2004044158 A2 | 5/2004 |
| WO | 2004050827 A2 | 6/2004 |
| WO | 2004055155 A2 | 7/2004 |
| WO | 2004073633 A1 | 9/2004 |
| WO | 2004087885 A2 | 10/2004 |
| WO | WO2004090110 A2 | 10/2004 |
| WO | 2004067001 A1 | 12/2004 |
| WO | 2005080598 A1 | 1/2005 |
| WO | WO2005001077 A2 | 1/2005 |
| WO | 2005017117 A2 | 2/2005 |
| WO | WO 2005/014799 A1 | 2/2005 |
| WO | 2005058301 A1 | 6/2005 |
| WO | 2005063971 A1 | 7/2005 |
| WO | WO 2005/065354 A2 | 7/2005 |
| WO | 2005080551 A2 | 9/2005 |
| WO | WO 2005/086845 A2 | 9/2005 |
| WO | 2005097977 A2 | 10/2005 |
| WO | 2005097980 A2 | 10/2005 |
| WO | WO2005116073 A2 | 12/2005 |
| WO | 2006020919 A2 | 2/2006 |
| WO | 2006088867 A2 | 2/2006 |
| WO | WO2006016999 A1 | 2/2006 |
| WO | 2006026473 A1 | 3/2006 |
| WO | 2006029197 A1 | 3/2006 |
| WO | 2006036925 A1 | 4/2006 |
| WO | 2006080952 A2 | 8/2006 |
| WO | 2006083782 A2 | 8/2006 |
| WO | 2006100490 A1 | 9/2006 |
| WO | WO2006094286 A2 | 9/2006 |
| WO | 2006108361 A1 | 10/2006 |
| WO | 2006113470 A2 | 10/2006 |
| WO | 2006114098 A2 | 11/2006 |
| WO | 2006126574 A1 | 11/2006 |
| WO | 2006135824 A1 | 12/2006 |
| WO | 2006137787 A1 | 12/2006 |
| WO | 2006138433 A2 | 12/2006 |
| WO | 2007002086 A2 | 1/2007 |
| WO | 2007003525 A2 | 1/2007 |
| WO | 2007012144 A1 | 2/2007 |
| WO | 2007016485 A2 | 2/2007 |
| WO | 2007026353 A2 | 3/2007 |
| WO | WO 2007/030870 A1 | 3/2007 |
| WO | WO2007027157 A1 | 3/2007 |
| WO | 2007047509 A1 | 4/2007 |
| WO | 2007051038 A2 | 5/2007 |
| WO | 2007069666 A1 | 6/2007 |
| WO | WO2007082963 A1 | 7/2007 |
| WO | 2007101130 A2 | 9/2007 |
| WO | WO2007103282 A1 | 9/2007 |
| WO | 2007127472 A2 | 11/2007 |
| WO | 2007143193 A1 | 12/2007 |
| WO | 2007149182 A2 | 12/2007 |
| WO | WO2007139929 A2 | 12/2007 |
| WO | 2008004990 A2 | 1/2008 |
| WO | 2008013664 A1 | 1/2008 |
| WO | 2008015682 A2 | 2/2008 |
| WO | 2008036447 A2 | 3/2008 |
| WO | WO 2008/035110 A1 | 3/2008 |
| WO | 2008048671 A1 | 4/2008 |
| WO | WO2008048647 A1 | 4/2008 |
| WO | 2009096049 A1 | 5/2008 |
| WO | 2008086005 A1 | 7/2008 |
| WO | 2008094597 | 8/2008 |
| WO | 2008102118 A1 | 8/2008 |
| WO | 2009012428 A1 | 1/2009 |
| WO | 2009018453 A1 | 2/2009 |
| WO | 2009027644 A2 | 3/2009 |
| WO | WO2009048675 A1 | 4/2009 |
| WO | 2009061442 A1 | 5/2009 |
| WO | 2009070592 A1 | 6/2009 |
| WO | 2009096902 A1 | 8/2009 |
| WO | 2009101407 A2 | 8/2009 |
| WO | WO 2009/105570 A2 | 8/2009 |
| WO | 2009110215 A1 | 9/2009 |
| WO | 2009131568 A1 | 10/2009 |
| WO | 2009132083 A2 | 10/2009 |
| WO | 2009154606 A1 | 12/2009 |
| WO | 2010000415 A1 | 1/2010 |
| WO | 2010002846 A1 | 1/2010 |
| WO | 2010051213 A1 | 5/2010 |
| WO | 2010051223 A1 | 5/2010 |
| WO | 2010053472 A1 | 5/2010 |
| WO | 2010057039 A2 | 5/2010 |
| WO | 2010059775 A1 | 5/2010 |
| WO | 2011011300 A2 | 1/2011 |
| WO | 2011067465 A1 | 6/2011 |
| WO | 2011108993 A1 | 9/2011 |
| WO | 2011123572 A1 | 10/2011 |
| WO | 2011139628 A1 | 11/2011 |
| WO | 2012019122 A2 | 2/2012 |
| WO | 2012117333 A1 | 9/2012 |
| WO | 2013055397 A1 | 4/2013 |
| WO | 2013055834 A2 | 4/2013 |
| WO | 2013095953 A1 | 6/2013 |
| WO | 2013184888 A1 | 12/2013 |
| WO | 2014033322 A1 | 3/2014 |
| WO | 2014105546 A1 | 7/2014 |
| WO | 2014152321 A1 | 9/2014 |

OTHER PUBLICATIONS

Amit et al., Biol. of Reprod., 70: 837-845, 2004.*
Watanabe et al., 2007, Nat. Biot., vol. 25(6), pp. 681-686.*
Mallon et al. (2006, Int. J. Biochemistry and Cell Biol., vol. 38, pp. 1063-1075).*
Watanabe et al. (2007, Nat. Biot., vol. 25(6), pp. 681-686).*
Yim et al. (2005, J. Biomater. Sci. Polymer Edn., vol. 16(10), pp. 1193-1217).*
Buzzard et al. Nature Biotechnol. 22:381-382, 2004.
Cheon et al. (BioReprod DOI:10.1095/biolreprod.105.046870; Oct. 19, 2005.
Cheon et al BioReprod 77 2007.
Draper et al. Nature Biotechnol. 22:53-54, 2004.
Hasegawa et al. Stem Cells 24:2649-2660, 2006.
Heng et al. Biotechnology and Applied Biochemistry 47:33-37, 2007.
Koyanagi, M et al (J Neurosci Res. Feb. 1, 2008; 86(2): 270-280).
Levenstein et al Stem Cells 24: 568-574, 2006.
Mitalipova et al. Nature Biotechnol. 23:19-20, 2005.
Nicolas et al. Stem Cells Dev. 16:109-118, 2007.
Peerani et al. (EMBO Journal 26:4744-4755, 2007).
Reubinoff et al (Nature Biotechnology 18: 399-404 (2000).
Sidhu et al. Stem Cells Dev. 15:61-69, 2006.
Stojkovic et al. (Stem Cells 23:895-902, 2005).
Thompson et al (Science Nov. 6, 1998: vol. 282. No. 5391, pp. 1145-1147).
Vallier et al. (J. Cell Sci. 118:4495-4509, 2005).
Wanatabe et al. (Nature Biotechnol. 25:681-686, 2007).
Xu et al. (Nature Biotechnology 19:971-974, 2001).
Curr. Top. Dev. Biol. 38:133 ff, 1998.
Proc. Natl. Acad. Sci. USA 92:7844, 1995.
Xu et al. (Stem Cells 22: 972-980, 2004).
D'Amour et al., Nature Biotechnology 23, 1534-1541 (2005).
D'Amour et al., Nature Biotechnology 24, 1392-1401 (2006).
Shinozaki, et al., Development 131, 1651-1662 (2004).
McLean et al., Stem Cells 25, 29-38 (2007).
Shindler M. et al. Biomaterials 26(28): 5624-5631; 2005.

(56) References Cited

OTHER PUBLICATIONS

International Search Report dated Feb. 3, 2010 for Appln. No. PCT/US2009/065067.
Harb Nicole et al.: "The Rho-Rock-Myosin Signaling Axis Determines Cell-Cell Integrity of Self-Renewing Pluripotent Stem Cells" Plos One, Public Library of Science, San Franciso, CA vol. 3, No. 8, Aug. 1, 2008, pp. E3001-1, XP002530386.
Pardo A.M. et al.: Corning TM CellBIND TM Surface: An Improved Surface for Enhanced Cell Attachment (Corning Technical Report 2005) Life Sciences, Pergamon Press, Oxford, GB, Jan. 1, 2005, pp. 1-8, XP0025530385.
Van Kooten T.G. et al.: "Plasma-Treated Polystyrene Surfaces: Model Surfaces for Studying Cell-Biomaterial Interactions" Biomaterials, Elsevier Science Publishers BV., Barking, GB, vol. 25, No. 10, May 1, 2004, pp. 1735-1747, XP004485087.
Abe, et al., Evidence That P13K, Rac, Rho, and Rho Kinase Are Involved in Basic Fibroblast Growth Factor-Stimulated Fibroblast-Collagen Matrix Contraction, Journal of Cellular Biochemistry, 2007, pp. 1290-1299, vol. 102.
Abeyta, et al., Unique Gene Expression Signatures of Independently-Derived Human Embryonic Stem Cells Lines, Human Molecular Genetics, Jan. 28, 2004, pp. 601-608, vol. 13, No. 6, Oxford University Press.
Abranches, et al., Expansion of Mouse Embryonic Stem Cells on Microcarriers, Biotechnology Bioengineering, Apr. 15, 2007, pp. 1211-1221, vol. 96, No. 6, Wiley InterScience.
Ackermann, et al., Molecular Regulation of Pancreatic B-Cell Mass Development, Maintenance, and Expansion, Journal of Molecular Endocrinology, 2007, pp. 193-206, vol. 38.
Adams, J., Proteasome Inhibition in Cancer: Development of PS-341, Seminars in Oncology, 2001, pp. 613-619, vol. 28, No. 6.
Age-Related Eye Disease Study Research Group, A Randomized, Palcebo-Controlled, Clinical Trial of High-Dose Supplementation with Vitamins C and E, Beta Carotene, and Zinc for Age-Related Macular Degeneration and Vision Loss, Arch Ophthalmology, 2001, pp. 1417-1436, AREDS Report No. 8, vol. 119.
Ali, et al., Exploitation of Protein Kinase C: A Useful Target for Cancer Therapy, Cancer Treatment Reviews, 2009, pp. 1-8, vol. 35.
Allegrucci, et al., Differences between Human Embryonic Stem Cell Lines, Human Reproduction Update, Aug. 26, 2006, pp. 1-18, Advance Access.
Almond, et al., The Proteasome: A Novel Target for Cancer Chemotherapy, Leukemia, 2002, pp. 433-443, vol. 16.
Amit et al., Human Feeder Layers for Human Embryonic Stem Cells, Biology of Reproduction, Jan. 22, 2003, 2150-2156, 68, No. 6, Society for the Study of Reproduction, Inc.
Amit, et al., Clonally Derived Human Embryonic Stem Cell Lines Maintain Pluripotency and Proliferative Potential for Prolonged Periods of Culture, Developmental Biology, 2000, pp. 271-278, vol. 227.
Arai, et al., Purification of Recombinant Activin A Using the Second Follistatin Domain of Follistatin-Related Gene (FLRG), Protein Expression & Purification, 2006, pp. 78-82, vol. 49.
Armstrong, et al., The Role of P13K/AKT, MAPK/ERK and NFκβ Signalling in the Maintenance of Human Embryonic Stem Cell Pluripotency and Viability Highlighted by Transcriptional Profiling and Functional Analysis, Human Molecular Genetics, 2006, pp. 1894-1913, vol. 15, No. 11.
Assady, et al., Insulin Production by Human Embryonic Stem Cells, Diabetes, 2001, pp. 1691-1697, vol. 50.
Baetge, Production of B-Cells from Human Embryonic Stem Cells, Diabetes, Obesity, Metabolism, 2008, pp. 186-194, vol. 10, Supplement 4.
Bai, et al., Glucagon-Like Peptide-1 Enhances Production of Insulin in Insulin-Producing cells Derived from Mouse Embryonic Stem Cells, Journal of Endocrinology, 2005, pp. 343-352, vol. 186, No. 2.
Balsam, et al., Haematopoeitic Stem Cells Adopt Mature Haeatopoietic Fates in Ischaemic Myocardium, Nature, Apr. 8, 2004, pp. 668-673, ?, Nature Publishing Group.
Bandyopadhyay, et al., Inhibition of Pulmonary and Skeletal Metastasis by a Transforming Growth Factor-B Type I Receptor Kinase Inhibitor, Cancer Research, 2006, pp. 6714-6721, vol. 66, No. 13.
Barclay, et al., The Leucocyte Antigen Facts Book, The Leucocyte Antigen Facts Book, 1997, Textbook, 2[sup] edition, Academic Press.
Bellinger, et al., Swine Models of Type 2 Diabetes Mellitus: Insulin Resistance, Glucose Tolerance, and Cardiovascular Complications, ILAR Journal, 2006, pp. 243-258, vol. 47, No. 3.
Beltrami, et al., Adult Cardiac Stem Cells are Multipotent and Support Myocardial Regeneration, Cell, Sep. 19, 2003, pp. 763-776, vol. 114, Cell Press.
Bigdeli, et al., Adaptation of Human Embryonic Stem Cells to Feeder-Free and Matrix-Free Culture Conditions Directly on Plastic Surfaces, Journal of Biotechnology, 2008, pp. 146-153, vol. 133.
Blyszczuk et al., Expression of Pax4 in embryonic stem cells promotes differentiation of nestin-positive progenitor and insulin-producing cells, Proceedings of the National Academy of Sciences, Feb. 4, 2003, 998-1003, 100-3, National Academy of Sciences.
Bocian-Sobkowska, et al., Polyhormonal Aspect of the Endocrine Cells of the Human Fetal Pancreas, Histochem Cell Biol, 1999, pp. 147-153, vol. 112, Issue 2.
Bonner-Weir et al., In vitro cultivation of human islets from expanded ductal tissue, Proceedings of the National Academy of Sciences, Jul. 5, 2000, 7999-8004, 97-14, National Academy of Sciences.
Borowiak, et al., How to Make AB Cells, Current Opinion Cell Biology, 2009, pp. 727-732, vol. 21, Issue 6.
Borowitz, et al., Prognostic Significance of Fluorescence Intensity of Surface Marker . . . , Blood, Jun. 1, 1997, 3960-3966, 89-11, American Society of Hematology, Washington, D.C., US.
Braam, et al., Improved Genetic Manipulation of Human Embryonic Stem Cells, Nature Methods, May 2008, pp. 389-392, vol. 5, No. 5.
Brakenhoff et al., Development of a Human Interleukin-6 Receptor Antagonist, Journal of Biological Chemistry, Jan. 7, 1994, 86-93, 269-1, US.
Brambrink, et al., Sequential Expression of Pluripotency Markers During Direct Reprogramming of Mouse Somatic Cells, Cell Stem Cell, 2008, pp. 151-159, vol. 2.
Brevig, et al., The Recognition of Adsorbed and Denatured Proteins of Different Topographies by β2 Integrins and Effects on Leukocyte Adhesion and Activation, Biomaterials, 2005, pp. 3039-3053, vol. 26.
Brevini et al, Embryonic Stem Cells in Domestic Animals, Embryonic Stem Cells in Domestic Animals, 2010, 544-550, 74.
Brevini, et al., No Shortcuts to Pig Embryonic Stem Cells, Theriogenology, 2010, pp. 544-550, vol. 74.
Bross, et al., Approval Summary for Bortezomib for Injection in the Treatment of Multiple Myeloma, Clinical Cancer Research, Jun. 15, 2004, pp. 3954-3964, vol. 10.
Brown, et al., Optimal Control of Blood Glucose: The Diabetic Patient or the Machine?, Science Translation Medicine, Apr. 14, 2010, pp. 1-5, vol. 2 Issue 27.
Burkard et al, Conditional Neuronal Nitric Oxide Synthase Overexpression Impairs Myocardial Contractility, Circulation Reseach, Jan. 18, 2007, pp. e32-e44, vol. 100.
Cai, et al., Generation of Homogeneous PDX1+Pancreatic Progenitors from Human ES Cell-derived Endoderm Cells, Journal of Molecular Cell Biology, Nov. 12, 2009, pp. 50-60, vol. 2.
Castaing, et al., Blood Glucose Normalization Upon Transplantation of Human Embryonic Pancreas into Beta-Cell-Deficient SCID Mice, Diabetologica, 2001, pp. 2066-2076, vol. 44.
Chambers, et al., Functional Expression Cloning of Nanog, a Pluripotency Sustaining Factor in Embryonic Stem Cells, Cell, May 30, 2003, pp. 643-655, vol. 113.
Chapple, et al., Unfolding Retinal Dystrophies: A Role for Molecular Chaperones?, Trends in Molecluar Medicine, 2001, pp. 414-421, vol. 7, No. 9.
Chen, et al., A Small Molecule that Directs Differentiation of Human ESCs into the Pancreatic Lineage, Nature Chemical Biology, Apr. 11, 2009, pp. 258-265, vol. 5, No. 4.

(56) References Cited

OTHER PUBLICATIONS

Chen, et al., Chemically Defined Conditions for Human iPSC Derivation and Culture, Nature Methods, 2011, pp. 424-429, vol. 8, Issue 5.
Chen, et al., Differentiation of Embryonic Stem Cells Towards Pancreatic Progenitor Cells and their Transplantation into Strepozotocin-Induced Diabetic Mice, Cell Biology International, 2008, pp. 456-461, vol. 32.
Chen, et al., Differentiation of Rat Marrow Mesencymal Stem Cells in Pancreatic Islet Beta-Cells, World Journal of Gastroenterology, Oct. 15, 2004, 3016-3020, 10.
Chen, et al., Retinoic Acid Signaling is Essential for Pancreas Development and Promotes Endocrine at the Expense of Exocrine Cell Differentiation in Xenopus, Developmental Biology, 2004, pp. 144-160, vol. 271.
Choi, et al., In Vitro Trans-Differentiation of Rat Mesenchymal Cells into Insulin-Producing Cells by Rat Pancreatic Extract, Biochemical and Biophysical ResearchCommunications, 2005, pp. 1299-1305, vol. 330.
Chung, et al., Human Embryonic Stem Cell Lines Generated without Embryo Destruction, Cell Stem Cell, 2008, pp. 113-117, vol. 2.
Corbeil, et al., Rat Prominin, Like its Mouse and Human Orthologues, is a Pentaspan Membrane Glycoprotein, Biochemical and Biophysical Research Communications, 2001, pp. 939-944, vol. 285, No. 4.
Crane, et al., An Embryogenic Model to Explain Cytogenetic Inconsistencies Observed in Chorionic Villus Versus Fetal Tissue, Prenatal Diagnosis, 1988, pp. 119-129, vol. 8.
Cresta, et al., Phase I Study of Bortezomib with Weekly Paclitaxel in Patients with Advanced Solid Tumours, European Journal of Cancer, 2008, pp. 1829-1834, vol. 44.
Cure, et al., Improved Metabolic Control and Quality of Life in Seven Patients with Type 1 Diabetes Following Islet After Kidney Transplantation, Cell Therapy and Islet Transplantation, Mar. 27, 2008, pp. 801-812, vol. 85, No. 6.
D'Amour et al., Production of pancreatic hormone, Production of pancreatic hormone, 2006, 1392-1401, 24.
Damy, et al., Increased Neuronal Nitric Oxide Synthase-Derived NO Production in the Failing Human Heart, Research Letters, Apr. 24, 2004, pp. 1365-1367, vol. 363.
David M. Chacko, et al., Survival and Differentiation of Cultured Retinal Progenitors Transplanted in the Subretinal Space of the Rat, Biochemical and Biophysical Research Communications, 2000, pp. 842-846, vol. 268, Academic Press.
De Coppi, et al., Isolation of Amniotic Stem Cell Lines with Potential for Therapy, Nature Biotechnology, 2007, pp. 100-106, vol. 25, No. 1.
De Rosa, 11-color, 13-parameter flow cytometry: Identification of . . . , Nature, Feb. 1, 2001, 245-248, 7-2, Nature Publishing Group, US.
Dekker, et al., Adhesion of Endothelial Cells and Adsorption of Serum Proteins on Gas Plasma-Treated Polytetrafluoroethylene, Biomaterials, 1991, pp. 130-138, vol. 12.
Denning, et al., Common Culture Conditions for Maintenance and Cardiomyocyte Differentiation of the Human Embryonic Stem Cell Lines, BG01 and HUES-7, Int. J. Del. Biol., 2006, pp. 27-37, vol. 50.
Donovan, et al., The End of the Beginning for Pluripotent Stem Cells, Nature, Nov. 2001, pp. 92-97, vol. 414.
Dorrell, et al., Editorial, Stem Cell Research, 2008, pp. 155-156, vol. 1.
Doyle, et al., Cell and Tissue Culture: Laboratory Procedures in Biotechnology, Cell and Tiossue Culture: Laboratory Procedures in Biotechnology, 1995, Textbook, Textbook, Wiley.
Draper, et al., Surface Antigens of Human Embryonic Stem Cells: Changes Upon Differentiation in Culture, Journal Anatomy, 2002, pp. 249-258, vol. 200, Anatomical Society of Great Britain and Ireland.
Dufour, et al., Development of an Ectopic Site for Islet Transplantation Using Biodegradable Scaffolds, Tissue Engineering, 2005, pp. 1323-1331, vol. 11, No. 9/10.
Dupont-Gillain, et al., Plasma-Oxidized Polystyrene: Wetting Properties and Surface Reconstruction, Langmuir, 2000, pp. 8194-8200, vol. 16.
Edlund, Pancreatic Organogenisis—Pancreatic Mechanisims and Implications for Therapy, Nature, Jul. 1, 2002, 524-532, 3, Nature Publishing Group, US.
Ellerstrom, et al., Derivation of a Xeno-Free Human Embryonic Stem Cell Line, Stem Cells, 2006, pp. 2170-2176, vol. 24.
Ellerstrom, et al., Facilitated Expansion of Human Embryonic Stem Cells by Single-Cell Enzymatic Dissociation, Stem Cells, 2007, pp. 1690-1696, vol. 25, No. 7.
Ellmers, et al., Transforming Growth Factor-B Blockade Down-Regulates the Renin-Angiotensin System and Modifies Cardiac Remodling after Myoardial Infarction, Endocrinology, Jul. 24, 2008, pp. 5828-5834, vol. 149—Issue 11, The Endocrine Society.
Enzmann, et al., Enhanced Induction of RPE Lineage Markers in Pluripootent Neural Stem Cells Engrafted into the Adult Rat Subretinal Space, Ophthamology & Visual Science, Dec. 2003, pp. 5417-5422, vol. 44, No. 12, Association for Research in Vision and Ophthamology.
Eventov-Friedman, et al., Embryonic Pig Pancreatic Tissue Transplantation for the Treatment of Diabetes, PLoS Medicine, Jul. 2006, e215, pp. 1165-1177, vol. 3, Issue 7.
Ezashi, et al., Low O2 Tensions and the Prevention of Differentiation of hES Cells, Proceedings of the National Academy of Sciences of USA, Mar. 29, 2005, pp. 4783-4788, vol. 102, No. 13.
Fauza, Amniotic Fluid and Placental Stem Cells, Ballieres Best Practice and Research Clinical Obsterics and Gynaecology, 2004, pp. 877-891, vol. 18, No. 6.
Fidler et al., Selective Immunomodulation by the Antineoplastic Agent Mitoxantrone, Journal of Immunology, Jul. 15, 1986, 727-732, 137-2, American Society of Immunologists, US.
Fischer, et al., Residues in the C-Terminal Region of Activin A Determine Specificity for Follistatin and Type II Receptor Binding, Journal of Endocrinology, 2003, pp. 61-68, vol. 176, Society for Endocrinology.
Florio, et al., Activin A Stimulates Insulin Secretion in Cultured Human Pancreatic Islets, J. Endocrinol. Invest., 2000, pp. 231-234, vol. 23.
Fok, et al., Shear-Controlled Single-Step Mouse Embryonic Stem Cell Expansion and Embryoid Body-Based Differentiation, Stem Cells, 2005, pp. 1333-1342, vol. 23.
Foster, et al., Differentiation of Transplanted Microencapsulated Fetal Pancreatic Cells, Experimental Transplantation, Jun. 15, 2007, pp. 1440-1448, vol. 83, No. 11.
Frandsen et al., Activin B mediated induction of Pdx1 in human embryonic stemcell derived embryoid bodies, Biochemical and Biophysical Research Communications, Aug. 15, 2007, 568-574, 362, Elsevier Inc.
Frigui, et al., A Robust Competitive Clustering Algorithm With Applications in Computer Vision, IEEE Transactions on Pattern Analysis and Machine Intelligence, May 1, 1999, pp. 450-465, vol. 21, No. 5, IEEE, US.
Fung, et al., The Effect of Medical Therapy and Islet Cell Transplantation on Diabetic Nephropathy: An Interim Report, Transplantation, Jul. 15, 2007, pp. 17-22, vol. 84, No. 1.
Gadue, et al., Wnt and TGB-B Signaling Are Required for the Induction of an in vitro Model of Primitive Streak Formation Using Embryonic Stem Cells, Proceedings of the National Academy of Sciences, Nov. 7, 2006, 16806-16811, 103-45, National Academy of Sciences, US.
Gaspar, et al., Inhibition of Transforming Growth Factor Signaling Reduces Pancreatic Adenocarcinoma Growth and Invasiveness, Molecular Pharmacology, 2007, pp. 152-161, vol. 72, Issue 1.
Gellibert, et al., Identification of 1,5-Naphthyridine Derivatives as a Novel Series of Potent and Selective TGF-B Type I Receptor Inhibitor, J. Med. Chem, 2004, pp. 4494-4506, vol. 47, No. 18.
Gershengorn et al., Epithelial-to-Mesenchymal Transition Generates Proliferative Human Islet Precursor Cells, Science, Dec. 24, 2004, 2261-2264, 306, US.

(56) References Cited

OTHER PUBLICATIONS

Giltaire, et al., The CYP26 Inhibitor R115866 Potentiates the Effects of All-Trans Retinoic Acid on Cultured Human Epidermal Keratinocytes, British Journal of Dermatology, 2009, pp. 505-513, vol. 160.
Ginis, et al., Differences Between Human and Mouse Embryonic Stem Cells, Developmental Biology, 2004, pp. 360-380, vol. 269.
Gittest, Developmental Biology of the Pancreas: A comprehensive Review, Developmental Biology, 2009, pp. 4-35, vol. 326, No. 1.
Gosden, et al., Amniotic Fluid Cell Types and Culture, British Medical Bulletin, 1983, pp. 348-354, vol. 39, No. 4.
Graham, et al., Characteristics of a Human Cell Line Transformed by DNA from Human Adenovirus Type 5, Journal General Virology, 1977, pp. 59-72, vol. 36.
Gregg Duester, Retionoic Acid Synthesis and Signaling During Early Organogenesis, Cell, 2008, pp. 921-931, vol. 134.
Guo, et al., Stem Cells to Pancreatic B-Cells: New Sources for Diabetes Cell Therapy, Endocrine Reviews, May 2009, pp. 214-227, vol. 30, No. 3, The Endocrine Society.
Hadley, et al., Extracellular Matrix Regulates Sertoli Cell Differentiation, Testicular Cord Formation, and Germ Cell Development In Vitro, The Journal of Cell Biology, Oct. 1985, 1511-1522, 101, Rockefeller University Press.
Hainsworth, et al., Retinal Capillar Basement Membrane Thickening in a Porcine Model of Diabetes Mellitus, Comp Med, 2002, pp. 523-529, vol. 52.
Hamann, et al., Phenotypic and Functional Separation of Memory and and Effector Human CD8+ T Cells, Journal of Experimental Medicine, Mar. 11, 1997, 1407-1418, 186-9, Rockefeller University Press, US.
Haruta, et al., In Vitro and In Vivo Characterization of Pigment Epithelieal Cells Differentiated from Primate Embryonic Stem Cells, Investigative Ophthalmology & Visual Science, Mar. 2004, pp. 1020-1025, vol. 45, No. 3, Association for Research in Vision and Ophthalmology.
Hashemi, et al., A Placebo Controlled, Dose-Ranging, Safety Study of Allogenic Mesenchymal Stem Cells Injected by Endomyocardial Delivery after an Acute Myocardial Infarction, European Heart Journal, Dec. 11, 2007, pp. 251-259, vol. 29.
Heinis, et al., HIF1a and Pancreatic Beta-Cell Development, The FASEB Journal, 2012, pp. 2734-2742, vol. 26.
Heinis, et al., Oxygen Tension Regulates Pancreatic Beta-Cell Differentiation Through Hypoxia-Inducible Factor 1x, Diabetes, 2010, pp. 662-669, vol. 59.
Heit, et al., Embryonic Stem Cells and Islet Replacement in Diabetes Mellitus, Pediatric Diabetes, 2004, pp. 5-15, vol. 5.
Held, et al., The Effect of Oxygen Tension on Colony Formation and Cell Proliferation of Amniotic Fluid Cells In-Vitro, Prenatal Diagnosis, 1984, pp. 171-180, vol. 4, No. 3.
Henderson, et al., Preimplantation Human Embryos and Embryonic Stem Cells Show Comparable Expression of Stage-Specific Embryonic Antigens, Stem Cells, 2002, pp. 329-337, vol. 20.
Heremans, et al., Recapitulation of Embryonic Neuroendocrine Differentiation in Adult Human Pancreatic Duct Cells Expressing Neurogenin 3, The Journal of Cell Biology, 2002, pp. 303-311, vol. 159.
Herrera, Adult-Insulin-and Glucagon-Producing Cells Differentiate from Two Independent Cell Lineages, Development, 2000, pp. 2317-2322 vol. 127, No. 11.
Herzenberg, et al., Fluorescence-activated Cell Sorting, Scientific American, 1976, 108-117, 234, Scientific American, US.
Hess, et al., Bone Marrow-Derived Stem Cells Initiate Pancreatic Regeneration, Nature Biotechnology, Jul. 2003, pp. 763-770, vol. 21, No. 7.
Ho, et al., Animal Cell Bioreactors, Animal Cell Bioreactors, 1991, 1-512, Hardcover, Butterworth-Heinemann.
Hoehn, et al., Morphological and Biochemical Heterogeneity of Amniotic Fluid Cells in Culture, Methods in Cell Biology, 1982, pp. 11-34, vol. 26, Academic Press, Inc.
Hoffman, et al., Characterization and Culture of Human Embryonic Stem Cells, Nature Biotechnology, 2005, pp. 699-708, vol. 23, No. 6.
Hori, et al., Growth inhibitors promote differentiation of insulin-producing tissue from embryonic stem cells, Proceedings of the National Academy of Sciences, Dec. 10, 2002, 16105-16110, 99-25, National Academy of Sciences.
Hosoya, et al., Induction of Differentiation of Undifferentiated Cells into Pancreatic Beta-Cells in Vertebrates, Int. J. Dev. Biol., 2012, pp. 313-323, vol. 56.
Hussain, et al., Stem-Cell Therapy for Diabetes Mellitus, Lancet, 2004, pp. 203-205, vol. 364.
Ianus, et al., In Vivo Derivation of Glucose-Competent Pancreatic Endocrine Cells from Bone Marrow Without Evidence of Cell Fusion, The Journal of Clinical Investigation, Mar. 2003, pp. 843-850, vol. 111, No. 6.
Inami, et al., Differentiation of Induced Pluripotent Stem Cells to Thymic Epithelial Cells by Phenotype, Immunology and Cell Biology, Jun. 24, 2010, pp. 1-8, doi:10.1038/icb.2010.96.
Inman, et al., SB-431542 is a Potent and Specific Inhibitor of Transforming Growth Factor-B Superfamily Type I Activing Receptor-Like Kinase (ALK) Receptors ALK4, ALK5, and ALK7, Molecular Pharmacology, 2002, pp. 65-74, vol. 62, No. 1.
In'T Anker, et al., Amniotic Fluid as a Novel Source of Mesenchymal Stem Cells for Therapeutic Transplantation, Blood, Aug. 15, 2003, pp. 1548-1549, vol. 102, No. 4.
Inzunza, et al., Derivation of Human Embryonic Stem Cell Lines in Serum Replacement Medium Using Postnatal Human Fibroblasts as Feeder Cells, Stem Cells, 2005, 544-549, 23, AlphaMed Press.
Jafary, et al., Differential effect of activin on mouse embryonic stem cell differentiation in insulin-secreting cells under nestin-positive selection and spontaneous differentiation protocols, Cell Biology International, 2008, 278-286, 32, Elsevier.
Jeon, et al., Endocrine Cell Clustering During Human Pancreas Development, J Histochem Cytochem, 2009, pp. 811-824, vol. 57, Issue 9.
Jiang, et al., Generation of Insulin-Producing Islet-Like Clusters from Human Embryonic Stem Cells, Stem Cells, 2007, pp. 1940-1953, vol. 25, Issue 8.
Johansson, et al., Temporal Control of Neurogenin3 Activity in Pancreas Progenitors Reveals Competence Windows for the Generation of Different Endocrine Cell Types, Developmental Cell, Mar. 2007, pp. 457-465, vol. 12.
Kahan, Pancreatic Precursors and Differentiated Islet Cell Types from Murine Embryonic Stem Cells, Diabetes, Aug. 2003, pp. 2016-2042, vol. 52.
Karvonen, et al., Incidene of Childhood Type 1 Diabetes Worldwide, Diabetes Care, 2000, pp. 1516-1526, vol. 23, No. 10.
Kelly, et al., Cell-Surface Markers for the Isolation of Pancreatic Cell Types Derived from Human Embryonic Stem Cells, Nature Biotechnology, 2011, pp. 750-756, vol. 29, Issue 8.
Kicic, et al., Differentiation of Marrow Stromal Cells into Photoreceptors in the Rat Eye, The Journal of Neuroscience, Aug. 27, 2003, pp. 7742-7749, vol. 23, Issue 21.
Kingsley, The TGF-B Superfamily: New Members, New Receptors, and New Genetic Tests of Function in Different Organisms, Genes & Development, 1994, pp. 133-146, vol. 8, Cold Spring Harbor Laboratory Press.
Kinkel, et al., Cyp26 Enzymes Function in Endoderm to Regulate Pancreatic Field Size, PNAS, May 12, 2009, pp. 7864-7869, vol. 106, No. 19.
Kleinman et al., Basement Membrane Complexes with Biological Activity, Biochemistry, 1986, 312-318, 25, American Chemical Society.
Klimanskaya, et al., Human Embryonic Stem Cells Derived without Feeder Cells, Lancet, May 2005, pp. 1636-1641, vol. 365, No. 9471.
Koblas, et al., Differentiation of CD133-Positive Pancreatic Cells Into Insulin-Producing Islet-Like Cell Clusters, Transplantation Proceedings, 2008, pp. 415-418, vol. 40.
Koller, et al., Effects of Synergistic Cytokine Combinations, Low Oxygen, and Irradiated Stroma on the Expansion of Human Cord Blood Progenitors, Blood, Jul. 15, 1992, pp. 403-411, vol. 80, No. 2.

(56) References Cited

OTHER PUBLICATIONS

Konstantinova, et al., EphA-Ephrin-A-Mediated Beta Cell Communication Regulates Insulin Secretion from Pancreatic Islets, Cell, Apr. 20, 2007, pp. 359-370, vol. 129.

Kozikowski, et al., New Amide-Bearing Benzolactam-Based Protein Kinase C Modulators Induce Enhanced Secretion of the Amyloid Precuros Protein Metabolite sAPPa, J. Med. Chem., 2003, pp. 364-373, vol. 46, No. 3.

Krapcho et al., Synthesis and Antineoplastic Evaluations of 5,8-Bis[(aminoalkyl)amino]-1-azaanthracene-9,10-diones, Journal of Medical Chemistry, 1985, 1124-1126, 28, American Chemical Society.

Krawetz, et al., Human Embryonic Stem Cells: Caught Between a ROCK Inhibitor and a Hard Place, BioEssays: News and Reviews in Molecular Cellular and Developmental Biology, 2009, pp. 336-343, vol. 31.

Kron, et al., Expression of Human Activin C Protein in Insect Larvae Infected with a Recombinant Baculovirus, Journal of Virological Methods, 1998, pp. 9-14, vol. 72.

Kroon, et al., Pancreatic Endoderm Derived from Human Embryonic Stem Cells Generates Glucose-Responsive Insulin-Secreting Cells in vivo, Nature Biotechnology, Apr. 2008, pp. 443-452, vol. 26, No. 4.

Krutzik, et al., Coordinate Analysis of Murine Immune Cell Surface Markers and Intracellular Phosphoproteins by Flow Cytometry, Journal of Immunology, May 30, 2005, 2357-2365, 175, American Association of Immunologists, Inc., US.

Ku et al., Committing Embryonic Stem Cells to Early Endocrine Pancreas In Vitro, Stem Cells, 2004, 1205-1217, 22, AlphaMed Press.

Kurihara-Bergstrom, et al., Characterization of the Yucatan Miniature Pig Skin and Small Intestine for Pharmaceutical Applications, Laboratory Animal Science, 1986, pp. 396-399, vol. 36, No. 4.

Laplante, et al., RhoA/ROCK and Cdc42 Regulate Cell-Cell Contact and N-Cadherin Protein Level During Neurodetermination of P19 Embryonal Stem Cells, Journal of Neurobiology, 2004, pp. 289-307, vol. 60, No. 3.

Larsen, et al., Evaluation of B-Cell Mass and Function in the Gottingen Minipig, Diabetes, Obesity and Metabolism, 2007, pp. 170-179, vol. 9, Supplement 2, Blackwell Publishing Ltd.

Larsen, et al., Use of the Gootingen Minipig as a Model of Diabetes, with Special Focus on Type 1 Diabetes Research, ILAR Journal, 2004, pp. 303-313, vol. 45, No. 3.

Lavon et al., The Effect of Overexpression of Pdx1 and Foxa2 on the Differentiation of Human Embryonic Stem Cells into Pancreatic Cells, Stem Cells, 2006, 1923-1930, 24, Alpha Med Press, IL.

Le Blanc, et al., Mesenchymal Stem Cells Inhibit and Stimulate Mixed Lymphocyte Cultures and Mitogenic Responses Independently of the Major Histocompatibility Complex, Scandinavian Journal of Immunology, 2003, pp. 11-20, vol. 57, Blackwell Publishing Ltd.

Lee et al., Establishment and Maintenance of Human Embryonic Stem Cell Lines on Human Feeder Cells Derived from Uterine Endometrium under Serum-Free Condition, Biology of Reproduction, Aug. 18, 2004, 42-49, 72.

Lee, et al., Human B-cell Precursors Mature into Functional Insulin-Producing Cells in an Immunoisolation Device: Implications for Diabetes Cell Therapies, Transplantation, Apr. 15, 2009, pp. 983-991, vol. 87, No. 7.

Lee, et al., PKC-gamma Inhibitors Sustain Self-Renewal of Mouse Embryonic Stem Cells Under Hypoxia in Vitro, Experimental and Molecular Medicine, Apr. 2010, pp. 294-301, vol. 43, No. 4.

Lee, et al., Protein Kinase A- and C-Induced Insulin Release from Ca2+-Insensitive Pools, Cellular Signalling, 2003, pp. 529-537, vol. 15.

Lee, et al., Retionic Acid-Induced Human Secretin Gene Expression in Neuronal Cells is Mediated by Cyclin-Dependent Kinase 1, Annals of the New York Academy of Sciences, 2006, pp. 393-398, vol. 1070.

Leon-Quinto, et al., In Vitro Directed Differentiation of Mouse Embryonic Stem Cells into Insulin-Producing Cells, Diabetologia, 2004, pp. 1442-1451, vol. 47, No. 8.

Li, et al., Generation of Rat and Human Induced Pluripotent Stem Cells by Combining Genetic Reprogramming and Chemical Inhibitors, Cell Stem Cell, Jan. 9, 2009, pp. 16-19, vol. 4.

Li, et al., Pluripotency Can be Rapidly and Efficiently Induced in Human Amniotic Fluid-Derived Cells, Human Molecular Genetics, 2009, pp. 4340-4349, vol. 18, No. 22.

Lilja et al., Cyclin-dependent Kinase 5 Promotes Insulin Exocytosis, Journal of Biological Chemistry, Jul. 6, 2001, 34199-34205, 36-7, JBC Papers in Press.

Liu, et al., A Novel Chemical-Defined Medium with bFGF and N2B27 Supplements Supports Undifferentiated Growth in Human Embryonic Stem Cells, Biochemical and Biophysical Research Communications, 2006, pp. 131-139, vol. 346.

Loh, et al., Genomic Approaches to Deconstruct Puripotency, Annu Rev Genomics Hum Genet, 2011, pp. 165-185, vol. 12.

Lumelsky, et al., Differentiation of Embryonic Stem Cells to Insulin-Secreting Structures Similar to Pancreatic Islets, Science, 2001, 1389-1394, 292, HighWire Press.

Lund, et al., Cell Transplantation as a Treatment for Retinal Disease, Progress in Retinal and Eye Research, 2001, pp. 415-449, vol. 20, No. 4, Elsevier Science Ltd.

Lund, et al., Retinal Transplantation: Progress and Problems in Clinical Application, Journal of Leukocyte Biology, Aug. 2003, pp. 151-160, vol. 74.

Lyttle, et al., Transcription Factor Expression in the Developing Human Fetal Endocrine Pancreas, Diabetologica, 2008, pp. 1169-1180, vol. 51, Spring-Verlag.

MacFarlane, et al., Glucose Stimulates Translocation of the Homeodomain Transcription Factor PDX1 from the Cytoplasm to the Nucleus in Pancreatic B-Cells, The Journal of Biological Chemistry, 1999, pp. 1011-1016, vol. 274, No. 2.

Maherali, et al., Directly Reprogrammed Fibroblasts Show Global Epigenetic Remodeling and Widespread Tissue Contribution, Cell Stem Cell, Jul. 2007, pp. 55-70, vol. 1, Elsevier, Inc.

Mao, et al., The Reversal of Hyperglycaemia in Diabetic Mice Using PLGA Scaffolds Seeded with Islet-like Cells Derived from Human Embyonica Stem Cells, Biomaterials, 2009, pp. 1706-1714, vol. 30.

Marshall, et al., Early Micro-and Macro-Angiopathy in the Streptozotocin, Research in Experimental Medicine, 1980, pp. 145-158, vol. 177, Springer-Verlag.

Marshall, et al., Isolation and Maintenance of Primate Embryonic Stem Cells, Methods in Molecular Biology, 2001, pp. 11-18, vol. 158.

Martin, et al., Bioreactors for Tissue Mass Culture: Design, Characterization, and Recent Advances, Biomaterials, Jul. 14, 2005, pp. 7481-7503, vol. 26.

Marzo, et al., Pancreatic Islets from Cyclin-Dependent Kinase 4/R24C (Cdk4) Knockin Mice have Significantly Increased Beta Cell Mass and are Physiologically Functional, Indicating that Cdk4 is a Potential Target for Pancreatic . . . , Diabetologia, 2004, pp. 686-694, vol. 47.

Mathis, et al., B-Cell Death During Progression to Diabetes, Nature, 2001, pp. 792-798, vol. 414.

Matveyenko, et al., Inconsistent Formation and Nonfunction of Insulin-Positive Cells from Pancreatic Endoderm Derived from Human Embyonic Stem Cells in Athymic Nude Rats, American Journal of Physiol Endocrinol Metab, 2010, pp. E713-E720, vol. 299.

McKiernan, et al., Directed Differentiation of Mouse Embryonic Stem Cells into Pancreatic-Like or Neuronal-and Glial-Like Phenotypes, Tissue Engineering, 2007, pp. 2419-2430, vol. 13, No. 10.

McLin, et al., Repression of WNT/(szligbeta)-6atenin Signaling in the Anterior Endoderm is Essential for Liver and Pancreas Development, Development, 2007, pp. 2207-2217, vol. 134, Issue 12.

Meijer, et al., Pharmacological Inhibitors of Glycogen Synthase Kinase 3, Trends in Pharmacological Sciences, Sep. 2004, pp. 471-480, vol. 25, No. 9.

(56) References Cited

OTHER PUBLICATIONS

Micallef et al., Retinoic Acid Induces Pdx1-Positive Endoderm in Differentiating Mouse Embryonic Stem Cells, Diabetes, Feb. 2005, 301-305, 54, American Diabetes Association.
Miller, et al., The Pig as a Model for Human Nutrition, Annual Review of Nutrition, 1987, pp. 361-382, vol. 7, Annual Reviews Inc.
Milunsky, et al., Genetic Disorders and the Fetus: Diagnosis Prevention and Treatment, Pediatric and Developmental Pathology, 2011, pp. 84, vol. 14, Society for Pediatric Pathology.
Mitsui, et al., The Homeoprotein Nanog is Required for Maintenance of Pluripotency in Mouse Epiblast and ES Cells, Cell, May 30, 2003, pp. 631-642, vol. 113, Cell Press.
Miyamoto et al., Human Placenta Feeder Layers Support Undifferentiated Growth of Primate Embryonic Stem Cells, Stem Cells, 2004, 433-440, 22, AlphaMed Press.
Miyazaki et al., Regulated Expression of pdx-1 Promotes In Vitro Differentiation of Insulin-Producing Cells From Embryonic Stem Cells, Diabetes, Apr. 2004, 1030-1037, 53, American Diabetes Association.
Moran, et al., Bidirectional-Barbed Sutured Knotless Running Anastomosis v Classic van Velthoven in a Model System, Journal of Endourology, 2007, pp. 1175-1177, vol. 21, No. 10.
Morrison, et al., Culture in Reduced Levels of Oxygen Promotes Clonogenic Sympathoadrenal Differentiation by Isolated Neural Crest Stem Cells, Journal of Neuroscience, Oct. 1, 2000, pp. 7370-7376, vol. 20, No. 19.
Movassat, et al., Keratinocyte Growth Factor and Beta-Cell Differentiation in Human Fetal Pancreatic Endocrine Precursor Cells, Diabetologia, 2003, pp. 822-829, vol. 46.
Muchamuel, et al., Preclinical Pharmacology and in Vitro Characterization of PR-047, An Oral Inhibitor of the 20s Proteasome, Blood, Nov. 16, 2008, p. 1257, vol. 112, No. 11.
Munoz, et al., Conventional Pluripotency Markers are Unspecific for Bovine Embryonic-Derived Cell-Lines, Theriogenology, 2008, pp. 1159-1164, vol. 69.
Murtha, et al., Evaluation of a Novel Technique for Wound Closure Using a Barbed Suture, Cosmetic, Aug. 2, 2005, pp. 1769-1780, vol. 117, No. 6.
Nakagawa, et al., Generation of Induced Pluripotent Stem Cells without Myc from Mouse and Human Fibroblasts, Generation of Induced Pluripotent Stem Cells without Myc from Mouse and Human Fibroblasts, Jan. 2008, pp. 101-106, vol. 26, No. 1.
Nakamura, et al., Ocular Surface Reconstruction Using Cultivated Mucosal Epithelial Stem Cells, Cornea, Oct. 2003, S75-S80, vol. 22, Supplement 1.
Nelson, et al., The Transcription Factors Nkx6.1 and Nkx6.2 Possess Equivalent Activities in Promoting Beta-Cell Fate Specification in Pdx1+ Pancreatic Progenitor Cells, Development, 2007, pp. 2491-2500, vol. 134.
Nishimura, et al., Expression of MafA in Pancreatic Progenitors is Detrimental for Pancreatic Development, Developmental Biology, 2009, pp. 108-120, vol. 333.
Nostro, et al., Stage-Specific Signaling Through TGF Family Members and WNT Regulates Patterning and Pancreatic Specification of Human Pluripotent Stem Cells, Development, 2011, pp. 861-871, vol. 138, Issue 5.
Odom, et al., Control of Pancreas and Liver Gene Expression by HNF Transcription Factors, Science, 2004, pp. 1378-1381, vol. 303, No. 5662.
Okita, et al., Generation of Germline-Competent Induced Pluripotent Stem Cells, Nature, Jul. 19, 2007, pp. 313-317, vol. 448.
Orlowski, et al., Safety and Antitumor Efficacy of the Proteasome Inhibitor Carfilzomib (PR-171) Dosed for Five Consecutive Days in Hematologic Malignancies: Phase 1 Results, Blood, 2007, Part 1, vol. 110, No. 11.
Osborne, et al., Some Current Ideas on the Pathogenesis and the Role of Neuroprotection in Glaucomatous Optic Neuropathy, European Journal of Ophthalmology, 2003, S19-S26, vol. 13, Supplement 3, Wichtig Editore.
Ostrom, et al., Retinoic Acid Promotes the Generation of Pancreatic Endocrine Progenitor Cells and Their Further Differentiation into B-Cells, PLOS One, Jul. 30, 2008, e2841, pp. 1-7, vol. 3, No. 7.
Ouziel-Yahalom, et al., Expansion and Redifferentiation of Adult Human Pancreatic islet Cells, Biochemical and Biophysical Research Communications, 2006, pp. 291-298, vol. 341.
Paling, et al., Regulation of Embryonic Stem Cell, Self-Renewal by Phosphoinositide 3-kinase-dependent Signaling, Journal of Biological Chemistry, 2004, pp. 48063-48070, vol. 279, No. 46.
Panchision, et al., Optimized Flow Cytometric Analysis of Central Nervous System Tissue Reveals Novel Functional Relationships Among Cells Expressing CD133, CD15, and CD24, Stem Cells, 2007, pp. 1560-1570, vol. 25.
Panepinto, et al., The Yucatan Miniature Pig: Characterization and Utilization in Biomedical Research, Laboratory Animal Science, Aug. 1986, pp. 344-347, vol. 36, No. 4, American Association for Laboratory Animal Science.
Pangas, et al., Production and Purification of Recombinant Human Inhibin and Activin, Journal of Endocrinology, 2002, pp. 199-210, vol. 172.
Paris, et al., Equine Embryos and Embryonic Stem Cells: Defining Reliable Markers of Pluripotency, Theriogeneology, 2010, pp. 516-524, vol. 74.
Perrier, et al., Derivation of Midbrain Dopamine Neurons from Human Embryonic Stem Cells, PNAS, Aug. 24, 2004, pp. 12543-12548, vol. 101, No. 34.
Phillips, et al., Attachment and Growth of Human Embryonic Stem Cells on Microcarriers, Journal of Biotechnology, 2008, pp. 24-32, vol. 138.
Phillips, et al., Directed Differentiation of Human Embryonic Stem Cells into the Pancreatic Endocrine Lineage, Stem Cells and Development, 2007, pp. 561-578, vol. 16, No. 4.
Pouton, et al., Embryonic Stem Cells as a Source of Models for Drug Discovery, Nature Reviews Drug Discovery, Aug. 2007, pp. 1474-1776, vol. 6, No. 8.
Prichard, et al., Adult Adipose Derived Stem Cell Attachment to Biomaterials, Biomaterials, 2006, pp. 936-946, vol. 28, No. 6.
Prusa, et al., Oct-4-Expressing Cells in Human Amniotic Fluid: a New Source for Stem Cell Research?, Human Reproduction, 2003, pp. 1489-1493, vol. 18, No. 7.
Ptasznik, et al., Phosphatidylinositol 3-Kinase Is a Negative Regulator of Cellular Differentiation, The Journal of Cell Biology, 1997, pp. 1127-1136, vol. 137, No. 5.
R&D Systems, Embryonic & Induced Pluripotent Stem Cell Transcription Factors, Embryonic & Induced Pluripotent Stem Cell Transcription Factors, 2013, http://www.mdsystems.com/molecule_group.aspx?r=1&g-3041, 2 page web printout.
R&D Systems, Pancreatic Endoderm, Pancreatic Endoderm, Jun. 24, 2013, http://www.rndsystems.com/molecule_group.aspx?g=801 &r, 1 page web printout.
Rajagopal, et al., Insulin Staining of ES Cell Progeny from Insulin Uptake, Science, Jan. 17, 2003, pp. 363, vol. 299.
Ramiya, et al., Reversal of Insulin-Dependent Diabetes Using Islets Generated in vitro from Pancreatic Stem Cells, Nature Medicine, 2000, pp. 278-281, vol. 6.
Rao, Conserved and Divergent Paths that Regulate Self-Renewal in Mouse and Human Embryonic Stem Cells, Developmental Biology, Aug. 10, 2004, pp. 269-286, vol. 275, Elsevier, Inc.
Rebbapragada, et al., Myostatin Signals Through a Transforming Growth Factor B-Like Signaling Pathway to Block Adipogenesis, Molecular and Cellular Biology, 2003, pp. 7230-7242, vol. 23, No. 20.
Rebollar, et al., Proliferation of Aligned Mammalian Cells on Laser-Nanostructured Polystyrene, Biomaterials, 2008, pp. 1796-1806, vol. 29.
Reisner, Growing Organs for Transplantation form Embryonic Precursor Tissues, Immunol. Res., 2007, pp. 261-273, vol. 38.
Rezania, e al., Maturation of Human Embryonic Stem Cell-Derived Pancreatic Progenitors Into Functional Islets Capable of Treating Pre-Existing Diabetes in Mice, Diabetes, 2012, pp. 2016-2029, vol. 61.

(56) References Cited

OTHER PUBLICATIONS

Rezania, Production of Functional Glucagon-Secreting-Cells from Human Embryonic Stem Cells, Diabetes, 2011, pp. 239-247, vol. 60, Issue 1.
Richards et al., Comparative Evaluation of Various Human Feeders for Prolonged Undifferentiated Growth of Human Embryonic Stem Cells, Stem Cells, 2003, 546-556, 21, AlphaMed Publlishing.
Richardson, et al., Bortezomid (PS-341): A Novel, First-in-Class Proteasome Inhibitor for the Treatement of Multiple Myeloma and Other Cancers, Cancer Control, 2003, pp. 361-369, vol. 10, No. 5.
Ricordi et al., Automated Method for Isolation of Human Pancreatic Islets, Diabetes, Apr. 1988, 413-420, 37, American Diabetes Association.
Ross, et al., Cytochrome P450s in the Regulation of Cellular Retinoic Acid Metabolism, Annu. Rev. Nutr., 2011, pp. 65-87, vol. 31.
Ryan, et al., Clinical Outcomes and Insulin Secretion After Islet Transplantation with the Edmonton Protocol, Diabetes, Apr. 2001, pp. 710-719, vol. 50.
Sakaguchi, et al., Integration of Adult mesenchymal Stem Cells in the CNS, Society for Neuroscience Abstract Viewer and Itineray Planner, 2002, Program 237.18.
Sander, et al., Homeobox Gene Nkk6.1 Lies Downstream of Nkx2.2 in the Major Pathway of Betta-Cell Formation in the Pancreats, Development, 2000, pp. 5533-5540, vol. 127.
Sato et al., Maintenance of Pluripotency in Human and Mouse Embryonic Stem Cells Through Activation of Wnt Signaling by a Pharmacological GSK-3-specific Inhibitor, Nature Medicine, Jan. 2004, pp. 55-63, vol. 10, No. 1.
Sato, et al., Manipulation of Self-Renewal in Human Embryonic Stem Cells Through a Novel Pharmacological GSK-3 Inhibitor, Methods in Molecular Biology, 2006, pp. 115-128, vol. 331.
Sato, et al., Molecular Signature of Human Embryonic Stem Cells and its Comparison with the Mouse, Developmental Biology, Apr. 23, 2003, pp. 404-413, vol. 260.
Savino et al., Generation of Interleukin-6 Receptor Antagonists by Molecular-Modeling Guided Mutagenesis of Residues Important for gp130 Activation, EMBO Journal, 1994, 1357-1367, 13-6, IT.
Schisler, et al., The Nkx6.1 Homeodomain Transcription Factor Suppresses Glucagon Expression and Regulates Glucose-Stimulated Insulin Secretion in Islet Beta Cells, Proceedings of the National Academy of Sciences of the USA, 2005, pp. 7297-7302, vol. 102, No. 20.
Schraermeyer, et al., Subretinally Transplanted Embryonic Stem Cells Rescue Photoreceptor Cells From Degeneration in the RCS Rats, Cell Transplantation, 2001, pp. 673-680, vol. 10.
Schroeder, et al., Differentiation of Mouse Embryonic Stem Cells to Insulin-Producing Cells, Nature Protocols, 2006, pp. 495-507, vol. 1, No. 2.
Schuldiner, et al., Induced Neuronal Differentiation of Human Embryonic Stem Cells, Brain Research, 2001, pp. 201-205, vol. 913.
Scullica, et al., Diagnosis and Classification of Macular Degenerations: an Approach Based on Retinal Function Testing, Documenta Ophthalmologica, 2001, pp. 237-250, vol. 102.
Seaberg et al., Cfonal identification of multipotent precursors from adult ~ mouse pancreas that generate neural and pancreatic lineages, Nature Biotechnology, Sep. 2004, pp. 1115-1124, vol. 22, No. 9, Nature Publishing Group.
Segev, et al., Differentiation of Human Embryonic Stem Cells into Insulin-Producing Clusters, Stem Cells, Jan. 1, 2004, pp. 265-274.
Serafimidis, et al., Novel Effectors of Directed and Ngn3-Mediated Differentiation of Mouse Embryonic Stem Cells into Endocrine Pancreas Progenitors, Stem Cells, 2008, pp. 3-16, vol. 26.
Shackleton, et al., Generation of a Functional Mammary Gland from a Single Stem Cell, Nature, Jan. 5, 2006, pp. 84-88, vol. 439.
Shamblott et al., Derivation of pluripotent stem cells from cultured human primordial germ cells, Developmental Biology, Nov. 1998, 13726-13731, 95, National Academy of Sciences.
Shapiro, et al., Islet Transplantation in Seven Patients with Type 1 Diabetes Mellitus Using a Glucocorticoid-Free Immunosuppressive Regimen, The New England Journal of Medicine, Jul. 27, 2000, pp. 230-238, vol. 343, No. 4, The Massachusetts Medical Society.
Shen, et al., The Effects of Surface Chemistry and Adsorbed Proteins on Monocyte/Macrophage Adhesion to Chemically Modified Polystyrene Surfaces, Journal of Biomedical Matter Research, 2001, pp. 336-345, vol. 57.
Sherwood, et al., Transcriptional Dynamics of Endodermal Organ Formation, Developmental Dynamics, 2009, pp. 29-42, vol. 238, Issue 1.
Shi et al., Inducing Embryonic Stem Cells to Differentiate into Pancreatic β Cells by a Novel Three-Step Approach with Activin A and All-Trans Retinoic Acid, Stem Cells, 2005, 656-662, 23, AlphaMed Press.
Shim, et al., Directed Differentiation of Human Embryonic Stem Cells Towards a Pancreatic Cell Fate, Diabetologia, 2007, pp. 1228-1238, vol. 50.
Shiraki et al., TGF-B Signaling Potentiates Differentiation of Embryonic Stem Cells to Pdx-1 Expressing Endodermal Cells, Genes to Cells, 2005, 503-516, 10, Blackwell Publishing Limited.
Shiraki, et al., Guided Differentiation of Embryonic Stem Cells into Pdx1-Expressing Regional-Specific Definitive Endoderm, Stem Cells, 2008, pp. 874-885, vol. 26.
Simandi, et al., Retinoid Signaling is a Context-Dependent Regulator of Embryonic Stem Cells, Embryonic Stem Cells—Differentiation and Pluripotent Alternatives, 2011, pp. 55-79, Chapter 3.
Simons, et al., Assembly of Protein Tertiary Structures from Fragments with Similar Local Sequences Using Simulated Annealing and Bayesian Scoring Functions, Journal of Molecular Biology, 1997, pp. 209-225, vol. 268.
Simons, et al., Improved Recognition of Native-Like Protein Structures Using a Combination of Sequence-Dependent and Sequence-Independent Features of Proteins, Proteins: Structure, Function, and Genetics, 1999, pp. 82-95, vol. 34, Wiley-Liss, Inc.
Skoudy et al., Transforming growth factor (TGF)β, fibroblast growth factor (FGF) and retinoid signalling pathways promote pancreatic exocrine gene expression in mouse embryonic stem cells, Journal of Biochemistry, 2004, 749-756, 379, Biochemical Society, GB.
Smith et al., Anti-Interleukin-6 Monocolnal Antibody Induces Regression of Human Prostate Cancer Xenografts in Nude Mice, The Prostate, Mar. 2, 2001, 47-53, 48, Wiley-Liss, Inc.
Soria et al., Insulin-Secreting Cells Derived From Embryonic Stem Cells Normalize Glycemia in Streptozotocin-Induced Diabetic Mice, Diabetes, Feb. 2000, 1-6, 49, American Diabetes Association.
Soria, et al., From Stem Cells to Beta Cells: New Strategies in Cell Therapy of Diabetes Mellitus, Diabetologia, 2001, pp. 407-415, vol. 44.
Spence, et al., Translation Embryology: Using Embryonic Principles to Generate Pancreatic Endocrine Cells from Embryonic Stem Cells, Developmental Dynamics, 2007, pp. 3218-3227, vol. 236.
Stadtfeld, et al., Defining Molecular Cornerstones During Fibroblast to iPS Cell Reprogramming in Mouse, Cell Stem Cell, Mar. 2008, pp. 230-240, vol. 2.
Stafford, et al., Retinoic Acid Signaling is Required for a Critical Early Step in Zebrafish Pancreatic Development, Current Biology, 2002, pp. 1215-1220, vol. 12, Issue 14.
Stafford, et al., Retinoids Signal Directly to Zebrafish Endoderm to Specify Insuilin-Expressing B-cells, Development, 2005, pp. 949-956, vol. 133.
Sugiyama, et al., Conserved Markers of Fetal Pancreatic Epithelium Permit Prospective Isolation of Islet Progenitor Cells by FACS, PNAS, Jan. 2, 2007, pp. 175-180, vol. 104, No. 1.
Sugiyama, et al., Fluorescence-Activated Cell Sorting Purification of Pancreatic Progenitor Cells, Diabetes, Obesity and Metabolism, 2008, pp. 179-185, vol. 10, Supplement 4.
Suh, et al., Characterization of His-X3-His Sites in a-Helices of Synthetic Metal-Binding Bovine Somatotropin, Protein Engineering, 1991, pp. 301-305, vol. 4, No. 3.

(56) References Cited

OTHER PUBLICATIONS

Sulbacher, et al., Activin A-Induced Differentiation of Embryonic Stem Cells into Endoderm and Pancreatic Progenitors—The Influence of Differentiation Factors and Culture Conditions, Stem Cell Rev, 2009, pp. 159-173, vol. 5.
Sun, et al., Feeder-Free Derivation of Induced Pluripotent Stem Cells from Adult Human Adipose Stem Cells, Proceedings and the National Academy of Sciences, 2009, pp. 15720-15725, vol. 106, No. 37.
Suzuken, Differentiation of Multifunctional Stem Cells Using Human Feeder Cells, Research Papers of the Suzuken Memorial Foundation, 2007, pp. 193-197, vol. 24, JP.
Swindle, et al., Swine in Biomedical Research: Management and Models, ILAR News, 1994, pp. 1-5, vol. 36, No. 1.
Takahashi, et al., Homogenous Seeding of Mesenchymal Stem Cells into Nonwoven Fabric for Tissue Engineering, Tissue Engineering, 2003, pp. 931-938, vol. 9, No. 5.
Takahashi, et al., Induction of Pluripotent Stem Cells from Adult Human Fibroblasts by Defined Factors, Cell, 2007, pp. 861-872, vol. 131.
Takehara, et al., Rho-Associate Kinase Inhibitor Y-27632 Promotes Survival of Cynomolgus Monkey Embryonic Stem Cells, Molecular Human Reproduction, 2008, pp. 627-634, vol. 14, No. 11.
Tang, et al., Reprogramming Liver-Stem WB Cells into Functional Insulin-Producing Cells by Persistent Expression of Pdx1-and Pdx1-VP16 Mediated by Lentiviral Vectors, Laboratory Investigation, 2006, pp. 83-93, vol. 86.
Tannock, et al., Chemotherapy with Mitoxantrone Plus Prednisone or Prednisone Alone for Symptomatic Hormone-Resistant Prostate Cancer: A Canadian Randomized Trial With Palliative End Points, Journal of Clinical Oncology, 1996, 1756-1764, 14-6, American Society of Clinical Oncology, US.
Teare, et al., Cellular Attachment to Ultraviolet Ozone Modified Polystyrene Surfaces, Langmuir, 2000, pp. 2818-2824, vol. 16.
Tomita, et al., Bone Marrow-Derived Stem Cells Can Differentiate into Retinal Cells in Injured Rat Retina, Stem Cells, 2002, pp. 279-283, vol. 20.
Totonchi, et al., Feeder-and Serum-Free Establishment and Expansion of Human Induced Pluripotent Stem Cells, Int. J. Dev. Biol., 2010, pp. 8770886, vol. 54.
Tsai, et al., Isolation of Human Multipotent Mesenchymal Stem Cells from Second-Trimester Amniotic Fluid Using a Novel Two-Stage Culture Protocol, Human Reproduction, Apr. 22, 2004, pp. 1450-1456, vol. 19, No. 6.
Tulachan et al., TGF-β isoform signaling regulates secondary transition and mesenchymal-induced endocrine development in the embryonic mouse pancreas, Developmental Biology, 2007, 508-521, 305, Elsevier.
Ubeda et al., Inhibition of Cyclin-dependent Kinase 5 Activity Protects Pancreatic Beta Cells from Glucotoxicity, Journal of Biological Chemistry, Aug. 3, 2006, 28858-28864, 39, JBC Papers in Press.
Uludag, et al., Technology of Mammalian Cell Encapsulation, Advanced Drug Delivery Reviews, 2000, pp. 29-64, vol. 42.
Ungrin, et al., Reproducible, Ultra High-Throughput Formation of Multicellular Organization from Single Cell Suspension-Derived Human Embryonic Stem Cell Aggregates, Plos ONE, 2008, e1565, pp. 1-12, vol. 3, Issue 2.
Unknown, Preserve the Stability of Your Stem Cells, Stem Cells, 2006, Internet Citation, XP002496166.
Vacanti, et al., Selective Cell Transplantation Using Bioabsorbable Artificial Polymers as Matrices, Journal of Pediactric Surgery, Jan. 1988, 3-9, 23-1.
Valet, et al., Pretherapeutic Identification of High-Risk Acute Myeloid Leukemia (AML) Patients from . . . , Clinical Cytometry, Feb. 17, 2003, 4-10, 53B, Wiley-Liss, Inc., US.
Van Der Greef et al., Rescuing drug discovery: in vivo systems pathology and systems pharmacology, Nature, Dec. 1, 2005, 961-967, 4-1, Nature Reviews, US.
Van Der Windt, et al., The Chioce of Anatomical Site for Islet Transplantation, Cell Transplantation, 2008, pp. 1005-1014, vol. 17.
Van Wachem, et al., Method for the Fast Application of an Evenly Distributed Cell Layer on Porous Vascular Grafts, Biomaterials, 1990, pp. 602-606, vol. 11.
Vanderford et al., Multiple kinases regulate mafA expression in the pancreatic beta cell line MIN6, Biochemistry and Biophysics, 2008, 138-142, 480, Elsevier.
Verfaillie, et al., Stem Cells: Hype and Reality, Hematology, 2002, pp. 369-391.
Vodicka, et al., The Miniature Pig as an Animal Model in Biomedical Research, Annals New York Academy of Sciences, 2005, pp. 161-171, vol. 1049.
Vunjak-Novakovic, et al., Dynamic Cell Seeding of Polymer Scaffolds for Cartilage Tissue Engineering, Biotechnology Program, 1998, pp. 193-202, vol. 14, Issue 2.
Wang et al., Derivation and Growing Human Embryonic Stem Cells on Feeders Derived from Themselves, Stem Cells, 2005, 1221-1227, 23, AlphaMed Press.
Wang et al., Relationship of Chemical Structurs of Anthraquinones with their Effects onthe Suppression of Immune Responses, International Journal of Immunopharmacology, 1987, 733-739, 9-6, International Society for Immunopharmacology, GB.
Wang, et al., Noggin and bFGF Cooperate to Maintain the Pluripotency of Human Embryonic Stem Cells in the Absence of Feeder Layers, Biochemical and Biophysical Research Communications, 2005, pp. 934-942, vol. 33, No. 3.
Watanabe, et al., A Rock Inhibitor Permits Survival of Dissociated Human Embryonic Stem Cells, Nature Biotechnology, 2007, pp. 681-686, vol. 25, No. 6.
Wei et al., Cdk5-dependent regulation of glucose-stimulated insulin secretion, Nature Medicine, Sep. 11, 2005, 1104-1108, 11-10, Nature Publishing Group.
Wei, et al., Human Amnion-Isolated Cells Normalize Blood Glucose in Strepozotocin Induced Diabetic Mice, Cell Transplantation, 2003, pp. 545-552, vol. 12, No. 5.
Wei, et al., Transcriptome Profiling of Human and Murine ESCs Identifies Divergent Paths Required to Maintain the Stem Cell State, Stem Cells, 2005, pp. 166-185, vol. 23.
Wells, et al., Early Mouse Endoderm is Patterned by Soluble Factors from Adjacent Germ Layers, Development, 2000, pp. 1563-1572, vol. 127, Issue 8.
Wernig, et al., c-Myc is Dispensable for Direct Reprogramming of Mouse Fibroblasts, Cell Stem Cell, Jan. 2008, pp. 10-12, vol. 2.
White, et al., Complex Regulation of cyp26a1 Creates a Robust Retinoic Acid Gradient in the Zebrafish Embryo, PLOS Biology, 2007, pp. 2522-2533, vol. 5, Issue 11.
Wiles et al., Embryonic Stem Cell Development in a Chemically Defined Medium, Experimental Cell Research, 1999, 241-248, 247, Academic Press.
Wilson, et al., The HMG Box Transcription Factor Sox4 Contributes to the Development of the Endcrine Pancreas, Diabetes, 2005, pp. 3402-4309, vol. 54, Issue 12.
Wong, et al., Directed Differentiation of Human Pluripotent Stem Cells into Mature Airway Epithelia Expressing Functional CFTR Protein, Nature Biotechnology, 2012, pp. 876-884, vol. 30, No. 9.
XP002553616_1989, RecName: Full=Inhibin beta B Chain; AltName: Full=Activin beta-B chain; Flags; Precurso, Database UniProt [Online], Jul. 1, 1989, Database Accession No. P09529, EBI Accession No. Uniprot: P09529.
Xu, et al., Basic FGF and Suppression of BMP Signalling Sustain Undifferentiated Proliferation of Human ES Cells, Nature Methods, 2005, pp. 185-189, vol. 2, Issue 3.
Xu, et al., Feeder-free Growth of Undifferentiated Human Embryonic Stem Cells, Nature Biotechnology, 2001, pp. 971-974, vol. 19.
Yang et al., Novel cell immobilization method utilizing centrifugal force to achieve high-density hepatocyte culture in porous scaffold, Journal of Biomed Materials Research, Feb. 27, 2001, 379-386, 55, John Wiley & Sons, Inc.
Yang, et al., Survival of Pancreatic Islet Xenografts in NOD Mice with the Theracyte Device, Transplantation Proceedings, 2002, pp. 3349-3350, vol. 34.

(56) References Cited

OTHER PUBLICATIONS

Yasuda, et al., Development of Cystic Embryoid Bodies with Visceral Yolk-Sac-Like Structures from Mouse Embryonic Stem Cells Using Low-Adherence 96-Well Plate, Journal of Bioscience and Bioengineering, Apr. 4, 2009, pp. 442-446, vol. 107, No. 4.
Yoneda, et al., The Rho Kinases I and II Regulate Different Aspects of Myosin II Acitivity, The Journal of Cell Biology, 2005, pp. 443-445, vol. 170, No. 3.
Young, et al., Three-Dimensional Culture of Human Uterine Smooth Muscle Nyocytes on a Resorbably Scaffolding, Tissue Engineering, 2003, pp. 451-459, vol. 9, No. 3.
Yu, et al., Induced Pluripotent Stem Cell Lines Derived from Human Somatic Cells, Science, Dec. 21, 2007, pp. 1917-1920, vol. 318.
Zembower, et al., Peptide Boronic Acids Versatile Synthetic Ligands for Affinity Chromatography of Serine Proteinases, International Journal Peptide Protein, 1996, pp. 405-413, vol. 47.
Zhang et al., MafA Is a Key Regulator of Glucose-Stimulated Insulin Secretion, Molecular and Cellular Biology, Jun. 2005, 4969-4976, 25-12, American Society for Microbiology.
Zhang, et al., Differentiation Potential of Bone Marrow Mesenchymal Stem Cells into Retina in Normal and Laser-Injured Rat Eye, Science in China Series, 2004, pp. 241-250, vol. 47, No. 3.
Zhang, Jie, The Differentiation of Bone Marrow Mesenchymal Stem Cells into Retina in Rat Eye and the Therapeutical Effect on Severe Injured Retina, A Doctoral Thesis of Chinese PLA Acadamey of Military Medical Sciences, 2003, 1-127, 1-127.
Zhang_et_al, Highly Efficient Differentiation of Human ES Cells and iPS Cells into Mature Pancreatic Insulin-Producing Cells, Cell Research, 2009, pp. 429-438, vol. 19, Issue 14.
Zhao et al., The Islet B Cell-enriched MafA Activator is a Key Regulator of Insulin Gene Transcription, Journal of Biological Chemistry, Mar. 25, 2005, 11887-11894, 280-12, The Amerian Society for Biochemistry and molecular Biology, Inc.
Zhao, et al., Derivation and Characterization of Hepatic Progenitor Cells from Human Embryonic Stem Cells, PLoS ONE Hepatic Progenitors from hESCs, Jul. 2009, e6468 pp. 1-10, vol. 4, Issue 7.
Zorn, et al., Vertebrate Endoderm Development and Organ Formation, Annual Review Cell Development Biology, 2009, pp. 221-251, vol. 25.
Zubaty, et al., Transplantation of Mesenchymal Stem Cells into RCS Rats for Retinal Repair, Investigative Ophthalmology and Visual Science, 2005, pp. 4160-B518, vol. 46, Supplement S.
Best, et al., Embryonic Stem Cells to Beta-Cells by Understanding Pancreas Development, Molecular and Cellular Endorinology, 2008, pp. 86-94, vol. 288.
Bo, et al., Research Progress of Pancreatic Islet Development and Pancreatic Stem Cells, Journal of Clinical Surgery, 2009, pp. 208-210, vol. 17, No. 3.
Chetty, et al., A Simple Tool to Improve Pluripotent Stem Cell Differentiation, Nature Methods, 2013, pp. 553-558, vol. 10, No. 6.
Deramaudt, et al., The PDX1 Homeodomain Transcription Factor Negatively Regulates the Pancreatic Ductal Cell-specific Keratin 19 Promoter*, Journal of Biological Chemistry, 2006, pp. 38385-38395, vol. 281, No. 50.
Gibco, Solutions for Life Science Research and Drug Discovery, Catalogue Cell Culture Products, 2004-2005, pp. 1-4E, 281406 26 5 27.
Gordon Weir, Do stem cells hold the key to creation of a cure for diabetes?, Diabetes Voice, 2008, pp. 29-31, Edition 53, No. 2.
Hay, et al., Highly Effiicient Differentiation of hESCs to Functional Hepatic Endoderm Requires ActivinA and Wnt3a Signaling, PNAS, 2008, pp. 12301-12306, vol. 105, No. 34.
Itkin-Ansari, et al., Cell-Based Therapies for Diabetes: Progress Towards a Transplantable Human B Cell Line, Annals of the New York Academy of Sciences, 2003, pp. 138-147, vol. 1005, No. 1.
Schnier, et al., G1 Arrest and Down-Regulation of Cyclin E/cyclin-dependent Kinase 2 by the Protein Kinase Inhibitor Staurosporine are Dependent on the Retinoblastoma Protein in the Bladder Carcinoma Cell Line 5637, Proceedings of the National Academy of Sciences, 1996, pp. 5941-5946, vol. 93.
Stoffel, et al., Navigating the Pathway from Embryonic Stem Cells to Beta Cells, Seminars in Cell & Developmental Biology, 2004, pp. 327-336, vol. 15.
Tsuchida, et al., Activin Isoforms Signal Through Type I Receptor Serine/Threonin Kinase ALK7, Molecular and Cellular Endocrinology, 2004, pp. 59-65, vol. 22.
Xudong, et al., Research Progress in Inducing Stem Cels to Differentiate toward the B-like Cells of Pancreatic Islet, Chinese Bulletin of Life Sciences, 2007, pp. 526-530, vol. 19, No. 5.
Amit, et al., Dynamic Suspension Culture for Scalable Expansion of Undifferentiated Human Pluripotent Stem Cells, Nature Protocols, Apr. 7, 2011, pp. 572-579, vol. 6, No. 5.
Baertschiger, et al., Mesenchymal Stem Cells Derived From Human Exocrine Pancreas Express Transcription Factors Implicated in Beta-Cell Development, Pancreas, 2008, pp. 75-84, vol. 37, No. 1.
Cao, et al., High Glucose is Necessary for Complete Maturation of Pdx1-VP16-Expressing Hepatic Cells into Functional Insulin-Producing Cells, Diabetes, 2004, pp. 3168-3176, vol. 53.
Eguizabal, et al., Embryonic Stem Cells/Induced Pluriptent Stem Complete Meiosis from Human Induced Pluripotent Stem Cells, Stem Cells, 2011, pp. 1186-1195, vol. 29.
Furue, et al., Heparin Promotes the Growth of Human Embryonic Stem Cells in a Defined Serum-Free Medium, Proceedings of the National Academy of Sciences, Sep. 9, 2008, pp. 13409-13414, vol. 105, No. 36.
Harmon, et al., GDF11 Modulates NGN3+ Islet Progenitor Cell Number and Promotes B-Cell Differentiation in Pancreas Development, Development, 2004, pp. 6163-6174, vol. 131.
Jiang, et al., In Vitro Derivation of Functional Insulin-Producing Cells from Human Embryonic Stem Cells, Cell Research, 2007, pp. 333-344, vol. 17.
Leeper, et al., Stem Cell Therapy for Vascular Regeneration Adult, Embryonic, and Induced Pluripotent Stem Cells, Circulation, Aug. 3, 2010, pp. 517-526, vol. 122, No. 5.
Ludwig, et al., Defined Culture Media for Human Embryonic Stem Cells, Embryonic Stem Cells, 2007, pp. 1-16, Springer.
Minami, et al., A Small Molecule that Promotes Cardiac Differentiation of Human Pluripotent Stem Cells Under Defined, Cytokine- and Xeno-free Conditions, Cell Reports, 2012, pp. 1448-1460, vol. 2, No. 5.
Nie, et al., Scalable Passaging of Adherent Human Pluripotent Stem Cells, PLOS One, 2014, pp. 1-9, vol. 9, Issue 1.
Park, et al., Effects of Activin A on Pancreatic Ductal Cells in Streptozotocin-Inducted Diabetic Rats, Experimental Transplantation, 2007, pp. 925-930, vol. 83.
Rajala, et al., Testing of Nine Different Xeno-free Culture Media for Human Embryonic Stem Cell Cultures, Human Reproduction, Jan. 24, 2007, pp. 1231-1238, vol. 22, No. 5.
Rezania, et al., Enrichment of Human Embryonic Stem Cell-Derived NKX6.1—Expressing Pancreatic Progenitor Cells Accelerates the Maturation of Insulin-Secreting Cells In Vivo, Stem Cells, 2013, pp. 2432-2442, vol. 31.
Richards, et al., Development of Defined Media for the Serum-Free Expansion of Primary Keratinocytes and Human Embryonic Stem Cells, Tissue Engineering, 2008, pp. 221-232, vol. 14, No. 3.
Rowley, et al., Meeting Lot-Size Challenges of Manufacturing Adherent Cells for Therapy, Cell Therapies Manufacturing, 2012, pp. 16-22, vol. 10, No. 3.
Schulz, et al., A Scalable System for Production of Functional Pancreatic Progenitors from Human Embryonic Stem Cells, PLOS One, 2012, pp. 1-17, vol. 7, Issue 5.
Sneddon, et al., Self-Renewal of Embryonic-Stem-Cell-Derived Progenitors by Organ-Matched Mesenchyme, Nature, Nov. 29, 2012, pp. 765-770, vol. 491.
Stacpoole, et al., Efficient Derivation of Neural Precuros Cells, Spinal Motor Neurons and Midbr, Nat Protoc, 2012, pp. 1-26, vol. 6, Issue 8.
Vieira, et al., Modulation of Neuronal Stem Cell Differentiation by Hypoxia and Reactive Oxygen Species, Progress in Neurobiology, 2011, pp. 444-455, vol. 93.

(56) References Cited

OTHER PUBLICATIONS

Wang, et al., Three-Dimensional Differentiation of Embryonic Stem Cells into islet-Like Insulin-Producing Clusters, Tissue Engineering: Part A, 2009, pp. 1941-1952, vol. 15, No. 8.

Want, et al., Large-Scale Expansion and Exploitation of Pluripotent Stem Cells for Regenerative Medicine Purposes: beyond the T Flask, Loughborough University Institutional Repository, 2012, pp. 71-84, vol. 7, Issue 1.

Yang, et al., Evaluation of Humam MSCs Cell Cycle, Viability and Differentiation in Micromass Culture, Biorheology, 2006, p. 489-496, vol. 43.

Zalzman, et al., Differentiation of Human Liver-Derived, Insulin-Producing Cells Toward the B-Cell Phenotype, Diabetes, 2005, pp. 2568-2575, vol. 54.

Zuscik, et al., Regulation of Chondrogenesis and Chondrocyte Differentiation by Stress, J Clin Invest, 2008, pp. 429-438, vol. 118, Issue 2.

Cohick, et al., The Insulin-Like Growth Factors, Annual Reviews Physiol, 1993, pp. 131-153, vol. 55, Annual Reviews Inc.

Hebrok, et al., Notochord repression of endodermal Sonic hedgehog permits pancreas development, Genes & Development, Jun. 1, 1998, pp. 1705-1713, vol. 12, Issue 11, Cold Spring Harbor Laboratory Press.

Jaenisch, et al., Stem Cells, the Molecular Circuitry of Pluripotency and Nuclear Reprogramming, cell, Feb. 22, 2008, pp. 567-582, vol. 132, Elsevier Inc.

Klajnert, et al., Fluorescence studies on PAMAM dendrimers interactions with bovine serum albumin, Bioelectrochemistry, 2002, pp. 33-35, vol. 55.

Kubota,et al., Growth factors essential for self-renewal and expansion of mouse spermatogonial stem cells, cell Biology, Nov. 23, 2004, pp. 16489-16494, vol. 101, Issue 47.

Nostro, et al., Generation of Beta Cells from Human Pluripotent Stem Cells: Potential for Regenerative Medicine, Seminars in Cell & Developmental Biology, 2012, pp. 701-710, vol. 23.

Ratanasavanh,et al., Immunocytochemical Evidence for the Maintenance of Cytochrome P450 Isozymes, NADPH Cytochrome C Reductase, and Epoxide Hydrolase in Pure and Mixed Primary Cultures of Adult Human Hepatocytes1, The Journal of Histochemistry and Cytocheinistry, 1986, pp. 527-533, vol. 34, Issue 4.

Rezania, et al., Reversal of Diabetes with Insulin-Producing Cells Derived in vitro from Human Pluripotent Stem Cells, Nature Biotechnology, 2014, pp. 1121-1133, vol. 32, No. 11.

Schaefer-Graf, et al., Patterns of congenital anomalies and relationship to initial maternal fasting glucose levels in pregnancies complicated by type 2 and gestational diabetes, Am J Obstet Gynecol, 2000, pp. 313-320, vol. 182, Issue 2.

Thermofisher Scientific, B-27 Serum-Free Supplement (50x) Liquid, Technical Resources, 2016, URL:https://www.thermofisher.com/nl/en/home/technical-resources/media-formulation.250.html, retrieved from the internet.

Wachs, et al., High Efficacy of Clonal Growth and Expansion of Adult Neural Stem Cells, Laboratory Investigation, 2003, pp. 949-962, vol. 83, No. 7.

Brimble S. et al., The Cell Surface Glycosphingolipis SSEA-3 and SSEA-4 Are Not Essential for Human ESC Pluripotency, Stem Cells, Jan. 2007, pp. 54-62, vol. 25, MX.

Buta et al., Reconsidering pluripotency tests: Do we still need teratoma assays?, Stem Cell Research, Mar. 26, 2013, pp. 552-562, vol. 11.

Chen, et al., Retinoic acid signaling is essential for pancreas development and promotes endocrine at the expense of exocrine cell differentiation in Xenopus, Developmental Biology, May 4, 2004, pp. 144-160, vol. 271.

Cirulli, et al., Netrins: beyond the brain, Molecular Cell Biology, Apr. 2007, pp. 296-306, vol. 8.

Furue, et al., Heparin propotes the growth of human embryonic stem cells in a defined serum-free medium, PNAS, Sep. 9, 2008, pp. 13409-13414, vol. 105 Issue 36.

Gibco, Insulin-Transferin-Selenium-X 100X, Invitrogen Cell Culture, Apr. 2005, pp. 1, Form No. 3032.

Gomez, et al., Derivation of cat embryonic stem-like cells from in vitro-produced blastocysts on homologous and heterologous feeder cells, Theriogenology, May 11, 2010, pp. 498-515, vol. 74.

Gordon Weir., Do stem cells hold the key to a future cure for diabetes?, DiabetesVoice, Jun. 2008, pp. 29-31, vol. 53 Issue 2.

Hiemisch, H., et al., Transcriptional Regulation in Endoderm Develoment: Characterization of an Enhancer Controlling Hnf3g Expression by Transgenesis and Targeted Mutagenesis, The EMBO Journal, 1997, 3995-4006, vol. 16(13), MX.

Jean, et al., Pluripotent genes in avian stem cells, Development Growth & Differentitaion, 2013, pp. 41-51, vol. 55.

Kang, et al., Plasma treatment of textiles—Synthetic Polymer-Based Textiles, AATCC Review, 2004, pp. 29-33, Page number.

King, et al., Bioreactor development for stem cell expansion and controlled differentiation, Current Opinion in Chemical Biology, Jul. 25, 2007, pp. 394-398, vol. 11, Elsevier Ltd.

Kunisada, et al., Small molecules induce efficient differentiation into insulin-producing cells from human induced pluripotent stem cells, Stem Cell Research, Oct. 11, 2011, pp. 274-284, vol. 8.

Lavial, etal., Chicken Embryonic Stem Cells as a Non-Mammalian Ebryonic Stem Cell Model, Development Growh Differentiation, Jan. 2010, pp. 101-114, vol. 52(1).

Lin, C., et al., Coagulation Dysregulatin as a Barrier to Xenotransplantation n the Primate, Transplant Immunology, 2009, pp. 75-80, vol. 21, MX.

Maria-Jesus Obregon, Thyroid hormone and adipocyte differentiation, Thyroid, 2008, pp. 185-195, vol. 18 Issue 2.

McMahon, et al., Noggin-mediated antagonsim of BMP signaling is required for growth and patterning of the neural tube and somite, Genes & Development, Mar. 16, 1998, pp. 1438-1452, vol. 12.

Nakase, et al., Myeliod Antigen, CD13, CD14, and/ or CD33 Expression Is Restricted to Certain Lymphiod Neoplasms, Hematopathology, Jun. 1996, pp. 761-768, vol. 105 Issue 6.

Narang, A., et al., Biological and Biomaterial Approaches for Improved Islet Transplantation, Pharmacological Review, Jun. 2006, pp. 194-243, vol. 58(2), MX.

Ouziel-Yahalom, et al., Expansion and redifferentiation of adult human pancreatic islet cells, Biochemical and Biophysical Research Communications, Jan. 19, 2006, pp. 291-298, vol. 341.

Petitte, J., et al., Avian Plluripotent Stem Cells, Mechanisms of Development, 2004, pp. 1159-1168, vol. 121, MX.

Ramiya, et al., Reversal of insulin-dependent diabetes using islets generated in vitro from pancreatic stem cells, Nature Medicine, Mar. 2000, pp. 278-282, vol. 6 Issue 3.

Rother, et al., Challenges facing islet transplantation for the treatment of type 1 diabetes mellitus, The Journal of Clinical Investigation, 2004, pp. 877-883, vol. 114 Issue 7.

Rowely, et al., Meeting Lot-size Challenges of Manufacturing Adherent Cells for Therapy, Bio Process International, Mar. 2012, pp. 16-22, vol. 10 Issue 3.

Sjögren-Jansson, et al., Large-Scale Propagation of Four Undifferentiated Human Embryonic Stem Cell Lines in a Feeder-Free Culture System, Developmental Dynamics, Jun. 17, 2005, pp. 1304-1314, vol. 233.

Strizzi, et al., Netrin-1 regulates invasion and migration of mouse mammary epithelial cells overexpressing Cripto-1 in vitro and in vivo, Journal of Cell Science, Jul. 7, 2005, pp. 4633-4643, vol. 118 Issue 20.

Suzuken., Differentiation of Multifunctional Stem Cells Using Human Feeder Cells, Research Papers of the Suzuken Memorial Foundation, 2007, pp. 193-197, vol. 2.

Yadlin, et al., Small-molecule inducers of insulin expression in pancreatic α-cells, PNAS, Aug. 24, 2010, pp. 15099-15104, vol. 107 Issue 34.

Yang JW et al., Evaluation of human MSCs cell cycle, viability and differentiation in micromass culture, Bioheology, 2006, pp. 1-2, vol. 43 Issue (3-4).

Zulewski, et al., Multipotentital Nestin-Positive Stem Cells Iasolated From Adult Pancreatic Islets Differentiate Ex Vivo Into Pancreatic Endocrine, Exocrine, and Hepatic Phenotypes, Diabetes, 2001, pp. 521-533, vol. 50.

(56) References Cited

OTHER PUBLICATIONS

Beers, et al., Passaging and Colony Expansion of Human Pluripotent Stem Cells by Enzyme-Free Dissociation in Chemically Defined Culture Conditions, Nature Protocols, 2012, pp. 2029-2040, vol. 7, No. 11.

Chen, et al., Scalable GMP Compliant Suspension Culture System for Human ES Cells, Stem Cell Research, 2012, pp. 388-402, vol. 8.

Guo, et al., Efficient differentiation of insulin-producing cells from skin-derived stem cells, Cell Proliferation, 2009, pp. 49-62, vol. 42.

Olmer, et al., Long Term Expansion of Undifferentiated Human iPS and ES Cells in Suspension Culture Using Defined Medium, Stem Cell Research, 2010, pp. 51-64, vol. 5.

Thomson, Bioprocessing of Embryonic Stem Cells for Drug Discovery, Trends in Biotechnology, 2007, pp. 224-230, vol. 25, No. 5.

\* cited by examiner

METHODS AND COMPOSITIONS FOR CELL ATTACHMENT AND CULTIVATION ON PLANAR SUBSTRATES

The present invention claims priority to application Ser. No. 61/116,452, filed Nov. 20, 2008.

FIELD OF THE INVENTION

The present invention is directed to methods for the growth, expansion and differentiation of pluripotent stem cells on planar substrates lacking an adlayer and a feeder cell layer.

BACKGROUND

Cultivation of mammalian cells is one of many processes in the life and health sciences. Vessels for mammalian cell culture and analysis involving anchorage-dependent cells are often made of glass or a polymer, such as, for example, polystyrene, that frequently requires additional surface treatment to allow the cells to attach to the surface of the vessel. Such treatments may include applying an adlayer on the surface, for example, by adsorption, grafting or plasma polymerization techniques. Alternatively, the surface treatment may be via chemical modification of the vessel surface itself, which can be achieved by, for example, atmospheric corona, radio frequency vacuum plasma, DC glow discharge, and microwave plasma treatments.

Current methods of culturing pluripotent stem cells, in particular, embryonic stem (ES) cells require complex culture conditions, such as, for example, culturing the embryonic stem cells on a solid substrate surface with a feeder cell layer, or on a solid substrate surface with an adlayer of extracellular matrix protein. Culture systems that employ these methods often use feeder cells or extracellular matrix proteins obtained from a different species than that of the stem cells being cultivated (xenogeneic material). Media obtained by exposure to feeder cells, that is, media conditioned by cells other than undifferentiated ES cells, may be used to culture the ES cells, and media may be supplemented with animal serum.

For example, Reubinoff et al. (Nature Biotechnol. 18:399-404, 2000) and Thompson et al. (Science 282:1145-1147, 1998) disclose the culture of ES cell lines from human blastocysts using a mouse embryonic fibroblast feeder cell layer.

In another example, Xu et al. (Nature Biotechnology 19:971-974, 2001) discloses the use of MATRIGEL® and laminin for treating solid substrate surfaces before feeder-cell free cultivation of human ES cells without differentiation. In another example, Vallier et al. (J. Cell Sci. 118:4495-4509, 2005) discloses the use of fetal bovine serum for treating solid substrate surfaces before feeder-cell free cultivation of human ES cells without differentiation.

In another example, WO2005014799 discloses conditioned medium for the maintenance, proliferation and differentiation of mammalian cells. WO2005014799 state: "The culture medium produced in accordance with the present invention is conditioned by the cell secretion activity of murine cells, in particular, those differentiated and immortalized transgenic hepatocytes, named MMH (Met Murine Hepatocyte)."

In another example, Wanatabe et al. (Nature Biotechnol. 35:681-686, 2007) state "a ROCK inhibitor permits survival of dissociated human embryonic stem cells", and demonstrate reduced dissociation-induced apoptosis, increases cloning efficiency (from approximately 1% to approximately 27%) and facilitation of subcloning after gene transfer, using mouse embryonic fibroblasts as feeder cells, collagen and MATRIGEL® as extracellular matrix protein, and Y-27632 or Fasudil for inhibition of ROCK. Furthermore, dissociated human ES cells treated with Y-27632 were protected from apoptosis in serum-free suspension culture.

In another example, Peerani et al. (EMBO Journal 26:4744-4755, 2007) state "Complexity in the spatial organization of human embryonic stem cell (hESC) cultures creates heterogeneous microenvironments (niches) that influence hESC fate. This study demonstrates that the rate and trajectory of hESC differentiation can be controlled by engineering hESC niche properties. Niche size and composition regulate the balance between differentiation-inducing and inhibiting factors. Mechanistically, a niche size-dependent spatial gradient of Smad1 signaling is generated as a result of antagonistic interactions between hESCs and hESC-derived extra-embryonic endoderm (ExE). These interactions are mediated by the localized secretion of bone morphogenetic protein-2 (BMP2) by ExE and its antagonist, growth differentiation factor-3 (GDF3) by hESCs. Micropatterning of hESCs treated with small interfering (si) RNA against GDF3, BMP2 and Smad1, as well treatments with a Rho-associated kinase (ROCK) inhibitor demonstrate that independent control of Smad1 activation can rescue the colony size-dependent differentiation of hESCs. Our results illustrate, for the first time, a role for Smad1 in the integration of spatial information and in the niche-size dependent control of hESC self-renewal and differentiation."

In another example, Koyanagi, M et al (J Neurosci Res. 2008 Feb. 1; 86(2): 270-80) state "Rho-GTPase has been implicated in the apoptosis of many cell types, including neurons, but the mechanism by which it acts is not fully understood. Here, we investigate the roles of Rho and ROCK in apoptosis during transplantation of embryonic stem cell-derived neural precursor cells. We find that dissociation of neural precursors activates Rho and induces apoptosis. Treatment with the Rho inhibitor C3 exoenzyme and/or the ROCK inhibitor Y-27632 decreases the amount of dissociation-induced apoptosis (anoikis) by 20-30%. Membrane blebbing, which is an early morphological sign of apoptosis; cleavage of caspase-3; and release of cytochrome c from the mitochondria are also reduced by ROCK inhibition. These results suggest that dissociation of neural precursor cells elicits an intrinsic pathway of cell death that is at least partially mediated through the Rho/ROCK pathway. Moreover, in an animal transplantation model, inhibition of Rho and/or ROCK suppresses acute apoptosis of grafted cells. After transplantation, tumor necrosis factor-alpha and pro-nerve growth factor are strongly expressed around the graft. ROCK inhibition also suppresses apoptosis enhanced by these inflammatory cytokines. Taken together, these results indicate that inhibition of Rho/ROCK signaling may improve survival of grafted cells in cell replacement therapy."

The use of xenogeneic material may be unsuitable for certain applications utilizing pluripotent stem cells. Alternative materials may be used. For example, Stojkovic et al. (Stem Cells 23:895-902, 2005) discloses the use of human serum for treating solid substrate surfaces before feeder-cell free cultivation of human ES cells without differentiation.

An alternative culture system employs serum-free medium supplemented with growth factors capable of promoting the proliferation of embryonic stem cells.

For example, Cheon et al. (BioReprod DOI:10.1095/biolreprod.105.046870; 19 Oct. 2005) disclose a feeder-cell free, serum-free culture system in which ES cells are maintained in unconditioned serum replacement medium supplemented with different growth factors capable of triggering ES cell self-renewal.

In another example, Levenstein et al. (Stem Cells 24:568-574, 2006) disclose methods for the long-term culture of human ES cells in the absence of fibroblasts or conditioned medium, using media supplemented with basic fibroblast growth factor (FGF).

In another example, US20050148070 discloses a method of culturing human ES cells in defined media without serum and without fibroblast feeder cells, the method comprising: culturing the stem cells in a culture medium containing albumin, amino acids, vitamins, minerals, at least one transferrin or transferrin substitute, at least one insulin or insulin substitute, the culture medium essentially free of mammalian fetal serum and containing at least about 100 ng/ml of a FGF capable of activating a FGF signaling receptor, wherein the growth factor is supplied from a source other than just a fibroblast feeder layer, the medium supported the proliferation of stem cells in an undifferentiated state without feeder cells or conditioned medium.

In another example, US20050233446 discloses a defined media useful in culturing stem cells, including undifferentiated primate primordial stem cells. In solution, the media is substantially isotonic as compared to the stem cells being cultured. In a given culture, the particular medium comprises a base medium and an amount of each of basic FGF, insulin, and ascorbic acid necessary to support substantially undifferentiated growth of the primordial stem cells.

In another example, U.S. Pat. No. 6,800,480 states: "In one embodiment, a cell culture medium for growing primate-derived primordial stem cells in a substantially undifferentiated state is provided which includes a low osmotic pressure, low endotoxin basic medium that is effective to support the growth of primate-derived primordial stem cells. The basic medium is combined with a nutrient serum effective to support the growth of primate-derived primordial stem cells and a substrate selected from the group consisting of feeder cells and an extracellular matrix component derived from feeder cells. The medium further includes nonessential amino acids, an anti-oxidant, and a first growth factor selected from the group consisting of nucleosides and a pyruvate salt."

In another example, US20050244962 states: "In one aspect the invention provides a method of culturing primate embryonic stem cells. One cultures the stem cells in a culture essentially free of mammalian fetal serum (preferably also essentially free of any animal serum) and in the presence of fibroblast growth factor that is supplied from a source other than just a fibroblast feeder layer. In a preferred form, the fibroblast feeder layer, previously required to sustain a stem cell culture, is rendered unnecessary by the addition of sufficient fibroblast growth factor."

In another example, WO2005065354 discloses a defined, isotonic culture medium that is essentially feeder-free and serum-free, comprising: a. a basal medium; b. an amount of basic fibroblast growth factor sufficient to support growth of substantially undifferentiated mammalian stem cells; c. an amount of insulin sufficient to support growth of substantially undifferentiated mammalian stem cells; and d. an amount of ascorbic acid sufficient to support growth of substantially undifferentiated mammalian stem cells.

In another example, WO2005086845 discloses a method for maintenance of an undifferentiated stem cell, said method comprising exposing a stem cell to a member of the transforming growth factor-beta (TGFβ) family of proteins, a member of the fibroblast growth factor (FGF) family of proteins, or nicotinamide (NIC) in an amount sufficient to maintain the cell in an undifferentiated state for a sufficient amount of time to achieve a desired result.

Pluripotent stem cells provide a potential resource for research and drug screening. At present, large-scale culturing of human ES cell lines is problematic and provides substantial challenges. A possible solution to these challenges is to passage and culture the human ES cells as single cells. Single cells are more amenable to standard tissue culture techniques, such as, for example, counting, transfection, and the like.

For example, Nicolas et al. provide a method for producing and expanding human ES cell lines from single cells that have been isolated by fluorescence-activated cell sorting following genetic modification by lentivirus vectors (Stem Cells Dev. 16:109-118, 2007).

In another example, US patent application US2005158852 discloses a method "for improving growth and survival of single human embryonic stem cells. The method includes the step of obtaining a single undifferentiated hES cell; mixing the single undifferentiated cell with an extracellular matrix to encompass the cell; and inoculating the mixture onto feeder cells with a nutrient medium in a growth environment".

In another example, Sidhu et al. (Stem Cells Dev. 15:61-69, 2006) describe the first report of three human ES cell clones, hES 3.1, 3.2 and 3.3, derived from the parent line hES3 by sorting of single-cell preparations by flow cytometry.

However, passage and culture of human ES cells as single cells leads to genetic abnormalities and the loss of pluripotency. Culture conditions are important in the maintenance of pluripotency and genetic stability. Generally, passage of human ES cell lines is conducted manually or with enzymatic agents such as collagenase, liberase or dispase.

For example, Draper et al. note the presence of "karyotypic changes involving the gain of chromosome 17q in three independent human embryonic stem cell lines on five independent occasions." (Nature Biotechnol. 22:53-54, 2004).

In another example, Buzzard et al. state, "we have only ever detected one karyotype change event . . . the culture methods used may have had some bearing on our results, given that our methods are distinctly different from those used by most other groups. Typically we passage human ES cells after 7 days by first dissecting the colony with the edge of a broken pipette . . . . No enzymatic or chemical methods of cell dissociation are incorporated into this method. We speculate that this may explain the relative cytogenetic resilience of hES (human ES) cells in our hands." (Nature Biotechnol. 22:381-382, 2004).

In another example, Mitalipova et al. state: "bulk passage methods . . . can perpetuate aneuploid cell populations after extended passage in culture, but may be used for shorter periods (up to at least 15 passages) without compromising the karyotypes . . . it may be possible to maintain a normal karyotype in hES cells under long-term manual propagation conditions followed by limited bulk passaging in experiments requiring greater quantities of hES cells than manual passage methods, alone, can provide". (Nature Biotechnol. 23:19-20, 2005).

In another example, Heng et al. state "the results demonstrated that the second protocol (trypsinization with gentle pipetting) is much less detrimental to cellular viability than is the first protocol (collagenase treatment with scratching).

This in turn translated to higher freeze-thaw survival rates." (Biotechnology and Applied Biochemistry 47:33-37, 2007).

In another example, Hasegawa et al. state, "we have established hESC sublines tolerant of complete dissociation. These cells exhibit high replating efficiency and also high cloning efficiency and they maintain their ability to differentiate into the three germ layers." (Stem Cells 24:2649-2660, 2006).

In another example, U.S. Patent application 61/030,544 provides methods and compositions for cell attachment to, cultivation on and detachment from a solid substrate surface containing from at least about 0.9% nitrogen to about at least 11% nitrogen and from at least about 12% oxygen to at least about 30% oxygen, and lacking an adlayer and feeder cells. In one embodiment of the present invention, the cells are treated with a compound capable of inhibiting Rho kinase activity.

There is a significant need for methods and compositions for the culture of cells, including pluripotent stem cells in the absence of feeder cells and an adlayer, while maintaining the pluripotency of the cells. The present invention provides methods for the growth, expansion and differentiation of pluripotent stem cells on planar substrates lacking an adlayer and a feeder cell layer, wherein the cells do not require treatment with a compound capable of inhibiting Rho kinase activity in order to bind to the planar substrate.

SUMMARY

In one embodiment, the present invention provides methods for the attachment, cultivation and differentiation of pluripotent stem cells to a planar substrate containing up to about 12% N, from at least about 12% O to at least about 55% O, a contact angle from about 18 degrees to about 32 degrees, and lacking an adlayer and a feeder cell layer.

DETAILED DESCRIPTION

Figure 1:
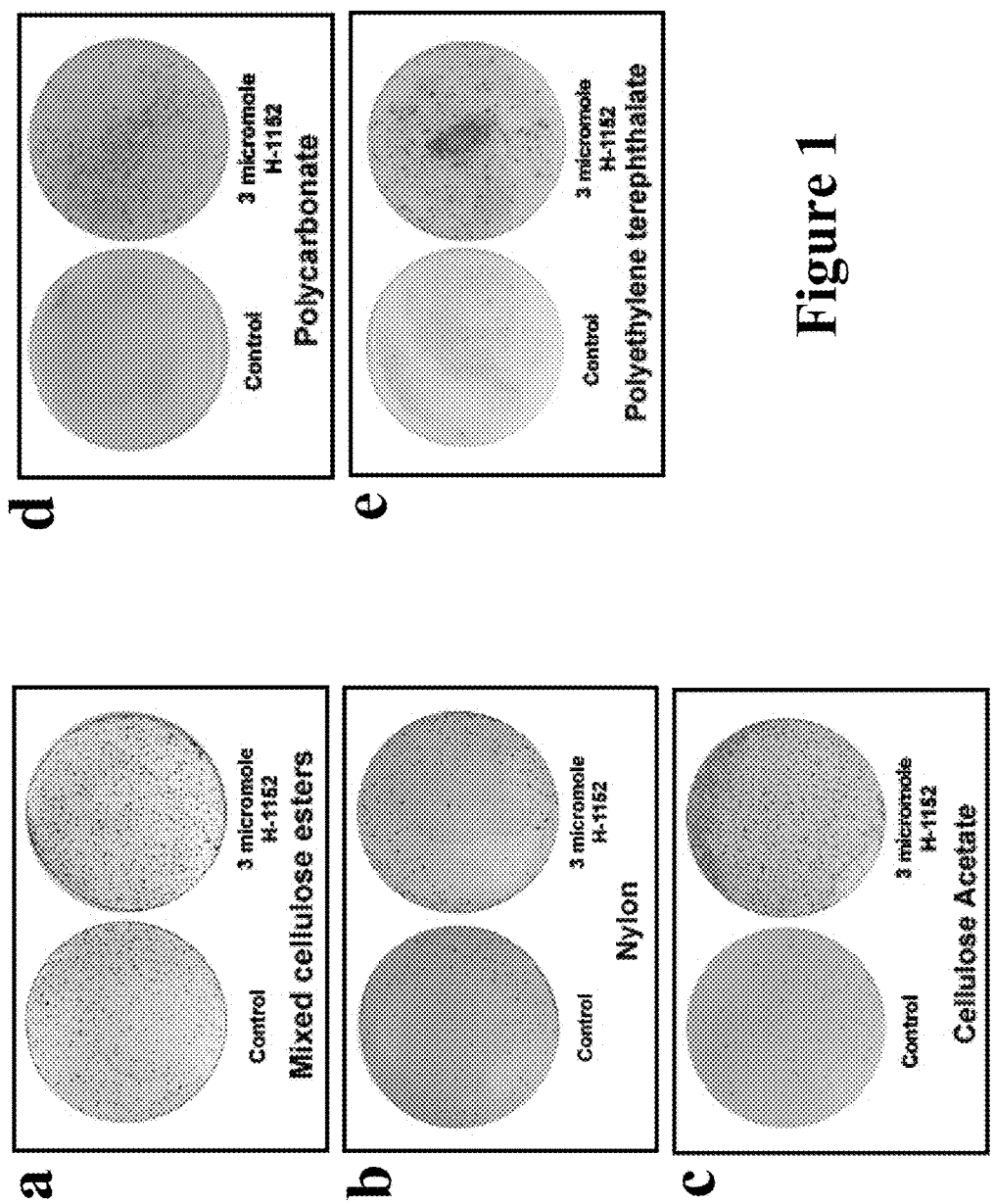
FIG. 1 shows the effect of the Rho kinase inhibitor H-1152 on the attachment of the human embryonic stem cell line H1 to planar substrates. Panel a): depicts cell attachment on mixed cellulose ester membranes (membrane No. 2 in Table 1). Panel b): depicts cell attachment on nylon membranes (membrane No. 4 in Table 1). Panel c): depicts cell attachment on cellulose acetate membranes (membrane No. 5 in Table 1). Panel d): depicts cell attachment on polycarbonate membranes (membrane No. 7 in Table 1). Panel e): depicts cell attachment on polyethylene terephthalate membranes (membrane No. 12 in Table 1).

For clarity of disclosure, and not by way of limitation, the detailed description of the invention is divided into the following subsections that describe or illustrate certain features, embodiments or applications of the present invention.

Definitions

"Adlayer" as used herein refers to a layer that is formed on a surface of a solid substrate, by attaching molecules to the surface by either covalent (also known as grafting) or non-covalent (also known as adsorption) bonds. Molecules used in making an adlayer can, for example, be proteinaceous molecules, which may include, for example, extracellular matrix proteins, amino acids and the like, and non-biological molecules, such as, for example, polyethyleneimine.

"β-cell lineage" refer to cells with positive gene expression for the transcription factor PDX-1 and at least one of the following transcription factors: NGN3, NKX2.2, NKX6.1, NEUROD, ISL1, HNF-3 beta, MAFA, PAX4, or PAX6. Cells expressing markers characteristic of the β cell lineage include β cells.

"Cells expressing markers characteristic of the definitive endoderm lineage", as used herein, refers to cells expressing at least one of the following markers: SOX17, GATA4, HNF3 beta, GSC, CER1, Nodal, FGF8, Brachyury, Mix-like homeobox protein, FGF4 CD48, eomesodermin (EOMES), DKK4, FGF17, GATA6, CXCR4, C-Kit, CD99, or OTX2. Cells expressing markers characteristic of the definitive endoderm lineage include primitive streak precursor cells, primitive streak cells, mesendoderm cells and definitive endoderm cells.

"Cells expressing markers characteristic of the pancreatic endoderm lineage", as used herein, refers to cells expressing at least one of the following markers: PDX1, HNF1 beta, PTF1 alpha, HNF6, NKX6.1, or HB9. Cells expressing markers characteristic of the pancreatic endoderm lineage include pancreatic endoderm cells, primitive gut tube cells, and posterior foregut cells.

"Definitive endoderm", as used herein, refers to cells which bear the characteristics of cells arising from the epiblast during gastrulation and which form the gastrointestinal tract and its derivatives. Definitive endoderm cells express the following markers: HNF3 beta, GATA4, SOX17, Cerberus, OTX2, goosecoid, C-Kit, CD99, and MIXL1.

"Pancreatic endocrine cell", or "pancreatic hormone expressing cell", as used herein, refers to a cell capable of expressing at least one of the following hormones: insulin, glucagon, somatostatin, and pancreatic polypeptide.

"Extraembryonic endoderm" as used herein refers to a population of cells expressing at least one of the following markers: SOX7, AFP, or SPARC.

"Extracellular matrix proteins" refers to proteinaceous molecules normally found between cells in the body or in the placenta. Extracellular matrix proteins can be derived from tissue, body fluids, such as, for example, blood, or media conditioned by non-recombinant cells or recombinant cells or bacteria.

"Markers" as used herein, are nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

"Mesendoderm cell" as used herein refers to a cell expressing at least one of the following markers: CD48, eomesodermin (EOMES), SOX-17, DKK4, HNF3 beta, GSC, FGF17, or GATA6.

"Pancreatic hormone secreting cell" as used herein refers to a cell capable of secreting at least one of the following hormones: insulin, glucagon, somatostatin, and pancreatic polypeptide.

"Pre-primitive streak cell" as used herein refers to a cell expressing at least one of the following markers: Nodal, or FGF8.

"Primitive streak cell" as used herein refers to a cell expressing at least one of the following markers: Brachyury, Mix-like homeobox protein, or FGF4.

Stem cells are undifferentiated cells defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent, meaning able to give rise to all embryonic and extraembryonic cell types; (2) pluripotent, meaning able to give rise to all embryonic cell types; (3) multipotent, meaning able to give rise to a subset of cell lineages, but all within a particular tissue, organ, or physiological system (for example, hematopoietic stem cells (HSC) can produce progeny that include HSC (self-renewal), blood cell restricted oligopotent progenitors and all cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g., spermatogenic stem cells).

Differentiation is the process by which an unspecialized ("uncommitted") or less specialized cell acquires the features of a specialized cell such as, for example, a nerve cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

"Surface" as used herein refers to the outermost layer of molecules of a solid substrate vessel or matrix intended for use in cell culture or analysis. The elemental composition, the roughness, and the wettability of the surface can be analyzed by X-Ray Photoelectron Spectroscopy (XPS), Atomic Force Microscopy (AFM), and contact angle measurement, respectively.

Various terms are used to describe cells in culture. "Maintenance" refers generally to cells placed in a growth medium under conditions that facilitate cell growth and/or division that may or may not result in a larger population of the cells. "Passaging" refers to the process of removing the cells from one culture vessel and placing them in a second culture vessel under conditions that facilitate cell growth and/or division.

A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but not limited to the seeding density, substrate, medium, growth conditions, and time between passaging.

Planar Substrates of the Present Invention

Planar substrates suitable for use in the present invention may be comprised of any material that is capable of providing a support onto which pluripotent cells may attach. For example, the planar substrate may be comprised of polycarbonate. Alternatively, the planar substrate may be comprised of polyethylene terephthalate (PETE). Alternatively, the planar substrate may be comprised of nylon. Alternatively, the planar substrate may be comprised of cellulose acetate. Alternatively, the planar substrate may be comprised of a mixed cellulose ester. Examples of planar substrates suitable for use in the present invention may be found in Table 1.

In one embodiment, the present invention provides methods for the attachment, cultivation and differentiation of pluripotent stem cells to a planar substrate containing up to about 12% N, from at least about 12% O to at least about 55% O, a contact angle from about 18 degrees to about 32 degrees, and lacking an adlayer and a feeder cell layer. The planar substrate containing from at least about 8% N to at least about 12% N, and from at least about 12% O to at least about 55% O may be a rough fibrous surface, or, alternatively, a smooth surface.

In one embodiment, the present invention provides a method to attach pluripotent stem cells to a planar substrate containing up to about 12% N, from at least about 12% O to at least about 55% O, a contact angle from about 18 degrees to about 32 degrees, and lacking an adlayer and a feeder cell layer, comprising the steps of:
  a. Obtaining a suspension of pluripotent stem cells, and
  b. Adding the cell suspension to the planar substrate and allowing the cells to attach.

In one embodiment, the pluripotent stem cells are maintained in culture after the cells attach to the surface. In one embodiment, the pluripotent stem cells are differentiated on the planar substrate after the cells attach to the surface.

In one embodiment, the attachment of pluripotent stem cells to a planar substrate containing up to about 12% N, from at least about 12% O to at least about 55% O, a contact angle from about 18 degrees to about 32 degrees, and lacking an adlayer and a feeder cell layer is enhanced by treating the cells with a compound capable of inhibiting Rho kinase activity. The compound capable of inhibiting Rho kinase activity may be removed from the cells after they have attached.

The compound capable of inhibiting Rho kinase activity is selected from the group consisting of: Y-27632, Fasudil, H-1152 and Hydroxyfasudil.

In one embodiment, the compound capable of inhibiting Rho kinase activity may be used at a concentration from about 0.1 µM to about 100 µM. In one embodiment, the at least one compound capable of inhibiting Rho kinase activity is used at a concentration of about 10 µM.

Characterization of the Planar Substrates of the Present Invention

In one embodiment, the elemental composition of the surface of the planar substrates of the present invention may be analysed by X-Ray Photoelectron Spectroscopy (XPS). XPS, also known as Electron Spectroscopy for Chemical Analysis (ESCA), is used as a method to determine what elements or atoms are present in the surface of a solid substrate (all elements in concentrations greater than 0.1 atomic percent can be detected, except hydrogen and helium), and to determine the bonding environment of such elements or atoms.

In one embodiment, the roughness of the surface of the planar substrates of the present invention may be analyzed by Atomic Force Microscopy (AFM). Surface atoms or molecules with a lateral resolution down to 1 Å and a vertical resolution down to 0.1 Å can be imaged by AFM.

In one embodiment, the wettability of the surface of the planar substrates of the present invention may be analyzed by measuring the contact angle. For example, contact angle measurement by the static sessile drop method provides information on the interaction between the surface of a solid substrate and a liquid. The contact angle describes the shape of a liquid drop resting on the surface of the solid substrate, and is the angle of contact of the liquid on the surface of the solid substrate, measured within the liquid at the contact line where liquid, solid, and gas meet. A surface with a water contact angle larger than 90° is termed hydrophobic, and a surface with water contact angle less than 90° is termed hydrophilic. On extremely hydrophilic surfaces, that is, surfaces that have a high affinity for water, a water droplet will completely spread (an effective contact angle of 0°).

In one embodiment, the negative charge density of the surface of the planar substrates of the present invention may be analyzed by measuring the reactivity of the surface with crystal violet. Crystal violet carries a positive charge, which enables it to bind to negatively charged molecules and parts of molecules, for example, negatively charged functional groups present on a polymer surface. A surface with a high crystal violet reactivity has a higher density of negative charges than a surface with a low crystal violet reactivity, given that the surfaces have the same roughness and thus area.

Pluripotent Stem Cells

Characterization of Pluripotent Stem Cells

Pluripotent stem cells may express one or more of the stage-specific embryonic antigens (SSEA) 3 and 4, and markers detectable using antibodies designated Tra-1-60 and Tra-1-81 (Thomson et al., Science 282:1145, 1998). Differentiation of pluripotent stem cells in vitro results in the loss of SSEA-4, Tra-1-60, and Tra-1-81 expression and increased expression of SSEA-1. Undifferentiated pluripotent stem cells typically have alkaline phosphatase activity, which can be detected by fixing the cells with 4% paraformaldehyde and then developing with Vector Red as a substrate, as described by the manufacturer (Vector Laboratories, Burlingame Calif.) Undifferentiated pluripotent stem cells also typically express OCT-4 and TERT, as detected by RT-PCR.

Another desirable phenotype of propagated pluripotent stem cells is a potential to differentiate into cells of all three germinal layers: endoderm, mesoderm, and ectoderm tissues. Pluripotency of stem cells can be confirmed, for example, by injecting cells into severe combined immunodeficient (SCID) mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered.

Sources of Pluripotent Stem Cells

The types of pluripotent stem cells that may be used include established lines of pluripotent cells derived from tissue formed after gestation, including pre-embryonic tissue (such as, for example, a blastocyst), embryonic tissue, or fetal tissue taken any time during gestation, typically but not necessarily before approximately 10 to 12 weeks gestation. Non-limiting examples are established lines of human embryonic stem cells or human embryonic germ cells, such as, for example the human embryonic stem cell lines H1, H7, and H9 (WiCell). Also contemplated is use of the compositions of this disclosure during the initial establishment or stabilization of such cells, in which case the source cells would be primary pluripotent cells taken directly from the source tissues. Also suitable are cells taken from a pluripotent stem cell population already cultured in the absence of feeder cells. Also suitable are mutant human embryonic stem cell lines, such as, for example, BG01v (BresaGen, Athens, Ga.). Also suitable are pluripotent stem cells derived from non-pluripotent cells, such as, for example, an adult somatic cell.

In one embodiment, human embryonic stem cells are prepared as described by Thomson et al. (U.S. Pat. No. 5,843,780; Science 282:1145, 1998; Curr. Top. Dev. Biol. 38:133 ff., 1998; Proc. Natl. Acad. Sci. U.S.A. 92:7844, 1995).

Culture of Pluripotent Stem Cells

In one embodiment, pluripotent stem cells are cultured on a layer of feeder cells or extracellular matrix protein that support the pluripotent stem cells in various ways, prior to culturing according to the methods of the present invention. For example, pluripotent stem cells are cultured on a feeder cell layer that supports proliferation of pluripotent stem cells without undergoing substantial differentiation. The growth of pluripotent stem cells on a feeder cell layer without differentiation is supported using (i) Obtaining a culture vessel containing a feeder cell layer; and (ii) a medium conditioned by culturing previously with another cell type, or a non-conditioned medium, for example, free of serum or even chemically defined.

In another example, pluripotent stem cells are cultured in a culture system that is essentially free of feeder cells, but nonetheless supports proliferation of pluripotent stem cells without undergoing substantial differentiation. The growth of pluripotent stem cells in feeder-cell free culture without differentiation is supported using (i) an adlayer on a solid substrate surface with one or more extracellular matrix proteins; and (ii) a medium conditioned by culturing previously with another cell type, or a non-conditioned medium, for example, free of serum or even chemically defined.

In an alternate embodiment, pluripotent stem cells are cultured on a planar surface comprising a mixed cellulose ester in a medium conditioned by culturing previously with another cell type, or a non-conditioned medium, for example, free of serum or even chemically defined.

Culture Medium:

An example of cell culture medium suitable for use in the present invention may be found in US20020072117. Another example of cell culture medium suitable for use in the present invention may be found in U.S. Pat. No. 6,642,048. Another example of cell culture medium suitable for use in the present invention may be found in WO2005014799. Another example of cell culture medium suitable for use in the present invention may be found in Xu et al (Stem Cells 22: 972-980, 2004). Another example of cell culture medium suitable for use in the present invention may be found in US20070010011. Another example of cell culture medium suitable for use in the present invention may be found in Cheon et al. (BioReprod DOI:10.1095/biolreprod.105.046870; 19 Oct. 2005). Another example of cell culture medium suitable for use in the present invention may be found in Levenstein et al. (Stem Cells 24: 568-574, 2006). Another example of cell culture medium suitable for use in the present invention may be found in US20050148070. Another example of cell culture medium suitable for use in the present invention may be found in US20050233446. Another example of cell culture medium suitable for use in the present invention may be found in U.S. Pat. No. 6,800,480. Another example of cell culture medium suitable for use in the present invention may be found in US20050244962. Another example of cell culture medium suitable for use in the present invention may be found in WO2005065354. Another example of cell culture medium suitable for use in the present invention may be found in WO2005086845.

Suitable culture media may also be made from the following components, such as, for example, Dulbecco's modified Eagle's medium (DMEM), Gibco #11965-092; Knockout Dulbecco's modified Eagle's medium (KO DMEM), Gibco #10829-018; Ham's F12/50% DMEM basal medium; 200 mM L-glutamine, Gibco #15039-027; non-essential amino acid solution, Gibco 11140-050; β-mercaptoethanol, Sigma #M7522; human recombinant basic fibroblast growth factor (bFGF), Gibco #13256-029.

Differentiation of Pluripotent Stem Cells

In one embodiment of the present invention, pluripotent stem cells are propagated in culture, while maintaining their pluripotency. Changes in pluripotency of the cells with time can be determined by detecting changes in the levels of expression of markers associated with pluripotency. Alternatively, changes in pluripotency can be monitored by detecting changes in the levels of expression of markers associated with differentiation or markers associated with another cell type.

In an alternate embodiment, pluripotent stem cells are propagated in culture and then treated in a manner that promotes their differentiation into another cell type. The other cell type may be a cell expressing markers characteristic of the definitive endoderm lineage. Alternatively, the cell type may be a cell expressing markers characteristic of the pancreatic endoderm lineage. Alternatively, the cell type may be a cell expressing markers characteristic of the pancreatic endocrine lineage. Alternatively, the cell type may be a cell expressing markers characteristic of the β-cell lineage.

Pluripotent stem cells treated in accordance with the methods of the present invention may be differentiated into a variety of other cell types by any suitable method in the art.

For example, pluripotent stem cells treated in accordance with the methods of the present invention may be differentiated into neural cells, cardiac cells, hepatocytes, and the like.

For example, pluripotent stem cells treated in accordance with the methods of the present invention may be differentiated into neural progenitors and cardiomyocytes according to the methods disclosed in WO2007030870.

In another example, pluripotent stem cells treated in accordance with the methods of the present invention may be differentiated into hepatocytes according to the methods disclosed in U.S. Pat. No. 6,458,589.

For example, pluripotent stem cells may be differentiated into cells expressing markers characteristic of the definitive endoderm lineage according to the methods disclosed in D'Amour et al., Nature Biotechnol. 23:1534-1541, 2005.

For example, pluripotent stem cells may be differentiated into cells expressing markers characteristic of the definitive endoderm lineage according to the methods disclosed in Shinozaki et al., Development 131:1651-1662, 2004.

For example, pluripotent stem cells may be differentiated into cells expressing markers characteristic of the definitive endoderm lineage according to the methods disclosed in McLean et al., Stem Cells 25:29-38, 2007.

For example, pluripotent stem cells may be differentiated into cells expressing markers characteristic of the definitive endoderm lineage according to the methods disclosed in D'Amour et al., Nature Biotechnol. 24:1392-1401, 2006.

Markers characteristic of the definitive endoderm lineage are selected from the group consisting of SOX17, GATA4, HNF3 beta, GSC, CER1, Nodal, FGF8, Brachyury, Mix-like homeobox protein, FGF4 CD48, eomesodermin (EOMES), DKK4, FGF17, GATA6, CXCR4, C-Kit, CD99, and OTX2. Suitable for use in the present invention is a cell that expresses at least one of the markers characteristic of the definitive endoderm lineage. In one aspect of the present invention, a cell expressing markers characteristic of the definitive endoderm lineage is a primitive streak precursor cell. In an alternate aspect, a cell expressing markers characteristic of the definitive endoderm lineage is a mesendoderm cell. In an alternate aspect, a cell expressing markers characteristic of the definitive endoderm lineage is a definitive endoderm cell.

For example, pluripotent stem cells may be differentiated into cells expressing markers characteristic of the pancreatic endoderm lineage according to the methods disclosed in D'Amour et al., Nature Biotechnol. 24:1392-1401, 2006.

Markers characteristic of the pancreatic endoderm lineage are selected from the group consisting of PDX1, HNF1 beta, PTF1 alpha, HNF6, HB9 and PROX1. Suitable for use in the present invention is a cell that expresses at least one of the markers characteristic of the pancreatic endoderm lineage.

In one aspect of the present invention, a cell expressing markers characteristic of the pancreatic endoderm lineage is a pancreatic endoderm cell.

Pluripotent stem cells may be differentiated into cells expressing markers characteristic of the pancreatic endocrine lineage by any method in the art.

For example, pluripotent stem cells may be differentiated into cells expressing markers characteristic of the pancreatic endocrine lineage according to the methods disclosed in D'Amour et al., Nature Biotechnol. 24:1392-1401, 2006.

For example, pluripotent stem cells may be differentiated into cells expressing markers characteristic of the pancreatic endocrine lineage, by the methods disclosed in D'Amour et al., Nature Biotechnol. 24: 1392-1401, 2006.

Markers characteristic of the pancreatic endocrine lineage are selected from the group consisting of NGN3, NEUROD, ISL1, PDX1, NKX6.1, PAX4, and PTF-1 alpha. In one embodiment, a pancreatic endocrine cell is capable of expressing at least one of the following hormones: insulin, glucagon, somatostatin, and pancreatic polypeptide. Suitable for use in the present invention is a cell that expresses at least one of the markers characteristic of the pancreatic endocrine lineage. In one aspect of the present invention, a cell expressing markers characteristic of the pancreatic endocrine lineage is a pancreatic endocrine cell. The pancreatic endocrine cell may be a pancreatic hormone-expressing cell. Alternatively, the pancreatic endocrine cell may be a pancreatic hormone-secreting cell.

In one aspect of the present invention, the pancreatic endocrine cell is a cell expressing markers characteristic of the β cell lineage. A cell expressing markers characteristic of the β cell lineage expresses PDX1 and at least one of the following transcription factors: NGN3, NKX2.2, NKX6.1, NEUROD, ISL1, HNF3 beta, MAFA, PAX4, and PAX6. In one aspect of the present invention, a cell expressing markers characteristic of the β cell lineage is a β cell.

The present invention is further illustrated, but not limited by, the following examples.

EXAMPLES

Example 1: Attachment of Human Embryonic Stem Cells to the Planar Substrates of the Present Invention The Rho kinase inhibitor Y26732 has been shown to enhance the attachment of human embryonic stem cells on surface modified plates (see U.S. Patent Application No. 61/030,544). The purpose of the studies of the present invention was to determine the ability of human embryonic stem cells to attach to other planar surfaces. The planar surfaces tested in the present invention are shown in Table 1.

Prior to testing, cells of the human embryonic stem cell line H1 cells were expanded on tissue culture plates coated with a 1:30 dilution of growth factor-reduced MATRIGEL®. Cells were seeded onto 100 mm culture dishes in 10 ml MEF conditioned media supplemented with 20 ng/ml bFGF (MEF-CM/bFGF). The cells were cultured at 37° C. in a humidified with a 5% $CO_2$ atmosphere. The media was changed everyday with fresh MEF-CM/bFGF. Once the cells reached approximately 80% confluence, the cells were passaged by treatment with 1 mg/ml LIBERASE for 5 minutes at 37° C. The digestion was stopped by removing enzyme from the dish and rinsing the cells with MEF-CM/bFGF. The cells were collected by manual scraping in 10 ml MEF-CM/bFGF and transferred to a 50-ml conical tube. The cells were centrifuged at 200×g (1000 rpm) on a tabletop centrifuge to form a pellet. After the supernatant was removed, the cells were re-suspended in 40 ml MEF-CM/bFGF and evenly distributed in four 100 mm culture dished coated with a 1:30 dilution of growth factor-reduced MATRIGEL®.

Cells of the human embryonic stem cell line H1 were seeded onto the various planar substrates set forth in Table 1, at a density of 100,000 cells/cm². The planar substrates lacked an adlayer and a fibroblast feeder cell layer. The cells were cultured in MEF-CM/bFGF as described above. The effect of the Rho kinase inhibitor H-1152 on the attachment of the cells to the planar substrates was determined 3 µM H-1152 was added to the medium used to seed the cells. Cells were allowed to attach for 24 hrs. After this time, the cells were fixed with 4% paraformaldehyde for 5 minutes at room temperature. The cells were then stained with 1% hematoxylin, and the number of cells was determined via light microscopy. Wells containing vehicle were included as a control.

The cells of the human embryonic stem cell line H1 attached to the following membranes in a Rho kinase inhibitor independent manner: mixed cellulose ester membrane (membrane No. 2, FIG. 1, panel a); nylon membrane (membrane No. 4, FIG. 1, panel b), and cellulose acetate membrane (membrane No. 5, FIG. 1, panel c). The attachment of cells to these membranes was enhanced by addition of 3 µM H-1152 (See FIG. 1, panels a-c).

Cells of the human embryonic stem cell line H1 required the presence of 3 µM H-1152 to attach to the following planar substrates: Polycarbonate membrane (membrane No. 7, FIG. 1, panel d) and Polyethylene terephthalate membrane (membrane No. 12, FIG. 1, panel e). Removal of H-1152 from the culture medium led to detachment of H1 cells from both types of membranes. No attachment was observed to these membranes in the absence of H-1152.

Example 2: The Effect of Rho Kinase Treatment on the Attachment of Human Embryonic Stem Cells to Planar Substrates Comprising Mixed Cellulose Esters (Membrane No. 1)

Cells of the human embryonic stem cell line H9 were cultured on MATRIGEL® coated dishes prior to experimental manipulation. Cells were seeded a mixed cellulose ester membrane (membrane No. 1) at a density of 150,000 cells/cm² in MEF conditioned medium. The planar substrate lacked an adlayer and a fibroblast feeder cell layer. The effect of the Rho Kinase inhibitor treatment on the attachment to the planar substrate was examined Cells were treated with 0, 10, or 20 µM Y26732. After 24 hours, the cells were fixed with 4% paraformaldehyde, rinsed with PBS, air dried, stained with crystal violet dye. The number of cells was determined via light microscopy. Wells containing vehicle were included as a control.

Figure 2:
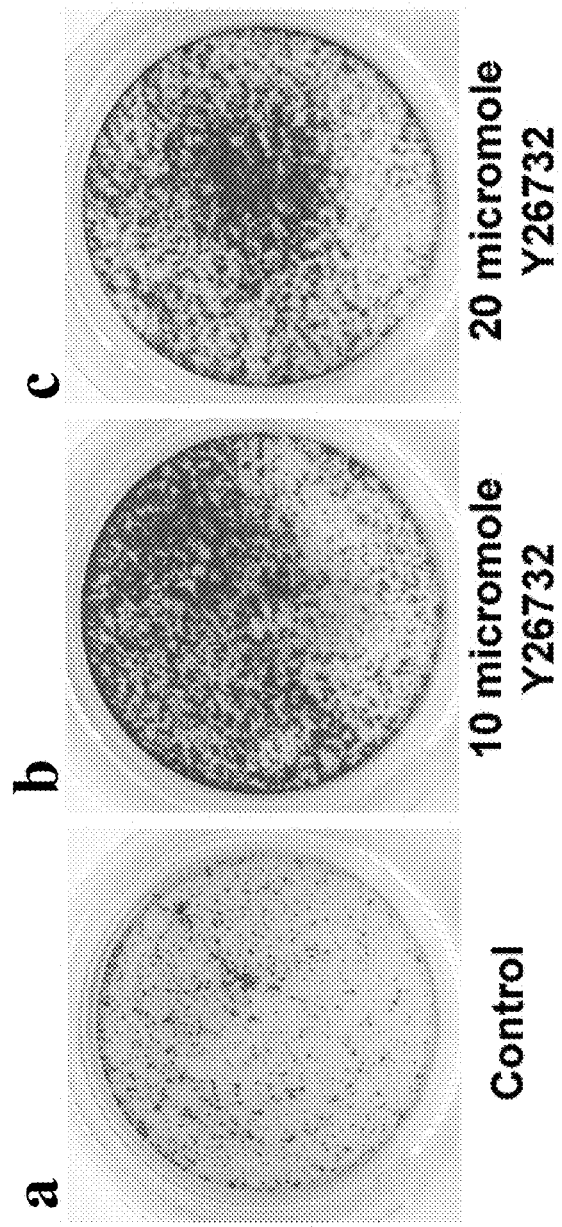
FIG. 2: shows the effect of the Rho kinase inhibitor Y-26732 on the attachment of the human embryonic stem cell line H9 to mixed cellulose ester membrane (membrane No. 1 in Table 1). Panel a): depicts cell attachment in a control well. Panel b): depicts cell attachment for cells treated with 10 µM Y-26732. Panel c): depicts cell attachment for cells treated with 20 µM Y-26732.

Cells were observed to attach to the planar substrate in the absence of Y26732 (FIG. 2, panel a). Addition of Y26732 increased the attachment of cells to the planar substrate, at 10 and 20 µM (FIG. 2, panels b and c). Removal of Y26732 from the culture medium for 24 hr did not result in the detachment of the cells from the planar substrate.

Figure 3:
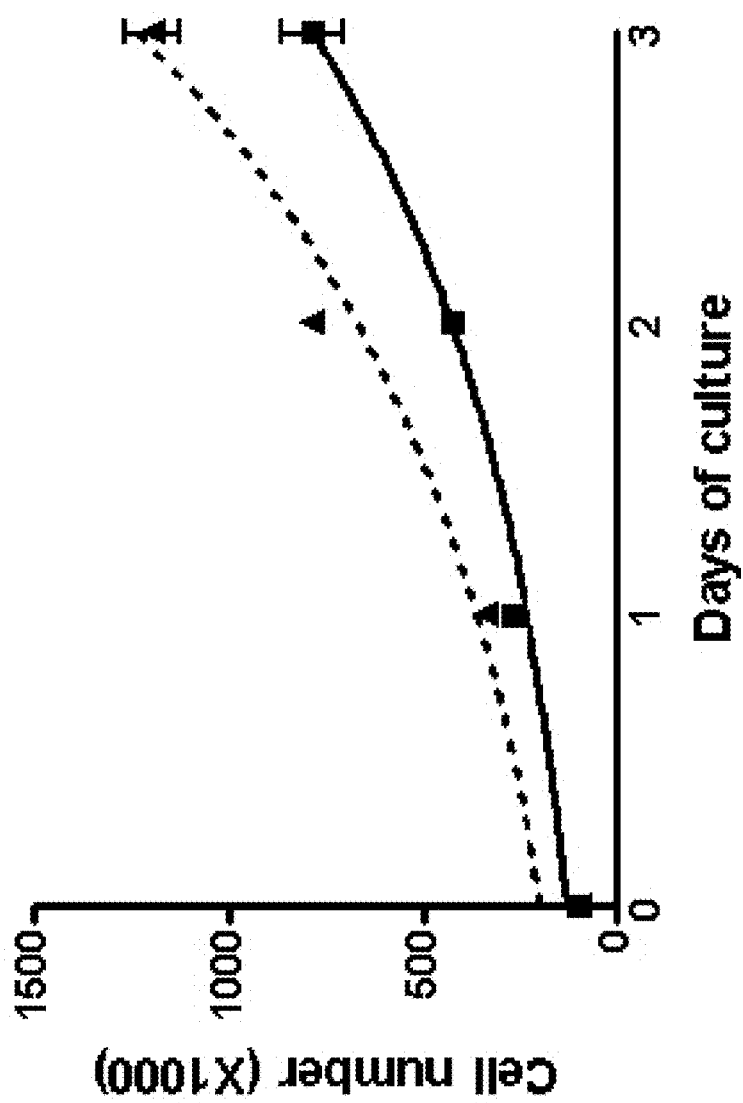
FIG. 3: shows the proliferation curves of the human embryonic stem cell line H1 on MATRIGEL® coated surface (solid line) and on mixed cellulose ester membranes (membrane No. 1 in Table 1) (dashed line).

Example 3: The Effect of Culture on Planar Substrate Membrane No. 1 on the Proliferation Rate of Human Embryonic Stem Cells The proliferation rate of cells of the human embryonic stem cell line cultured on MATRIGEL® coated dished and cells cultured on Membrane No. 1 was compared. Cells were seeded at equal densities on both substrates. Cells were released from the substrates by TrypLE treatment to create a single cell suspension to determine cell number. Samples of cells were taken at the times indicated in FIG. 3. Cells were observed to proliferate at comparable rates. The doubling time is about 1.151 day and 1.138 day on MATRIGEL® and on Membrane No. 1, respectively.

Example 4: Human Embryonic Stem Cells Maintain their Pluripotency for Three Passages on Planar Substrates Comprising Mixed Cellulose Esters (Membrane No. 1)

Cells of the human embryonic stem cell line H1 were seeded on a planar substrate comprising mixed cellulose ester membranes (membrane No. 1) at a density of 75,000 cells/cm² in MEF-CM containing 20 ng/ml bFGF. The cells were cultured for 5 or 6 days before passaging to reach approximately 75 to 90% confluency according to the methods described above. The culture medium was changed everyday. After culturing for 3 passages, the cells were collected and the expression of markers associated with pluripotency was determined by flow cytometry. As shown in Table 2, over 95% of cells maintained expression of cell surface markers associated with pluripotency, including Tral-60, Tral-81, SSEA-3, and SSEA-4, indicating the cells were still pluripotent.

Example 5: Human Embryonic Stem Cells Maintain a Stable Karyotype for Ten Passages on Planar Substrates Comprising Mixed Cellulose Esters (Membrane No. 1)

Figure 4:
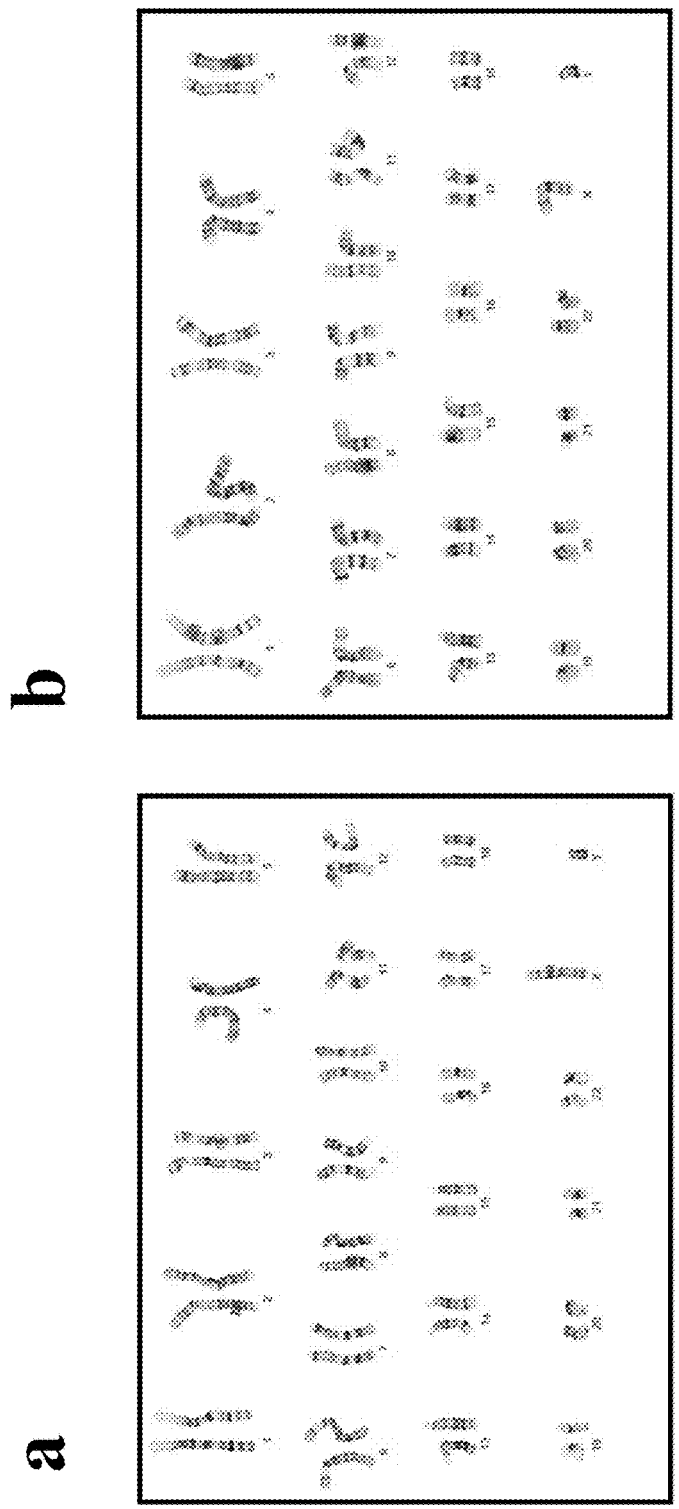
FIG. 4: shows the G-banded chromosomes from representative cells of the human embryonic stem cells of the line H1. Panel a): depicts the chromosomes from a cell cultured on MATRIGEL® coated surface for 10 passages. Panel b): depicts the chromosomes from a cell cultured on mixed cellulose ester membranes (membrane No. 1 in Table 1) for 10 passages.

Cells of the human embryonic stem cell line H1 were cultured either on MATRIGEL® coated culture plates or on mixed cellulose esters membrane for 10 passages. The cells were cultured according to the methods described above. The karyotype was determined by cytogenetic analysis by analyzing twenty G-banded metaphase cells. As shown in FIG. 4, the G-banded chromosomes of a representative cell cultured on MATRIGEL® coated culture plates (FIG. 4, panel a) and those of another cell cultured on mixed cellulose membrane (FIG. 4, panel b) demonstrate a normal male karyotype.

The karyotype was also determined by examining two hundred interphase nuclei by fluorescence in situ hybridization (FISH) using a chromosome 12p probe and a 17q probe to identify very small populations of cells with changes in chromosome 12 and 17 copy number that can not be detected by routine cytogenetics. In cells cultured on MATRIGEL® and on mixed cellulose esters membranes, no abnormal cells with trisomy 12 and/or 17 were detected.

Example 6: Human Embryonic Stem Cells are Able to Differentiate to Insulin-Producing Cells on Planar Substrates Comprising Mixed Cellulose Esters (Membrane No. 1)

Cells of the human embryonic stem cell line H1 were seeded on a planar substrate comprising mixed cellulose esters (Membrane No. 1) at a density of 150,000 cells/cm² in MEF conditioned medium containing 20 ng/ml bFGF. The cells were differentiated to insulin-producing cells by treating the cells according to the differentiation protocol outlined in Table 3. The cells were cultured in MEF conditioned medium containing 20 ng/ml bFGF for 3 to 4 days to reach approximately 75 to 90% confluency. The cells were treated in DMEM-F12 medium containing 2% Fatty-Acid Free Bovine Serum Albumin (FAF-BSA), 100 ng/ml activin A, and 20 ng/ml Wnt3A for two days, followed by treatment with DMEM-F12 medium, 2% Fatty-Acid Free Bovine Serum Albumin (FAF-BSA), and 100 ng/ml activin A for another two days. Next, the cells were treated in DMEM-F12 medium containing 2% BSA, 20 ng/ml FGF7, and 250 nM Cyclopamine-KAAD for three days, followed the treatment in DMEM-F12 medium containing 1% B27 supplement, 20 ng/ml FGF7, 250 nM Cyclopamine-KAAD, 2 µM retinoic acid (RA), and 100 ng/ml Noggin for 4 days. The cells were treated in DMEM-F12 medium containing 1% B27 supplement, 1 µM ALK5 inhibitor 2 (Axxora Cat. No: ALX-270-445-M001), 100 ng/ml Noggin, 100 ng/ml Netrin-4, 50 ng/ml Exendin-4, and 1 µM DAPT for 3 days. The cells were cultured in DMEM-F12 medium, 1% B27 supplement, and 1 µM ALK5 inhibitor 2 for 7 days and in DMEM-F12 medium containing 1% B27 supplement for another 7 days.

At the end of the differentiation protocol, RNA samples were collected to determine the expression of markers characteristic of the pancreatic endocrine lineage. A CT number for insulin of about 17 was observed. The corresponding CT value for GAPDH was about 19; these data suggests that the cells expressed high levels of insulin following treatment.

Example 7: Human Embryonic Stem Cells Attach to Planar Substrates Comprising Polycarbonate Membranes in a Rho Kinase Inhibitor Dependent Manner Cells of the human embryonic stem cell line H9 were seeded onto a planar substrate comprising polycarbonate (Membrane No. 7) at a density of 150,000 cells/cm² in MEF conditioned medium. The effect of Rho kinase inhibitor treatment on attachment was examined: The Rho Kinase inhibitor Y26732 was added to the culture medium at concentration of 0, 10, or 20 µM. After 24 hours, the cells on the membrane were fixed with 4% paraformaldehyde at room temperature, rinsed with PBS, air dried, stained with crystal violet dye. The number of cells was determined via light microscopy. Wells containing vehicle were included as a control.

Figure 5:
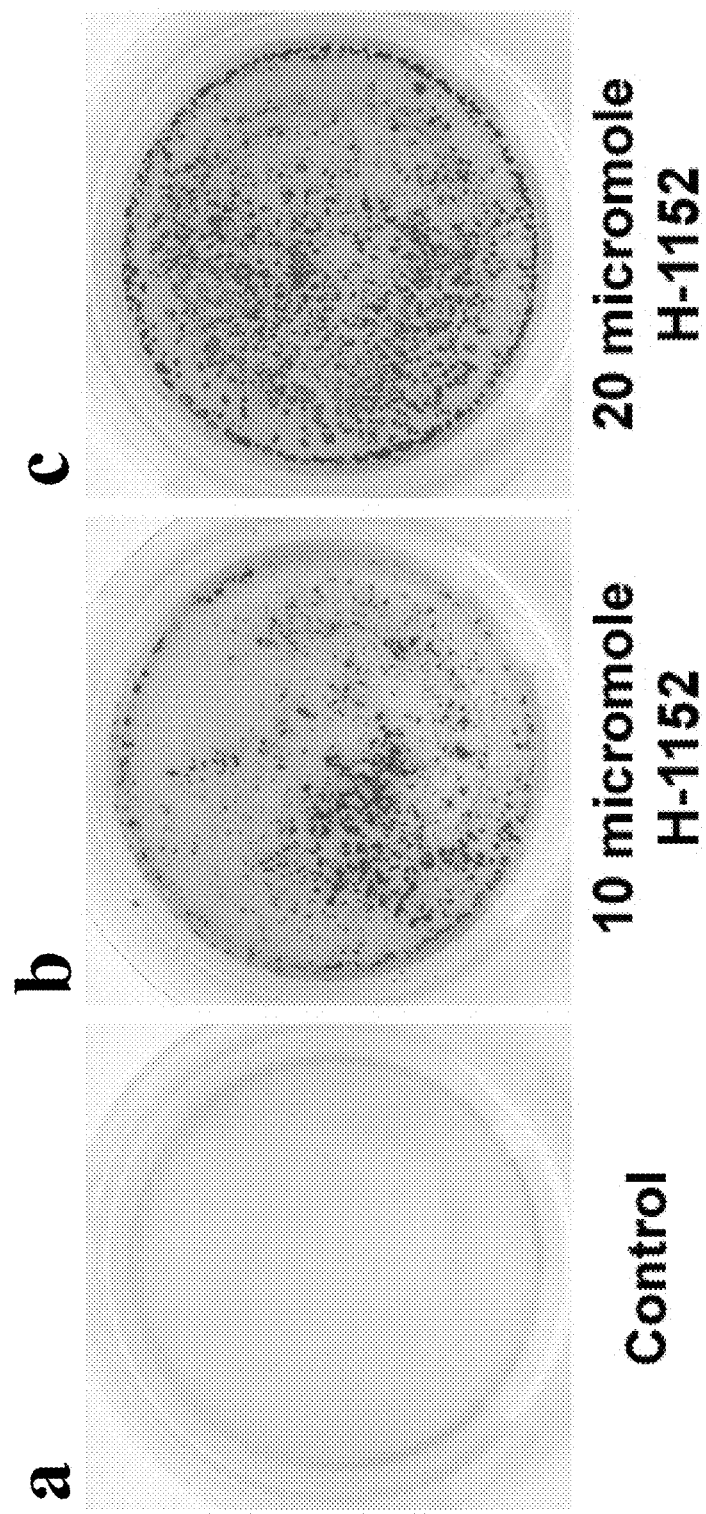
FIG. 5: shows the effect of the Rho kinase inhibitor Y26732 on cells of the human embryonic stem cell line H9 on the attachment to polycarbonate membranes (membrane No. 7 in Table 1). Panel a): depicts cell attachment in a control well. Panel b): depicts cell attachment following treatment with 10 µM Y-26732. Panel c): depicts cell attachment following treatment with 20 µM Y-26732.

The cells do not attach to the membrane in control dishes (FIG. 5, panel a). Addition of Y26732 resulted in the attachment of the cells on the membranes (FIG. 5, panels b and c).

In a separate experiment, the effect of the Rho kinase inhibitor H-1152 on the attachment of cells of the human embryonic stem cell line H1 to Membrane No. 7 was determined. The cells were seeded on a planar substrate comprising polycarbonate membranes (membrane No. 7) at a density of 150,000 cells/cm² in MEF-CM containing 20 ng/ml bFGF. The Rho Kinase inhibitor H-1152 was added to the culture medium at concentration of 0, 0.03, 0.1, 0.3, 1, and 3 µM. After 24 hours, the cells on the membrane were fixed with 4% paraformaldehyde, rinsed with PBS, air dried, stained with crystal violet dye. The number of cells was determined via light microscopy. Wells containing vehicle were included as a control.

Figure 6:
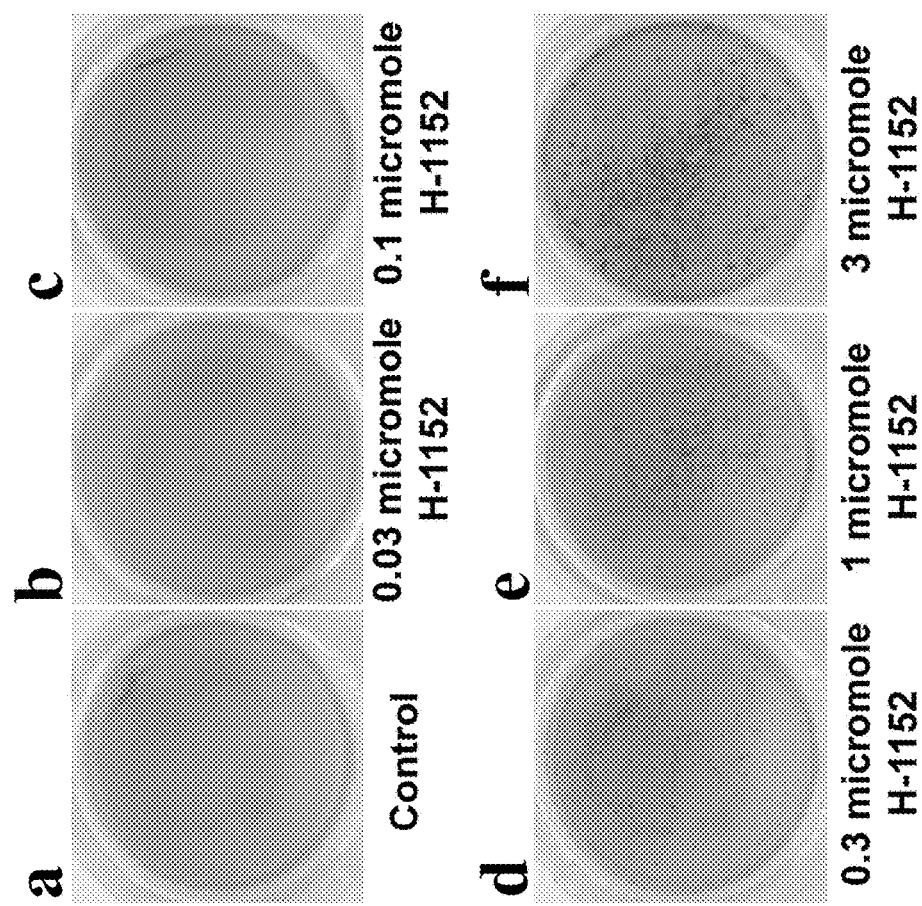
FIG. 6 shows the effect of the Rho kinase inhibitor H-1152 on the attachment of cells of the human embryonic stem cell line H1 to polycarbonate membranes (membrane No. 7 in Table 1). Panel a): depicts cell attachment in a control well. Panel b): depicts cell attachment when 0.03 µM of H-1152 was added to the medium. Panel c): depicts cell attachment when 0.1 µM of H-1152 was added to the medium. Panel d): depicts cell attachment when 0.3 µM of H-1152 was added to the medium. Panel e): depicts cell attachment when 1 µM of H-1152 was added to the medium. Panel f): depicts cell attachment when 3 µM of H-1152 were added to the medium.

The cells do not attach to the membrane in the control dish (FIG. 6, panel a) and in the dishes with 0.03 or 0.1 µM of H-1152 (FIG. 6, panels b and c). However, attachment was observed in cultures treated with 0.3, 1, and 3 µM of H-1152 (FIG. 6, panels d-f).

Figure 7:
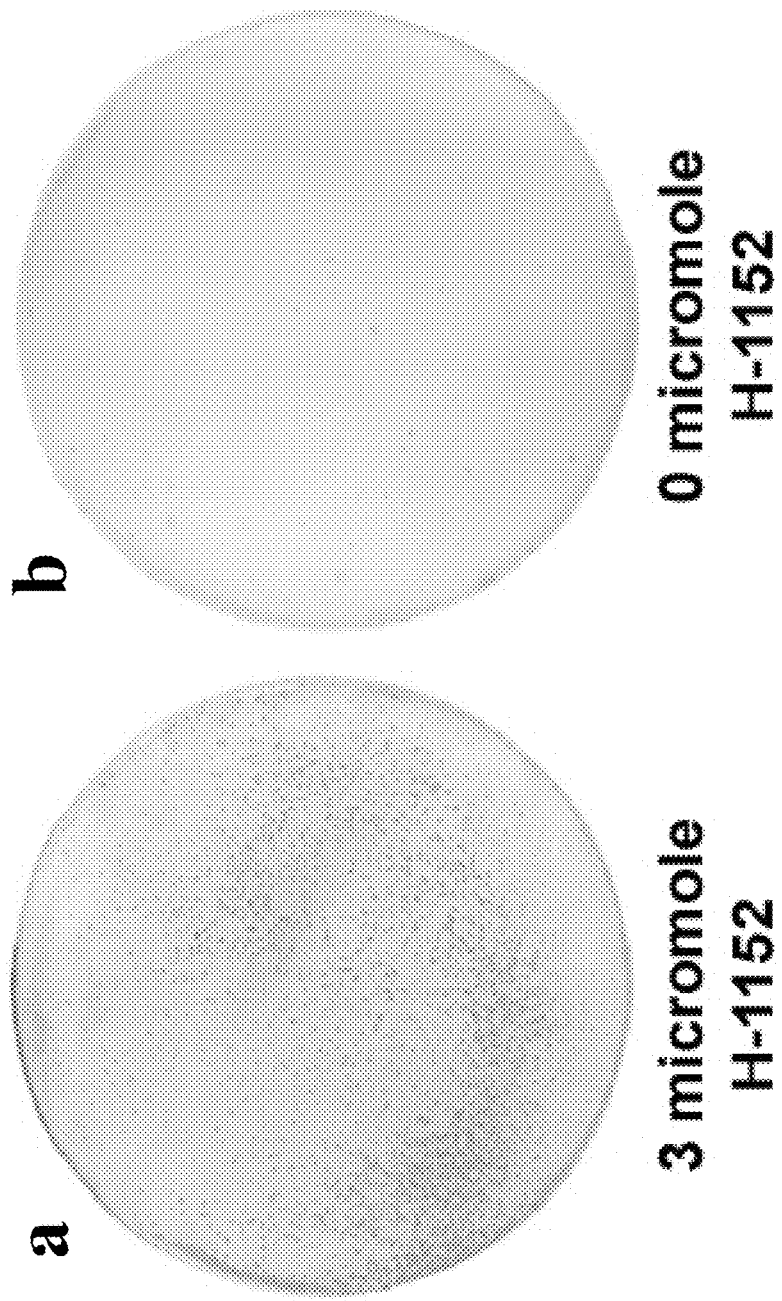
FIG. 7 shows the detachment of cells of the human embryonic stem cell line H1 from polycarbonate membranes (membrane No. 9 in Table 1) following the removal of Rho kinase inhibitor H-1152 from the cell culture medium. Panel a): depicts the attachment of cells when 3 µM of H-1152 were maintained in the culture medium. Panel b): depicts detachment of cells when H-1152 was removed from the culture medium.

Example 8: Removal of the Rho Kinase Inhibitor from the Culture Medium Results in the Detachment of Human Embryonic Stem Cells from Planar Substrates Comprising Polycarbonate Membranes Cells of the human embryonic stem cell line H1 were seeded on to a planar substrate comprising polycarbonate (Membrane No. 9) at a density of 100,000 cells/cm², in MEF conditioned medium containing 20 ng/ml bFGF and 3 µM of the Rho kinase inhibitor H-1152. The cells were cultured for 24 hr. After this time, the culture medium was replaced with MEF conditioned medium containing 20 ng/ml bFGF, lacking H-1152. After 24 hours, the cells on the membrane were fixed with 4% paraformaldehyde, rinsed with PBS, air dried, stained with crystal violet dye. The number of cells was determined via light microscopy. Wells containing H-1152 were included as a control. Removal of H-1152 from the culture medium resulted in the detachment of cells from the planar substrate (FIG. 7).

Example 9: Porosity of the Planar Substrate Affects the Attachment of Human Embryonic Stem Cells Cells of the human embryonic stem cell line H1 at passage 42 were seeded onto the following planar substrates: Membrane No. 10 (pore size 0.4 µm); and Membrane No. 11 (pore size 3 µm). Cells were seeded at a density of 100,000 cells/cm², in MEF conditioned medium containing 20 ng/ml bFGF. The effect of Rho kinase inhibition on the attachment of the cells to the planar substrates was also examined. The cell culture medium was supplemented with 0.3 µM H-1152. After 24 hours, the culture medium was replaced with MEF conditioned medium containing 20 ng/ml bFGF, lacking H-1152. After another 24 hours culture, the cells on the membrane were fixed with 4% paraformaldehyde, rinsed with PBS, air dried, stained with crystal violet dye. Wells containing 1 µM H-1152 were included as a control. The number of cells was determined via light microscopy. Wells containing vehicle were included as a control.

Figure 8:
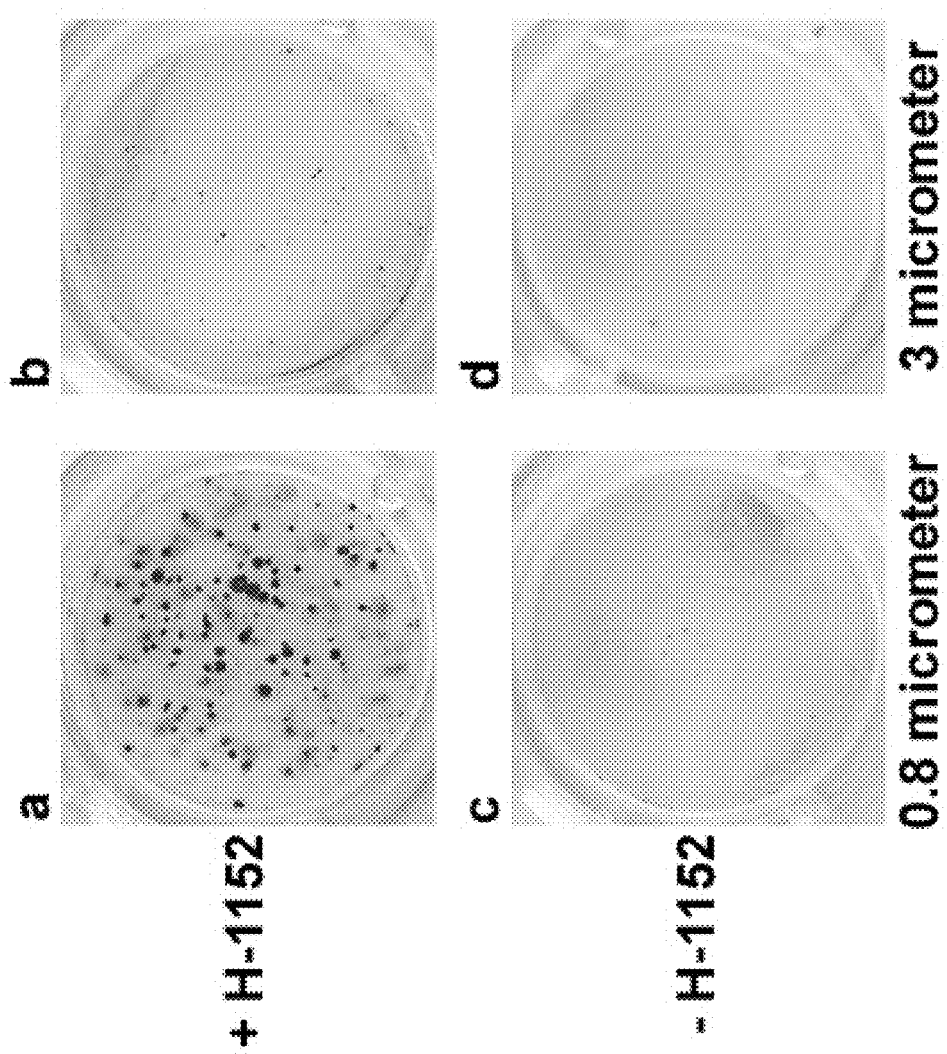
FIG. 8 shows the effect of membrane pore size and Rho kinase inhibitor treatment on the attachment of the human embryonic stem cell line H1 to the planar substrates comprising the following: polycarbonate membrane No. 10 in Table 1 in panel a and c; and polycarbonate membrane No. 11 in Table 1 in panel b and d). Panels a and b): depict the attachment of cells when 3 µM of H-1152 were maintained in the culture medium. Panels c and d): depict the detachment of cells when H-1152 was removed from the culture medium.

A greater number of cells attached to Membrane No. 10 (FIG. 8, panel a) than Membrane No. 11 (FIG. 8, panel b). Presence of 1 µM H-1152 in the culture medium is required to maintain the attachment of H1 cells on the membranes (FIG. 8, panel a and b). Removal of H-1152 from the culture medium resulted in detachment of cells from Membrane No. 10 and Membrane No. 11 (FIG. 8, panel c and d).

Figure 9:
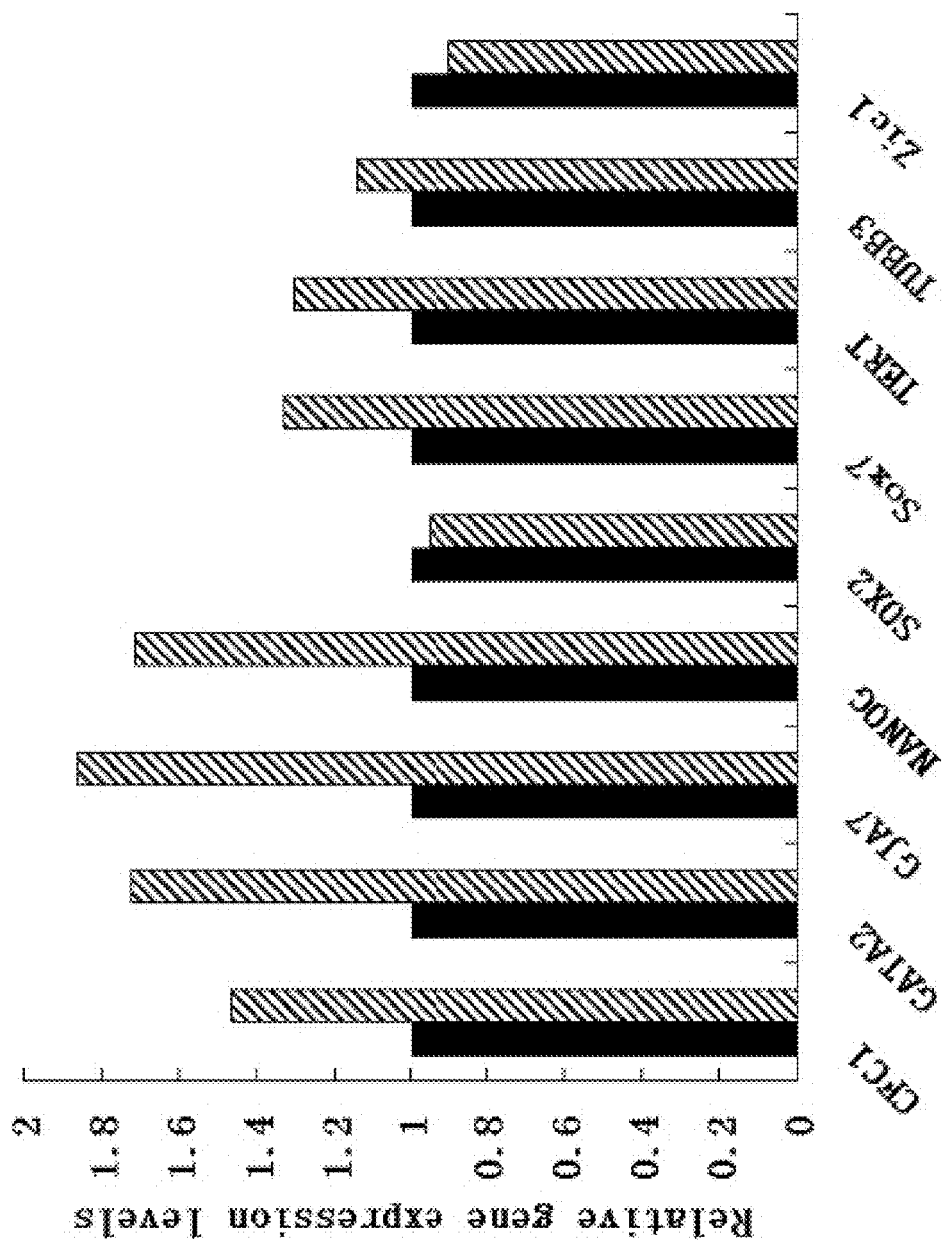
FIG. 9 shows the maintenance of the expression of markers associated with pluripotency in cells of the human embryonic stem cell line H1 cultured on polycarbonate membranes (membrane No. 8 in Table 1) for three passages. Expression of the genes indicated in the figure was determined by real-time PCR. The solid bars represent data obtained from the undifferentiated human embryonic stem cell line H1. Hashed bars represent data obtained from the cells cultured on polycarbonate membranes.

Example 10: Human Embryonic Stem Cells Maintain their Pluripotency After Multiple Passages on Planar Substrates Comprising Polycarbonate Membranes Cells of the human embryonic stem cell line H1 were seeded on to a planar substrate comprising polycarbonate membrane (Membrane No. 8). Cells were cultured in MEF conditioned medium containing 20 ng/ml bFGF, supplemented with 3 µM H-1152. The cell culture medium was changed daily. Cells were passaged by the removal of H-1152 from the medium, and the cells were removed from the planar substrate by gentle swirling. The cells were cultured for 3 passages and collected for flow cytometry and quantitative RT-PCR analysis. As shown in Table 4, over 95% of the cells expressed cell surface markers associated with pluripotency, including Tral-60, Tral-81, SSEA-3, and SSEA-4, as determined by flow cytometry. FIG. 9 shows the results of quantitative RT-PCR, indicating multiple genes expressed in the H1 cultured on polycarbonate membranes for 3 passages are at comparable levels as in undifferentiated H1 cells.

In a separate study, cells of the human embryonic stem cell line H1 were seeded on to a planar substrate comprising polycarbonate membrane (Membrane No. 8). Cells were cultured in MEF conditioned medium containing 20 ng/ml bFGF, supplemented with 1 μM H-1152. The cell culture medium was changed daily. Cells were passaged by the removal of H-1152 from the medium, and the cells were removed from the planar substrate by gentle swirling. The cells were cultured for 9 passages and collected for flow cytometry. As shown in Table 5, over 95% of the cells express cell surface markers associated with pluripotency, including Tral-60, Tral-81, SSEA-3, and SSEA-4.

An alternative method to assess pluripotency is via the ability of the cells to form embryoid bodies. Cells of the human embryonic stem cell line H1 were seeded on to planar substrates comprising polycarbonate membranes (Membrane No. 8). The cells were cultured in MEF conditioned medium containing 20 ng/ml bFGF, supplemented with 3 μM H-1152. The cell culture medium was changed daily. Cells were passaged by the removal of H-1152 from the medium, and the cells were removed from the planar substrate by gentle swirling. The cells were cultured for 12 passages.

Figure 10:
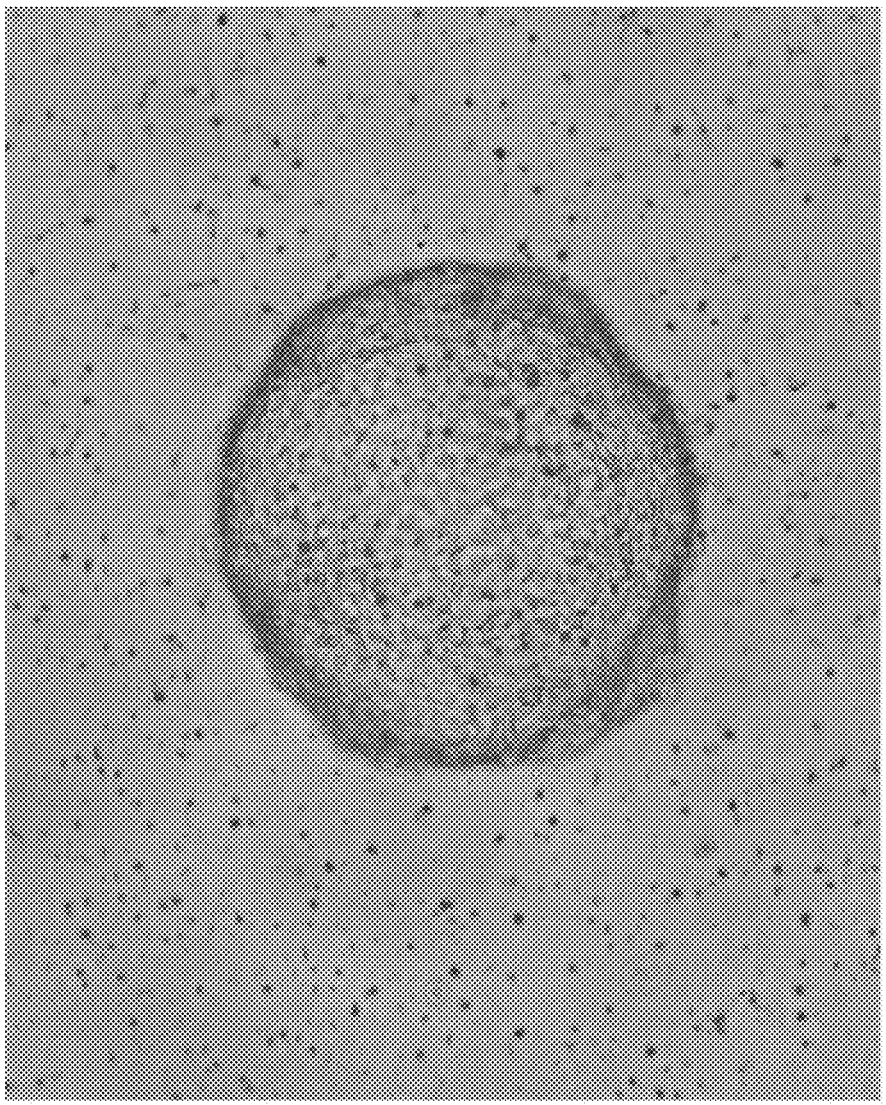
FIG. 10 shows the ability of cells of the human embryonic stem cell line H1 to form embryoid bodies following culture for 12 passages on polycarbonate membranes (membrane No. 8 in Table 1). The figure shows representative data from a single experiment.

Embryoid body formation was achieved by the following protocol. The H1 cells were collected and cultured in DMEM/F12 medium supplemented with 20% fetal bovine serum in Ultra Low Cluster Plate (Corning Cat. No: 3471). The cells were fed every other day by changing 50% of the medium. Embryoid bodies were formed after 14 days (FIG. 10).

Example 11: Human Embryonic Stem Cells are Capable of Forming Definitive Endoderm after Cultured on Planar Substrates Comprising Polycarbonate Membranes Cells of the human embryonic stem cell line H1 were seeded on to a planar substrate comprising polycarbonate (Membrane No. 8). The cells were initially cultured in MEF conditioned medium containing 20 ng/ml bFGF, supplemented with 3 μM H-1152. The cells were then cultured in MEF conditioned medium containing 20 ng/ml bFGF, supplemented with 1 μM H-1152 for 10 passages prior to experimental manipulation.

The cells were then seeded onto 100 mm tissue culture plates, coated with a 1:30 dilution of MATRIGEL®. The cells were cultured in MEF conditioned medium containing 20 ng/ml bFGF for 3 days. Next, the cells were treated in DMEM/F12, supplemented with 2% fatty acid free Bovine Serum Albumin, 100 ng/ml activin A, and 20 ng/ml Wnt3a for two days and then treated with DMEM/F12, supplemented with 2% fatty acid free Bovine Serum Albumin, and 100 ng/ml activin A for another two days. After this time, the cells were released by TRYPLE treatment to form a single cell suspension and the expression of markers characteristic of the definitive endoderm lineage was determined by flow cytometry.

Over 90% of the cells are CD99 and CXCR4 (CD184) double positive and 12% of the cells are CD9 positive CXCR4 negative, as shown in Table 6. These data suggest that the cells retain the capacity to differentiate into definitive endoderm.

Example 12: Physical Properties of the Planar Substrates of the Present Invention The surface chemistry was determined on the planar substrates of the present invention. Tables 7-10 depict the X-ray Photoelectron spectroscopy (XPS) analysis and contact angle. For XPS, an analysis depth of approximately 50-100 Å was used. Typically, 95% of the signal originates from within this depth.

Membranes 1-3 contained similar concentrations of oxygen, carbon (mainly as C—O, and C—(C,H), probably O—C—O), and nitrogen (as $NO_3$, $NO_2$, and possibly C—N, and $R_4$—$N^+$). Membrane 3 also contained trace concentrations of $Na^+$ and $SO_x$ and a higher concentration of C—(C, H). Membrane 4 contained C—(C,H), C—(O,N), and (O,N)—C=O and possibly a trace of sodium. Membrane 5 contained mainly C—O and also C—(C,H) and O—C—O and/or O—C=O. Trace concentrations of $Na^+$ and $SO_x$ were also detected. Membranes 6-11 contained C—(C,H), C—O, O—C=O, C—N, CO3, p-p*, and trace concentrations of $R_4$—$N^+$, $SO_x$, and either $Na^+$ or $Cr^{3+}$. The surface of membrane 6 may also contain a trace concentration of chlorine. Trace concentrations of chromium were detected only on membranes 10 and 11, while $Na^+$ was detected on membranes 6-9. The surface of membrane 12 contained C—(C,H), C—O, O—C=O, and pi-pi* consistent with PET. Trace concentrations of nitrogen and sodium were also detected.

Figure 11:
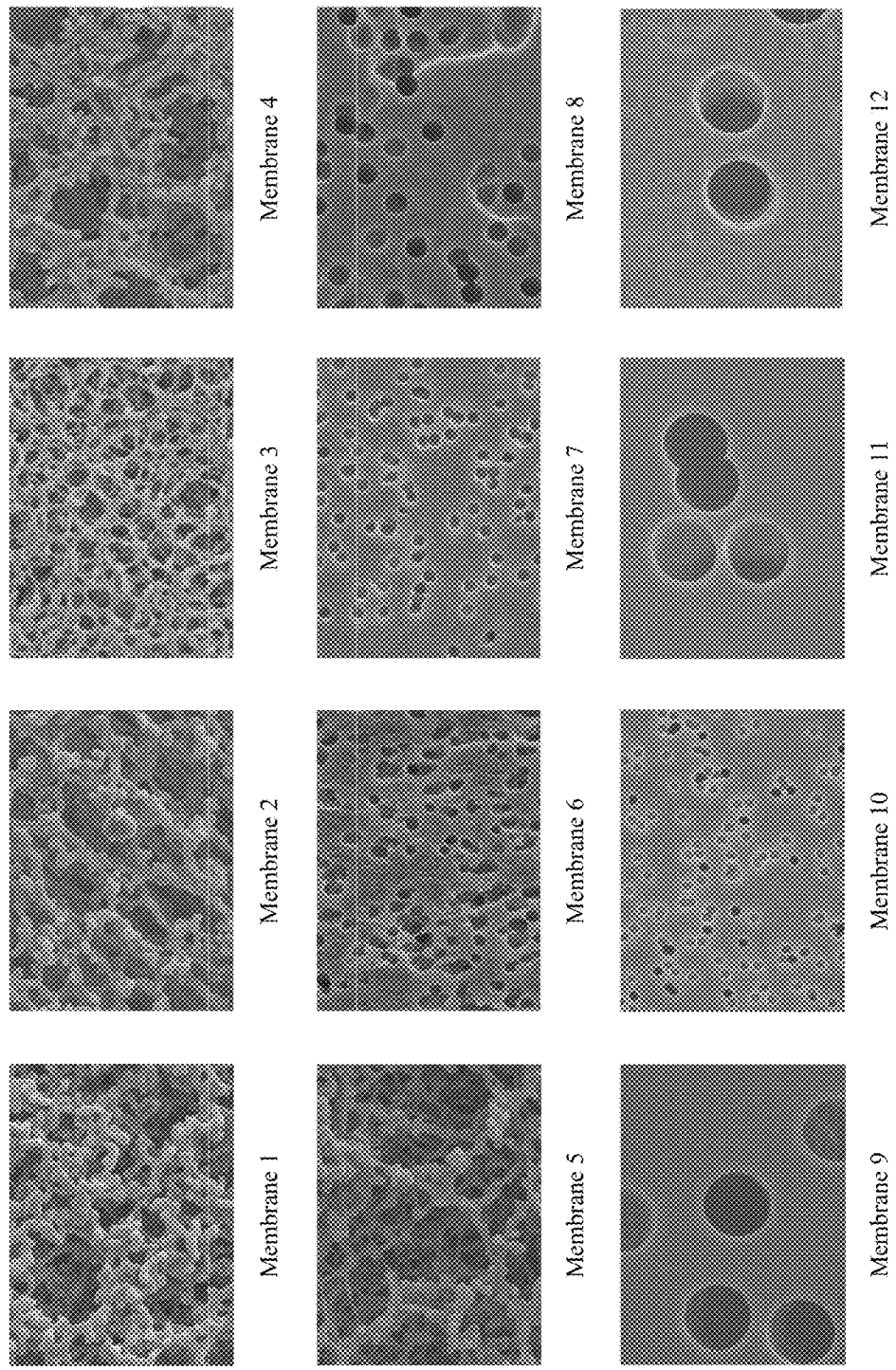
FIG. 11 shows scanning electron micrographs of the planar substrates of the present invention.

FIG. 11 shows the scanning electron micrographs of the planar substrates of the present invention. Two types of morphologies were observed. One type was characterized by an open network of fibers. The second type was characterized by a smooth sheet with circular holes dispersed across the surface.

Table 10 shows the contact angle measurements from the surfaces of the present invention. Surfaces 1 through 5 had contact angle measurements from about 18° to about 32°. Pluripotent stem cells did not require the presence of an inhibitor of Rho kinase activity in order to attach to surfaces 1-5.

Surfaces 6 through 12 had contact angle measurements greater than 32°. Pluripotent stem cells required the presence of an inhibitor of Rho kinase activity in order to attach to these surfaces.

Figure 12:
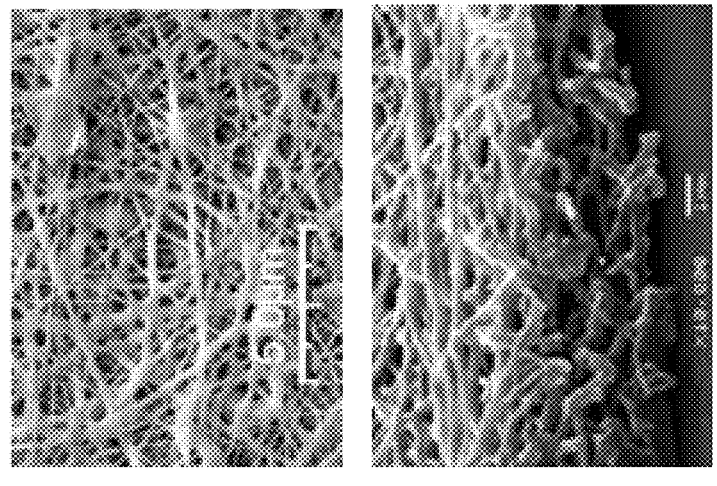
FIG. 12 shows scanning electron micrographs of the ULTRAWEB™ planar substrate.
Figure 13:
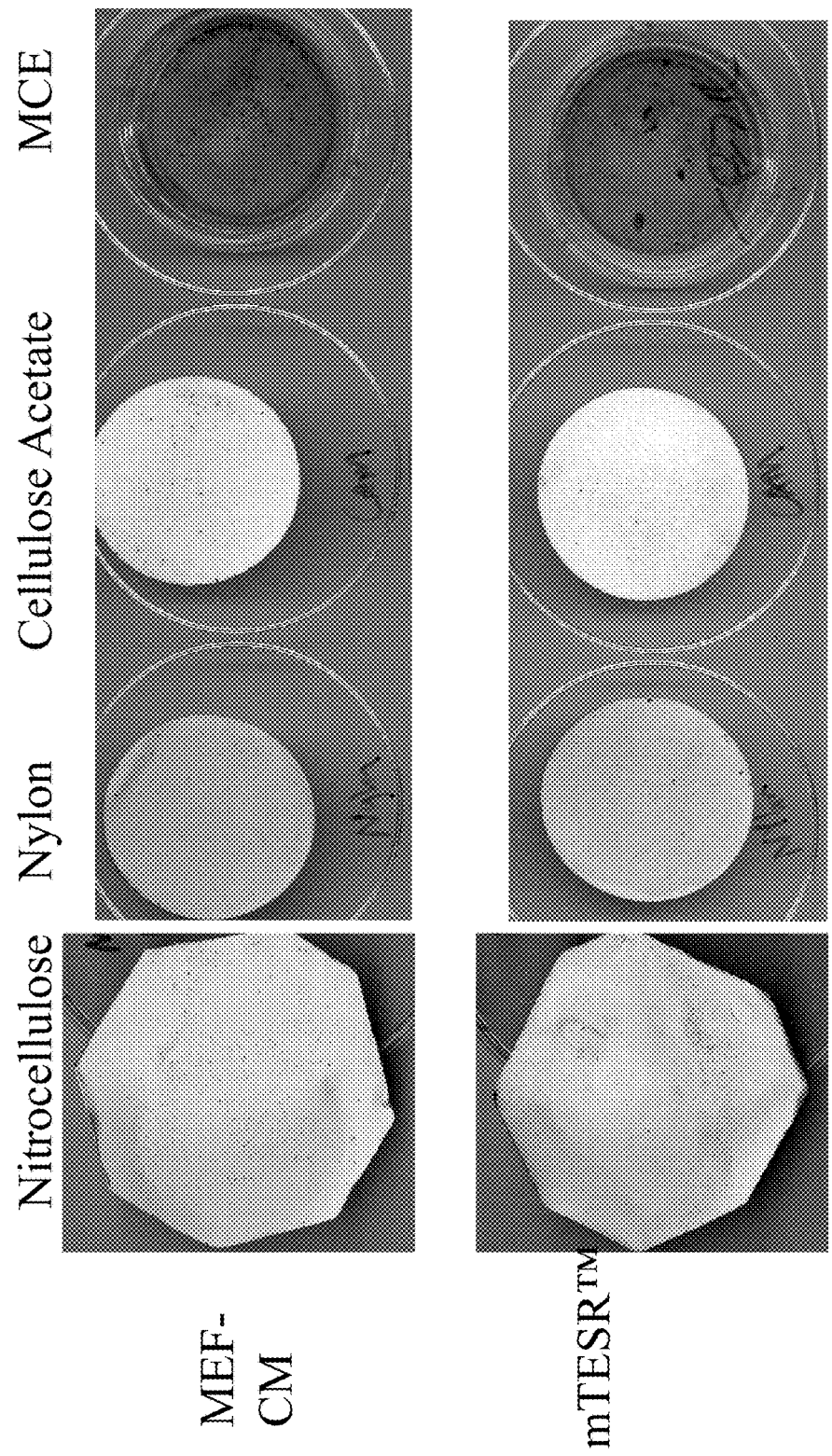
FIG. 13 shows the effect of the defined medium mTESR™ on the binding of cells of the human embryonic stem cell line H1 to various planar substrates.

Example 13: Attachment of Pluripotent Stem Cells to a Planar Substrate Consisting of a Polyamine The planar substrate consisting of polyamine was manufactured according to the methods disclosed in U.S. Pat. No. 6,743,273, and Schindler M et al, Biomaterials 26(28): 5624-5631; 2005. The planar substrate is available commercially, sold under the trademark ULTRAWEB™. ULTRAWEB™ synthetic surfaces are composed of randomly orientated electrospun polyamide nanofibers with an average fiber diameter of 280 nm. The fiber size distribution is between 200 and 400 nm. The first ULTRAWEB™ surface tested had a slightly hydrophilic surface (catalogue #3870XX1) while the second surface, surface (catalogue #3871XX1) was slightly hydrophilic and was coated with a polyamine material which provided the nanofibers with a free amine groups for a net positive charge. Both surfaces are highly effective at protein absorption through hydrophobic interactions. 5 micron resolution and 10,000× magnification scanning electron micrographs are shown in FIG. 12. However, cells of the human embryonic stem cell line H1 were unable to attach to either of the UTRAWEB™ surfaces tested.

est binding of cells using mTESR™ was Membrane 4, followed by Membrane 5, which was equal to nitrocellulose, followed by Membrane 1.

TABLE 1

Characterization of membranes suitable for use in the present invention.

| Membrane | Vendor | Catalog Number | Chemical composition | Hydrophobicity | Porosity | Surface | BSA binding capacity | Attachment of hES cells |
|---|---|---|---|---|---|---|---|---|
| 1 | Millipore | PIHA03050 | Mixed cellulose esters | Hydrophilic | 0.45 micrometer | Rough, fibrous | Greater than 160 micrograms per centimeter square | Rho kinase independent |
| 2 | Pall | 66276 | Mixed cellulose esters | Hydrophilic | 0.8 micrometer | Rough, fibrous | | Rho kinase independent |
| 3 | Sterlitech | MCE4525100 | Mixed cellulose esters | Hydrophilic | 0.45 micrometer | Rough, fibrous | Approximately 160 micrograms per centimeter square | Rho kinase independent |
| 4 | Sterlitech | NY4525100 | Nylon | Hydrophilic | 0.45 micrometer | Rough, fibrous | Greater than 120 micrograms per centimeter square | Rho kinase independent |
| 5 | Sterlitech | CA0225100 | Cellulose Acetate | Hydrophilic | 0.2 micrometer | Rough, fibrous | 3.8 micrograms per centimeter square | Rho kinase independent |
| 6 | Sterlitech | PCT0425100 | Polycarbonate | Hydrophilic | 0.4 micrometer | Smooth, thin, glass-like | Less than 5 micrograms per centimeter square | Rho kinase dependent |
| 7 | Millipore | PIHP03050 | Polycarbonate | Hydrophilic | 0.4 micrometer | Smooth, thin, glass-like | Less than 5 micrograms per centimeter square | Rho kinase dependent |
| 8 | Millipore | ATTP04700 | Polycarbonate | Hydrophilic | 0.8 micrometer | Smooth, thin, glass-like | Less than 5 micrograms per centimeter square | Rho kinase dependent |
| 9 | Corning | 3420 | Polycarbonate | Hydrophilic | 3 micrometer | Smooth, thin, glass-like | Less than 5 micrograms per centimeter square | Rho kinase dependent |
| 10 | Nunc | 137060 | Polycarbonate | Hydrophilic | 0.4 micrometer | Smooth, thin, glass-like | Less than 5 micrograms per centimeter square | Rho kinase dependent |
| 11 | Nunc | 137435 | Polycarbonate | Hydrophilic | 3 micrometer | Smooth, thin, glass-like | Less than 5 micrograms per centimeter square | Rho kinase dependent |
| 12 | Millipore | PISP30R48 | Polyethylene terephthalate | Hydrophilic | 3 micrometer | Smooth, thin, glass-like | Less than 5 micrograms per centimeter square | Rho kinase dependent |

Example 14: The Effect of the Use of Defined Medium on the Attachment of Pluripotent Stem Cells to the Planar Substrates of the Present Invention Cells of the human embryonic stem cell line H1 were seeded onto the following planar substrates: Membrane 1 (mixed cellulose ester), Membrane 4 (nylon), Membrane 5 (cellulose acetate) and nitrocellulose. Cells were seeded at a 1:3 dilution in the defined medium mTESR™ and cultured for 24 hours. Parallel cultures un MEF-conditioned medium were included as controls. Culture of the cells in mTESR™ did not affect the ability of the cells to attach to the planar surfaces. Cells were able to attach to membranes 1, 4, and 5, and nitrocellulose. The membrane that showed the great-

TABLE 2

Expression of cell surface markers associated with pluripotency on human embryonic stem cell line H1 after propagated on mixed cellulose esters membranes for 3 passages, as determined by flow cytometry.

| Surface markers | Percentage of the positive cells |
|---|---|
| Tra1-60 | 98.4% |
| Tra1-81 | 98.8% |
| SSEA-3 | 97.5% |
| SSEA-4 | 98.1% |

TABLE 3

Protocol to treat human embryonic stem cells to induce differentiation to insulin-producing cells.

| Time | Treatment |
|---|---|
| 2 days | DMEM-F12 medium<br>2% Fatty-Acid Free Bovine Serum Albumin (FAF-BSA)<br>100 nanogram per milliliter ActivinA<br>20 nanogram per milliliter Wnt3A |
| 2 days | DMEM-F12 medium<br>2% Fatty-Acid Free Bovine Serum Albumin (FAF-BSA)<br>100 nanogram per milliliter ActivinA |

TABLE 3-continued

Protocol to treat human embryonic stem cells to induce differentiation to insulin-producing cells.

| Time | Treatment |
|---|---|
| 3 days | DMEM-F12 medium |
| | 2% BSA |
| | 20 nanogram per milliliter FGF7 |
| | 250 nanomole Cyclopamine-KAAD |
| 4 days | DMEM-F12 medium |
| | 1% B27 supplement |
| | 20 nanogram per milliliter FGF7 |
| | 250 nanomole Cyclopamine-KAAD |
| | 2 micromole Retinal Acid (RA) |
| | 100 nanogram per milliliter Noggin |
| 3 days | DMEM-F12 medium |
| | 1% B27 supplement |
| | 1 micromole ALK5 inhibitor 2 |
| | 100 nanogram per milliliter Noggin |
| | 100 nanogram per milliliter Netrin-4 |
| | 50 nanogram per milliliter Exendin-4 |
| | 1 micromole DAPT |
| 7 days | DMEM-F12 medium |
| | 1% B27 supplement |
| | 1 micromole ALK5 inhibitor 2 |
| 7 days | DMEM-F12 medium |
| | 1% B27 supplement |

TABLE 4

Expression of cell surface markers associated with pluripotency on human embryonic stem cell line H1 after cultured on polycarbonate membranes for 3 passages, as determined by flow cytometry.

| Surface markers | Percentage of the positive cells |
|---|---|
| Tra1-60 | 97.0% |
| Tra1-81 | 96.0% |
| SSEA-3 | 97.6% |
| SSEA-4 | 97.2% |

TABLE 5

Expression of cell surface markers associated with pluripotency on human embryonic stem cell line H1 after propagated on polycarbonate membranes for 9 passages, as determined by flow cytometry.

| Surface markers | Percentage of the positive cells |
|---|---|
| Tra1-60 | 96.8% |
| Tra1-81 | 96.9% |
| SSEA-3 | 95.0% |
| SSEA-4 | 99.7% |

TABLE 6

Expression of cell surface markers associated with definitive endoderm on human embryonic stem cell line H1. The cells were propagated on polycarbonate membranes for 10 passages and treated for definitive endoderm differentiation.

| | CD9 negative cells | CD9 positive cells | CD99 negative cells | CD99 positive cells |
|---|---|---|---|---|
| CXCR4 positive cells | 69.4% | 7.6% | 0.9% | 76.8% |
| CXCR4 negative cells | 12.0% | 11.0% | 5.1% | 17.1% |

TABLE 7

Surface Chemistry (atomic concentration in %).

| Sample | C | N | O | Na | S | Cr |
|---|---|---|---|---|---|---|
| 1 | 39.3 | 8.8 | 51.9 | — | — | — |
| 2 | 38.2 | 9.6 | 52.1 | — | — | — |
| 3 | 41.3 | 8.5 | 49.1 | 0.7 | 0.5 | — |
| 4 | 75.9 | 11.9 | 12.2 | ? | — | — |
| 5 | 59.5 | — | 40.3 | 0.2 | 0.1 | — |
| 6* | 82.0 | 3.5 | 14.2 | 0.2 | 0.1 | — |
| 7 | 79.1 | 0.8 | 19.6 | 0.3 | 0.2 | — |
| 8 | 82.2 | 3.1 | 14.3 | 0.2 | 0.2 | — |
| 9 | 77.2 | 1.1 | 21.5 | 0.1 | 0.1 | — |
| 10 | 76.2 | 2.9 | 20.0 | — | 0.6 | 0.3 |
| 11 | 80.4 | 0.6 | 18.5 | — | 0.2 | 0.3 |
| 12 | 70.2 | 0.2 | 29.5 | $0.1^?$ | — | — |

TABLE 8

Concentrations (in %) of Carbon Functional Groups

| | C—(C,H) | | C—(O,N) | | O—C—O/ O—C=O | | $CO_3$ | | pi-pi* | |
|---|---|---|---|---|---|---|---|---|---|---|
| Sample | B.E. | Atom % | B.E. | Atom % | B.E. | Atom % | B.E. | Atom % | B.E. | Atom % |
| 1 | 284.8 | 2.3 | 287.0 | 29.7 | 288.4 | 7.3 | — | — | — | — |
| 2 | 284.8 | 1.7 | 287.1 | 30.0 | 288.5 | 6.5 | — | — | — | — |
| 3 | 284.8 | 7.6 | 287.0 | 27.1 | 288.4 | 6.6 | — | — | — | — |
| 4 | 284.8 | 51.8 | 285.9 | 12.9 | 287.7 | 11.2 | — | — | — | — |
| 5 | 284.8 | 14.9 | 286.3 | 28.8 | 288.5 | 15.8 | — | — | — | — |
| 6 | 284.8 | 55.5 | 286.1 | 18.2 | 287.6 | 2.8 | 290.9 | 4.2 | 292.4 | 1.3 |
| 7 | 284.8 | 56.5 | 286.4 | 13.6 | 288.3 | 1.4 | 290.4 | 2.8 | 291.3 | 4.7 |
| 8 | 284.8 | 55.8 | 286.1 | 17.4 | 287.5 | 2.8 | 290.8 | 4.1 | 292.1 | 2.1 |
| 9 | 284.8 | 54.1 | 286.4 | 13.0 | 288.5 | 2.1 | 290.4 | 3.1 | 291.2 | 4.9 |
| 10 | 284.8 | 52.5 | 286.3 | 13.6 | 288.6 | 3.4 | 290.6 | 4.2 | 291.9 | 2.6 |
| 11 | 284.8 | 60.8 | 286.4 | 11.7 | 288.6 | $0.2^?$ | 290.7 | 4.8 | 292.0 | 2.8 |
| 12 | 284.8 | 39.2 | 286.4 | 15.5 | 288.8 | 13.2 | 290.5 | $0.5^?$ | 291.6 | 1.9 |

TABLE 9

Concentrations (in %) of Nitrogen Functional Groups

| Sample | C—N B.E. | C—N Atom % | R$_4$—N$^+$ B.E. | R$_4$—N$^+$ Atom % | NO$_2$ B.E. | NO$_2$ Atom % | NO$_3$ B.E. | NO$_3$ Atom % |
|---|---|---|---|---|---|---|---|---|
| 1 | 400.0 | 0.1? | 401.6 | 0.1? | 404.5 | 0.5 | 407.5 | 8.1 |
| 2 | — | — | — | — | 404.6 | 0.4 | 407.5 | 9.2 |
| 3 | 400.0 | 0.1? | 401.7 | 0.1? | 404.4 | 0.4 | 407.4 | 7.8 |
| 4 | 400.0 | 11.9 | — | — | — | — | — | — |
| 5 | — | — | — | — | — | — | — | — |
| 6 | 400.0 | 3.5 | — | — | — | — | — | — |
| 7 | 400.0 | 0.4 | 401.7 | 0.3 | 406.1 | 0.1? | — | — |
| 8 | 400.0 | 2.9 | 401.8 | 0.1? | — | — | 408.3 | 0.1? |
| 9 | 400.0 | 0.6 | 401.7 | 0.4 | 405.8 | 0.1? | — | — |
| 10 | 400.0 | 2.1 | 401.5 | 0.8 | — | — | — | — |
| 11 | 400.0 | 0.2? | 401.8 | 0.4 | — | — | — | — |
| 12 | 400.0 | 0.1? | 401.7 | 0.1? | — | — | — | — |

TABLE 10

Contact angle measurements of the plates of the present invention

| Sample Number | Contact Angle Reading Water (°) 1 | 2 | 3 | Ave | Contact Angle Reading (°) 1 | 2 | 3 | Ave | Comment |
|---|---|---|---|---|---|---|---|---|---|
| 1 | 110.9 | — | — | 110.9 | 18.32 | — | — | 18.32 | |
| 2 | 55.4 | 59.96 | 60.44 | 58.6 | 28.13 | — | — | 28.13 | |
| 3 | 25.54 | 19.79 | — | 22.67 | 29.76 | 25.53 | — | 27.65 | |
| 4 | 29.36 | 31.24 | 32.89 | 31.16 | 31.09 | 25.88 | — | 28.49 | |
| 5 | — | — | — | — | — | — | — | — | Unable to measure |
| 6 | 90.42 | — | — | — | 32.07 | — | — | 32.07 | |
| 7 | 63.59 | — | — | — | 49.49 | — | — | 49.49 | |
| 8 gloss | 58.8 | — | — | 58.8 | 41.29 | — | — | 41.29 | Sample had glossy appearance |
| 8 matt | 72.69 | — | — | 72.69 | 43.3 | — | — | 43.3 | Sample had matt appearance |
| 9 | 71.89 | — | — | 71.89 | 33.82 | — | — | 33.82 | |
| 10 | — | — | — | — | — | — | — | — | Unable to measure |
| 11 | — | — | — | — | — | — | — | — | Unable to measure |
| 12 | 76.96 | 65.187 | — | 71.07 | 46.31 | — | — | 46.31 | — |

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. A method to attach human pluripotent stem cells to a surface of a porous planar substrate containing from at least 8% N to about 12% N, from at least 12% O to at least 55% O, a contact angle from 18 degrees to 32 degrees, and lacking an adlayer and a feeder cell layer, comprising the steps of:
   a) adding Y-27632 to a suspension of pluripotent stem cells;
   b) adding the cell suspension of step a) to the porous planar substrate;
   c) allowing the cells to attach to the surface of the porous planar substrate; and
   d) removing the Y-27632 after the cells attach to the surface of the porous planar substrate,
wherein removal of the Y-27632 does not result in detachment of the cells,
wherein the porous planar substrate comprises mixed cellulose esters, nylon or cellulose acetate, and wherein the attaching comprises culturing the cells and the porous planar substrate under conditions that allow for growth without differentiation.

2. The method of claim 1, wherein the cells are maintained in culture after they have attached to the surface of the porous planar substrate.

3. The method of claim 1, wherein the cells are further differentiated after they have attached to the surface of the porous planar substrate.

4. The method of claim 1, wherein the method comprises from about 0.1 μM to about 100 μM of Y-27632.

5. The method of claim 1, wherein at least 95% of the cells maintain expression of markers associated with pluripotency.

6. The method of claim 1, wherein the Y-27632 is required for the attachment of the cell suspension to the porous planar substrate.

7. A method of enhancing the attachment of human pluripotent stem cells to a surface of a porous planar substrate containing from at least 8% N to about 12% N, from at least 12% O to at least 55% O, a contact angle from 18 degrees to 32 degrees, and lacking an adlayer and a feeder cell layer, comprising the steps of:
   a) treating a suspension of pluripotent stem cells with Y-27632;
   b) contacting the porous planar substrate with the treated suspension of pluripotent human stem cells;
   c) allowing the cells to attach to the surface of the porous planar substrate; and
   d) removing the Y-27632 after the cells attach to the surface of the porous planar substrate,
wherein at least 95% of the cells maintain expression of markers associated with pluripotency,
wherein the porous planar substrate comprises mixed cellulose esters, nylon or cellulose acetate, and
wherein the Y-27632 enhances attachment of the cell suspension to the porous planar substrate.

8. The method of claim 7, wherein the cells are maintained in culture after they have attached to the surface of the porous planar substrate.

9. The method of claim 7, wherein the cells are further differentiated after they have attached to the surface of the porous planar substrate.

10. The method of claim 7, wherein the Y-27632 is removed after the pluripotent stem cells attach to the surface of the porous planar substrate.

11. The method of claim 7, wherein the method comprises from about 0.1 μM to about 100 μM of Y-27632.

12. The method of claim 7, wherein removal of the Y-27632 does not result in detachment of the cells.

13. The method of claim 1, wherein the porous planar substrate comprises mixed cellulose esters.

14. The method of claim 1, wherein the porous planar substrate comprises nylon.

15. The method of claim 1, wherein the porous planar substrate comprises cellulose acetate.

16. The method of claim 1, wherein the Y-27632 enhances attachment of the cell suspension to the porous planar substrate.

17. The method of claim 1, wherein the Y-27632 is required for the attachment of the cell suspension to the porous planar substrate.

18. The method of claim 7, wherein the porous planar substrate comprises mixed cellulose esters.

19. The method of claim 7, wherein the porous planar substrate comprises nylon.

20. The method of claim 7, wherein the porous planar substrate comprises cellulose acetate.

* * * * *